(12) United States Patent
Faham et al.

(10) Patent No.: US 9,347,099 B2
(45) Date of Patent: *May 24, 2016

(54) SINGLE CELL ANALYSIS BY POLYMERASE CYCLING ASSEMBLY

(71) Applicant: Adaptive Biotechnologies Corp., Seattle, WA (US)

(72) Inventors: Malek Faham, Seattle, WA (US); Thomas Willis, Seattle, WA (US)

(73) Assignee: Adaptive Biotechnologies Corp., Seattle, WA (US)

( * ) Notice: Subject to any disclaimer, the term of this patent is extended or adjusted under 35 U.S.C. 154(b) by 139 days.

This patent is subject to a terminal disclaimer.

(21) Appl. No.: 13/908,813

(22) Filed: Jun. 3, 2013

(65) Prior Publication Data

US 2013/0267427 A1    Oct. 10, 2013

Related U.S. Application Data

(63) Continuation of application No. 13/100,395, filed on May 4, 2011, now Pat. No. 8,507,205, which is a continuation-in-part of application No. 12/615,263, filed on Nov. 9, 2009, now Pat. No. 8,236,503.

(60) Provisional application No. 61/112,693, filed on Nov. 7, 2008, provisional application No. 61/332,175, filed on May 6, 2010, provisional application No. 61/446,822, filed on Feb. 25, 2011, provisional application No. 61/452,594, filed on Mar. 14, 2011.

(51) Int. Cl.
| | |
|---|---|
| C12Q 1/68 | (2006.01) |
| C12P 19/34 | (2006.01) |
| C12N 15/10 | (2006.01) |

(52) U.S. Cl.
CPC .......... *C12Q 1/6869* (2013.01); *C12N 15/1072* (2013.01); *C12Q 1/6827* (2013.01); *C12Q 1/6881* (2013.01); *C12Q 1/6883* (2013.01); *C12Q 1/6886* (2013.01); *C12Q 2600/118* (2013.01)

(58) Field of Classification Search
USPC ...................................... 435/6.12, 91.1, 91.2
See application file for complete search history.

(56) References Cited

U.S. PATENT DOCUMENTS

| | | | |
|---|---|---|---|
| 3,270,960 A | 9/1966 | Phillips | |
| 3,773,919 A | 11/1973 | Boswell et al. | |
| 4,474,754 A | 10/1984 | Shimizu et al. | |
| 4,683,195 A | 7/1987 | Mullis et al. | |
| 4,683,202 A | 7/1987 | Mullis | |
| 4,751,188 A | 6/1988 | Valet | |
| 4,800,159 A | 1/1989 | Mullis et al. | |
| 4,876,189 A | 10/1989 | Schetters | |
| 4,942,124 A | 7/1990 | Church | |
| 4,965,188 A | 10/1990 | Mullis et al. | |
| 5,075,217 A | 12/1991 | Weber | |
| 5,126,022 A | 6/1992 | Soane et al. | |
| 5,149,625 A | 9/1992 | Church et al. | |
| 5,168,038 A | 12/1992 | Tecott et al. | |
| 5,189,147 A | 2/1993 | Saito et al. | |
| 5,210,015 A | 5/1993 | Gelfand et al. | |
| 5,213,960 A | 5/1993 | Chang | |
| 5,231,012 A | 7/1993 | Mosmann et al. | |
| 5,296,351 A | 3/1994 | Morley | |
| 5,298,396 A | 3/1994 | Kotzin et al. | |
| 5,326,696 A | 7/1994 | Chang | |
| 5,336,598 A | 8/1994 | Kotzin et al. | |
| 5,364,759 A | 11/1994 | Caskey et al. | |
| 5,399,491 A | 3/1995 | Kacian et al. | |
| 5,418,134 A | 5/1995 | Morley | |
| 5,449,752 A | 9/1995 | Fujii et al. | |
| 5,498,392 A | 3/1996 | Wilding et al. | |
| 5,506,126 A | 4/1996 | Seed et al. | |
| 5,587,128 A | 12/1996 | Wilding et al. | |
| 5,627,037 A | 5/1997 | Ward | |
| 5,627,052 A | 5/1997 | Schrader | |
| 5,635,354 A | 6/1997 | Kourilsky et al. | |
| 5,635,400 A | 6/1997 | Brenner | |
| 5,667,967 A | 9/1997 | Steinman et al. | |
| 5,698,396 A | 12/1997 | Pfreundschuh | |
| 5,699,798 A | 12/1997 | Hochman et al. | |
| 5,776,708 A | 7/1998 | Kotzin et al. | |
| 5,776,737 A | 7/1998 | Dunn | |
| 5,837,447 A | 11/1998 | Gorski | |
| 5,846,719 A | 12/1998 | Brenner et al. | |
| 5,854,033 A | 12/1998 | Lizardi | |
| 5,858,195 A | 1/1999 | Ramsey | |
| 5,925,517 A | 7/1999 | Tyagi et al. | |
| 5,935,793 A | 8/1999 | Wong | |
| 5,969,108 A | 10/1999 | McCafferty et al. | |
| 5,981,176 A | 11/1999 | Wallace | |
| 5,981,179 A | 11/1999 | Lorinez et al. | |
| 6,001,229 A | 12/1999 | Ramsey | |
| 6,010,607 A | 1/2000 | Ramsey | |
| 6,033,546 A | 3/2000 | Ramsey | |
| 6,054,034 A | 4/2000 | Soane et al. | |
| 6,087,096 A | 7/2000 | Dau et al. | |
| 6,090,592 A | 7/2000 | Adams et al. | |
| 6,143,496 A | 11/2000 | Brown et al. | |

(Continued)

FOREIGN PATENT DOCUMENTS

| | | |
|---|---|---|
| CN | 101225441 A | 7/2008 |
| CN | 102272327 A | 12/2011 |

(Continued)

OTHER PUBLICATIONS

U.S. Appl. No. 14/173,712, filed Feb. 5, 2014, Faham et al.

(Continued)

*Primary Examiner* — Kenneth R. Horlick
*Assistant Examiner* — Joyce Tung
(74) *Attorney, Agent, or Firm* — Cooley LLP

(57) ABSTRACT

The invention provides a method of making measurements on individual cells of a population, particularly cells that have identifying nucleic acid sequences, such as lymphoid cells. In one aspect, the invention provides a method of making multiparameter measurements on individual cells of such a population by carrying out a polymerase cycling assembly (PCA) reaction to link their identifying nucleic acid sequences to other cellular nucleic acids of interest. The fusion products of such PCA reaction are then sequenced and tabulated to generate multiparameter data for cells of the population.

20 Claims, 8 Drawing Sheets

(56) References Cited

U.S. PATENT DOCUMENTS

| | | |
|---|---|---|
| 6,172,214 B1 | 1/2001 | Brenner |
| 6,174,670 B1 | 1/2001 | Wittwer et al. |
| 6,258,568 B1 | 7/2001 | Nyren |
| 6,300,070 B1 | 10/2001 | Boles et al. |
| 6,416,948 B1 | 7/2002 | Pilarski et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seegar |
| 6,569,627 B2 | 5/2003 | Wittwer et al. |
| 6,596,492 B2 | 7/2003 | Avery et al. |
| 6,605,272 B2 | 8/2003 | Novak et al. |
| 6,613,525 B2 | 9/2003 | Nelson et al. |
| 6,667,159 B1 | 12/2003 | Walt |
| 6,753,147 B2 | 6/2004 | Vogelstein et al. |
| 6,787,308 B2 | 9/2004 | Balasubramanian et al. |
| 6,794,499 B2 | 9/2004 | Wengel et al. |
| 6,806,079 B1 | 10/2004 | McCafferty et al. |
| 6,858,412 B2 | 2/2005 | Willis et al. |
| 6,919,434 B1 | 7/2005 | Goto et al. |
| 6,964,850 B2 | 11/2005 | Bevilacqua |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham et al. |
| 8,628,927 B2 | 1/2014 | Faham et al. |
| 8,685,678 B2 | 4/2014 | Casbon |
| 8,691,510 B2 | 4/2014 | Faham et al. |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham et al. |
| 8,759,036 B2 | 6/2014 | Wang |
| 8,795,970 B2 | 8/2014 | Faham et al. |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0033490 A1 | 2/2004 | Laird et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | Macevicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Bureznski |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |

(56) References Cited

U.S. PATENT DOCUMENTS

| | | |
|---|---|---|
| 2009/0233301 A1 | 9/2009 | Lee |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021896 A1 | 1/2010 | Han |
| 2010/0021984 A1 | 1/2010 | Edd et al. |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Wondenberg |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0330571 A1 | 12/2010 | Robins et al. |
| 2011/0003291 A1 | 1/2011 | Pasqual |
| 2011/0014659 A1 | 1/2011 | Balazs et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham et al. |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2013/0005584 A1 | 1/2013 | Faham et al. |
| 2013/0017957 A1 | 1/2013 | Faham et al. |
| 2013/0065768 A1 | 3/2013 | Zheng et al. |
| 2013/0116130 A1 | 5/2013 | Fu |
| 2013/0136799 A1 | 5/2013 | Faham |
| 2013/0150252 A1 | 6/2013 | Faham et al. |
| 2013/0196328 A1 | 8/2013 | Pepin et al. |
| 2013/0196861 A1 | 8/2013 | Quake |
| 2013/0202718 A1 | 8/2013 | Pepin et al. |
| 2013/0236895 A1 | 9/2013 | Faham et al. |
| 2013/0253842 A1 | 9/2013 | Sherwood et al. |
| 2013/0288237 A1 | 10/2013 | Robins et al. |
| 2013/0302801 A1 | 11/2013 | Asbury et al. |
| 2013/0324422 A1 | 12/2013 | Faham et al. |
| 2013/0344066 A1 | 12/2013 | Faham et al. |
| 2014/0057799 A1 | 2/2014 | Johnson et al. |
| 2014/0094376 A1 | 4/2014 | Han |
| 2014/0127699 A1 | 5/2014 | Han |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0234835 A1 | 8/2014 | Pepin et al. |
| 2014/0235454 A1 | 8/2014 | Faham et al. |
| 2014/0255929 A1 | 9/2014 | Zheng |
| 2014/0255944 A1 | 9/2014 | Carlton et al. |
| 2014/0256567 A1 | 9/2014 | Robins et al. |
| 2014/0256592 A1 | 9/2014 | Faham et al. |
| 2014/0315725 A1 | 10/2014 | Faham et al. |
| 2014/0322716 A1 | 10/2014 | Robins |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham |
| 2014/0356339 A1 | 12/2014 | Faham et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham |
| 2015/0051089 A1 | 2/2015 | Robins et al. |
| 2015/0065352 A1 | 3/2015 | Faham et al. |
| 2015/0167080 A1 | 6/2015 | Moorhead et al. |
| 2015/0203897 A1 | 7/2015 | Robins et al. |
| 2015/0218656 A1 | 8/2015 | Kirsch et al. |
| 2015/0247182 A1 | 9/2015 | Faham et al. |
| 2015/0247198 A1 | 9/2015 | Klinger et al. |
| 2015/0247201 A1 | 9/2015 | Faham et al. |
| 2015/0252422 A1 | 9/2015 | Faham et al. |
| 2015/0259734 A1 | 9/2015 | Asbury et al. |
| 2015/0299785 A1 | 10/2015 | Livingston et al. |

FOREIGN PATENT DOCUMENTS

| | | |
|---|---|---|
| EP | 0303459 A2 | 2/1989 |
| EP | 0799897 A1 | 10/1997 |
| EP | 1544308 A1 | 6/2005 |
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088432 A1 | 8/2009 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008099588 A | 5/2008 |
| WO | WO 93/01838 A1 | 2/1993 |
| WO | WO 95/28481 A1 | 10/1995 |
| WO | WO 97/13877 A1 | 4/1997 |
| WO | WO 97/18330 A1 | 5/1997 |
| WO | WO 97/46706 A1 | 12/1997 |
| WO | WO 98/01738 A1 | 1/1998 |
| WO | WO 98/44151 A1 | 10/1998 |
| WO | WO 99/19717 A1 | 4/1999 |
| WO | WO 02/24322 A2 | 3/2002 |
| WO | WO 03/044225 A2 | 5/2003 |
| WO | WO 03/052101 A1 | 6/2003 |
| WO | WO 03/059155 A2 | 7/2003 |
| WO | WO 03/044225 A3 | 12/2003 |
| WO | WO 2004/003820 A2 | 1/2004 |
| WO | WO 03/059155 A3 | 3/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/046098 A3 | 8/2004 |
| WO | WO 2004/096985 A2 | 11/2004 |
| WO | WO 2005/005651 A2 | 1/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/059176 A1 | 6/2005 |
| WO | WO 2005/084134 A2 | 9/2005 |
| WO | WO 2005/111242 A2 | 11/2005 |
| WO | WO 2006/076205 A2 | 7/2006 |
| WO | WO 2006/110855 A2 | 10/2006 |
| WO | WO 2006/116155 A2 | 11/2006 |

(56) References Cited

FOREIGN PATENT DOCUMENTS

| WO | WO 2006/138284 A2 | 12/2006 |
|---|---|---|
| WO | WO 2007/134220 A2 | 11/2007 |
| WO | WO 2008/026927 A2 | 3/2008 |
| WO | WO 2008/026927 A3 | 4/2008 |
| WO | WO 2008/039694 A2 | 4/2008 |
| WO | WO 2008/108803 A2 | 9/2008 |
| WO | WO 2008/108803 A3 | 12/2008 |
| WO | WO 2008/147879 A1 | 12/2008 |
| WO | WO 2009/015296 A1 | 1/2009 |
| WO | WO 2009/019657 A2 | 2/2009 |
| WO | WO 2009/021215 A1 | 2/2009 |
| WO | WO 2006/076205 A3 | 4/2009 |
| WO | WO 2009/045898 A2 | 4/2009 |
| WO | WO 2009/070767 A2 | 6/2009 |
| WO | WO 2009/019657 A3 | 8/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/070767 A3 | 10/2009 |
| WO | WO 2009/108866 A3 | 10/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/158521 A2 | 12/2009 |
| WO | WO 2009/108860 A3 | 1/2010 |
| WO | WO 2009/137255 A3 | 1/2010 |
| WO | WO 2010/011894 A1 | 1/2010 |
| WO | WO 2009/151628 A3 | 2/2010 |
| WO | WO 2010/036352 A1 | 4/2010 |
| WO | WO 2009/158521 A3 | 5/2010 |
| WO | WO 2010/053587 A2 | 5/2010 |
| WO | WO 2010/151416 A1 | 12/2010 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2011/106738 A3 | 12/2011 |
| WO | WO 2012/027503 A2 | 3/2012 |
| WO | WO 2012/048340 A2 | 4/2012 |
| WO | WO 2012/048341 A1 | 4/2012 |
| WO | WO 2012/061832 A1 | 5/2012 |
| WO | WO 2012/048340 A3 | 6/2012 |
| WO | WO 2012/083069 A2 | 6/2012 |
| WO | WO 2012/083225 A2 | 6/2012 |
| WO | WO 2012/142213 A2 | 10/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/181428 A2 | 12/2013 |
| WO | WO 2013/188471 A2 | 12/2013 |
| WO | WO 2014/018460 A1 | 1/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2015/002908 A1 | 1/2015 |
| WO | WO 2015/013461 A2 | 1/2015 |
| WO | WO 2015/058159 A1 | 4/2015 |

OTHER PUBLICATIONS

U.S. Appl. No. 14/176,551, filed Feb. 10, 2014, Faham et al.
Kita, et al. T cell receptor clonotypes in skin lesions from patients with systemic lupus erythematosus. J Invest Dermatol. Jan. 1998;110(1):41-6.
Office action dated Feb. 18, 2014 for U.S. Appl. No. 13/459,701.
U.S. Appl. No. 14/611,878, filed Feb. 2, 2015, Moorhead et al.
U.S. Appl. No. 14/640,145, filed Mar. 6, 2015, Robins et al.
Akatsuka, et al. Rapid screening of T-cell receptor (TCR) variable gene usage by multiplex PCR: application for assessment of clonal composition. Tissue Antigens. Feb. 1999;53(2):122-34.
Alexandre, D., et al. "*H. sapiens* rearranged T-cell receptor gamma chain gene, V3RS-J1 (hybrid joint)," GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.
Alexandre, D., et al. "*H. sapiens* rearranged T-cell receptor gamma chain gene, V2-JP1," GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.
Al-Lazikani, et al. Standard conformations for the canonical structures of immunoglobulins. J Mol Biol. Nov. 7, 1997;273(4):927-48.
Bahloul, et al. Clinical impact of molecular diagnostics in low-grade lymphoma. Best Pract Res Clin Haematol. Mar. 2005;18(1):97-111.
Bernardin, et al. Estimate of the total number of CD8+ clonal expansions in healthy adults using a new DNA heteroduplex-tracking assay for CDR3 repertoire analysis. J Immunol Methods. Mar. 1, 2003;274(1-2):159-75.
Blow. PCR's next frontier. Nature Methods. Oct. 2007; 4(10):869-875.
Bradfield, et al. Graft-versus-leukemia effect in acute lymphoblastic leukemia: the importance of tumor burden and early detection. Leukemia. Jun. 2004;18(6):1156-8.
Brenan, et al. High throughput, nanoliter quantitative PCR. Drug Discov Today Technol. 2005 Autumn;2(3):247-53. doi: 10.1016/j.ddtec.2005.08.017.
Buck, et al. Design strategies and performance of custom DNA sequencing primers. Biotechniques. Sep. 1999;27(3):528-36.
Campana. Progress of minimal residual disease studies in childhood acute leukemia. Curr Hematol Malig Rep. Jul. 2010;5(3):169-76. doi: 10.1007/s11899-010-0056-8.
Caporaso, et al. Global patterns of 16S rRNA diversity at a depth of millions of sequences per sample. Proc Natl Acad Sci U S A. Mar. 15, 2011;108 Suppl 1:4516-22. doi: 10.1073/pnas.1000080107. Epub Jun. 3, 2010.
Carlson, et al. Apr. 2011. Profiling the repertoire of TCRB usage in induced and natural Treg cells. J Immunol 186: 62.5 (Abstr).
Cave, et al. Clinical significance of minimal residual disease in childhood acute lymphoblastic leukemia. European Organization for Research and Treatment of Cancer—Childhood Leukemia Cooperative Group. N Engl J Med. Aug. 27, 1998;339(9):591-8.
Chothia, et al. Canonical structures for the hypervariable regions of immunoglobulins. J Mol Biol. Aug. 20, 1987;196(4):901-17.
Chothia, et al. Conformations of immunoglobulin hypervariable regions. Nature. Dec. 21-28, 1989;342(6252):877-83.
Ciudad, et al. Detection of abnormalities in B-cell differentiation pattern is a useful tool to predict relapse in precursor-B-ALL. Br J Haematol. Mar. 1999;104(4):695-705.
Coustan-Smith, et al. Clinical importance of minimal residual disease in childhood acute lymphoblastic leukemia. Blood. Oct. 15, 2000;96(8):2691-6.
Coustan-Smith, et al. Early T-cell precursor leukaemia: a subtype of very high-risk acute lymphoblastic leukaemia. Lancet Oncol. Feb. 2009;10(2):147-56. doi: 10.1016/S1470-2045(08)70314-0. Epub Jan. 13, 2009.
Coustan-Smith, et al. Prognostic importance of measuring early clearance of leukemic cells by flow cytometry in childhood acute lymphoblastic leukemia. Blood. Jul. 1, 2002;100(1):52-8.

(56) References Cited

OTHER PUBLICATIONS

Curran-Everett. Multiple comparisons: philosophies and illustrations. Am J Physiol Regul Integr Comp Physiol. Jul. 2000;279(1):R1-8.
Dash, et al. Paired analysis of TCRα and TCRβ chains at the single-cell level in mice. J Clin Invest. Jan. 2011;121(1):288-95. doi: 10.1172/JCI44752. Epub Dec. 6, 2010.
De Jonge, et al. Evidence based selection of housekeeping genes. PLoS One. Sep. 19, 2007;2(9):e898.
Denucci, et al. Integrin function in T-cell homing to lymphoid and nonlymphoid sites: getting there and staying there. Crit Rev Immunol. 2009;29(2):87-109.
Desmarais, et al. Deep profiling of the mouse TCRβ CDR3 region in thymus and spleen. Oct. 2010. Poster.
Dheda, et al. Validation of housekeeping genes for normalizing RNA expression in real-time PCR. Biotechniques. Jul. 2004;37(1):112-4, 116, 118-9.
Dik, et al. New insights on human T cell development by quantitative T cell receptor gene rearrangement studies and gene expression profiling. J Exp Med. Jun. 6, 2005;201(11):1715-23. Epub May 31, 2005.
Droese, et al. Validation of BIOMED-2 multiplex PCR tubes for detection of TCRB gene rearrangements in T-cell malignancies. Leukemia. Sep. 2004;18(9):1531-8.
Duby, et al. Human T-cell receptor aberrantly rearranged beta-chain J1.5-Dx-J2.1 gene. Proc. Natl. Acad. Sci. USA (1986) GenBank accession No. M13574.1, bases 1 to 100.
Edwards, et al. Multiplex PCR: advantages, development, and applications. PCR Methods Appl. Feb. 1994;3(4):S65-75.
Elnifro, et al. Multiplex PCR: optimization and application in diagnostic virology. Clin Microbiol Rev. Oct. 2000;13(4):559-70.
European search report and opinion dated May 29, 2012 for EP Application No. 10732172.1.
Flohr, et al. Minimal residual disease-directed risk stratification using real-time quantitative PCR analysis of immunoglobulin and T-cell receptor gene rearrangements in the international multicenter trial AIEOP-BFM ALL 2000 for childhood acute lymphoblastic leukemia. Leukemia. Apr. 2008;22(4):771-82. doi: 10.1038/leu.2008.5. Epub Jan. 31, 2008.
Gonzalez, et al. Trafficking of B cell antigen in lymph nodes. Annu Rev Immunol. 2011;29:215-33. doi: 10.1146/annurev-immunol-031210-101255. Epub Dec. 21, 2010.
Henegariu, et al. Multiplex PCR: critical parameters and step-by-step protocol. Biotechniques. Sep. 1997;23(3):504-11.
Hwang, et al. Identification of a commonly used CDR3 region of infiltrating T cells expressing Vbeta13 and Vbeta15 derived from psoriasis patients. J Invest Dermatol. Mar. 2003;120(3):359-64.
International Preliminary Report on Patentability dated Apr. 24, 2014 for PCT/US2013/040221.
Kalinina, et al. Nanoliter scale PCR with TaqMan detection. Nucleic Acids Res. May 15, 1997;25(10):1999-2004.
Kaplinski, et al. MultiPLX Automatic Grouping and Evaluation of PCR Primers. in Methods in Molecular Biology, vol. 402: PCR Primer Design, Nov. 25, 2004, pp. 287-303.
Katz, et al. T cell infiltrate predicts long-term survival following resection of colorectal cancer liver metastases. Ann Surg Oncol. Sep. 2009;16(9):2524-30. doi: 10.1245/s10434-009-0585-3. Epub Jul. 1, 2009.
Kehrl, et al. Chemoattract receptor signaling and its role in lymphocyte motility and trafficking. Curr Top Microbiol Immunol. 2009;334:107-27. doi: 10.1007/978-3-540-93864-4_5.
Kiianitsa, et al., "Development of Tools for T-Cell Repertoire Analysis (TCRB Spectratyping) for the Canine Model of Hematopoietic Cell Transplantation", Blood, ASH—Annual Meeting Abstracts, Nov. 2007, 110(11), Abstract 4873.
Ladetto, et al. Real-time polymerase chain reaction in multiple myeloma: quantitative analysis of tumor contamination of stem cell harvests. Exp Hematol. Jun. 2002;30(6):529-36.
Ladetto, et al. Real-Time polymerase chain reaction of immunoglobulin rearrangements for quantitative evaluation of minimal residual disease in multiple myeloma. Biol Blood Marrow Transplant. 2000;6(3):241-53.
Lucio, et al. Flow cytometric analysis of normal B cell differentiation: a frame of reference for the detection of minimal residual disease in precursor-B-ALL. Leukemia. Mar. 1999;13(3):419-27.
Marelli-Berg, et al. Memory T-cell trafficking: new directions for busy commuters. Immunology. Jun. 2010;130(2):158-65. doi: 10.1111/j.1365-2567.2010.03278.x. Epub Apr. 12, 2010.
Mariani, et al. Comprehensive assessment of the TCRBV repertoire in small T-cell samples by means of an improved and convenient multiplex PCR method. Exp Hematol. Jun. 2009;37(6):728-38. doi: 10.1016/j.exphem.2009.03.003.
Markoulatos, et al. Multiplex polymerase chain reaction: a practical approach. J Clin Lab Anal. 2002;16(1):47-51.
Maryanski, et al. A quantitative, single-cell PCR analysis of an antigen-specific TCR repertoire selected during an in vivo CD8 response: direct evidence for a wide range of clone sizes with uniform tissue distribution. Mol Immunol. Aug. 1999;36(11-12):745-53.
Maslanka, et al. Molecular analysis of T cell repertoires. Spectratypes generated by multiplex polymerase chain reaction and evaluated by radioactivity or fluorescence. Hum Immunol. Sep. 1995;44(1):28-34.
Merriam-Webster (attached; definition of "e.g.," accessed Apr. 25, 2014) http://www.merriam-webster.com/dictionary/e.g.
Merriam-Webster (attached; definition of "substantial," accessed Apr. 25, 2014) http://www.merriam-webster.com/dictionary/substantial.
Monod, et al. IMGT/JunctionAnalysis: the first tool for the analysis of the immunoglobulin and T cell receptor complex V-J and V-D-J JUNCTIONs. Bioinformatics. Aug. 4, 2004;20 Suppl 1:i379-85.
NCBI Accession No. L36092 "Homo sapiens germline beta T-cell receptor locus," NCBI, Jun. 26, 2009, 254 Pages, can be retrieved at <URL:http://www.ncbi.nlm.nih.gov/nuccore/L36092>.
Nicot, et al. Housekeeping gene selection for real-time RT-PCR normalization in potato during biotic and abiotic stress. J Exp Bot. Nov. 2005;56(421):2907-14. Epub Sep. 27, 2005.
Nolan, et al. Quantification of mRNA using real-time RT-PCR. Nat Protoc. 2006;1(3):1559-82.
Notice of allowance dated Feb. 17, 2015 for U.S. Appl. No. 12/425,310.
Notice of allowance dated Oct. 10, 2013 for U.S. Appl. No. 12/794,507.
Office action dated Jan. 16, 2014 for U.S. Appl. No. 13/656,265.
Office action dated Feb. 27, 2015 for U.S. Appl. No. 14/075,075.
Office action dated Apr. 3, 2015 for U.S. Appl. No. 13/861,941.
Office action dated Apr. 4, 2014 for U.S. Appl. No. 12/794,507.
Office action dated Apr. 10, 2015 for U.S. Appl. No. 13/214,111.
Office action dated Apr. 17, 2015 for U.S. Appl. No. 13/459,701.
Office action dated Apr. 26, 2013 for U.S. Appl. No. 12/794,507.
Office action dated May 16, 2014 for U.S. Appl. No. 14/183,163.
Office action dated Jun. 6, 2014 for U.S. Appl. No. 14/183,177.
Office action dated Jun. 16, 2014 for U.S. Appl. No. 14/252,189.
Office action dated Jul. 10, 2013 for U.S. Appl. No. 13/217,126.
Office action dated Jul. 10, 2014 for U.S. Appl. No. 12/794,507.
Office action dated Jul. 11, 2014 for U.S. Appl. No. 13/217,126.
Office action dated Jul. 18, 2014 for U.S. Appl. No. 13/656,265.
Office action dated Oct. 1, 2014 for U.S. Appl. No. 14/183,177.
Office action dated Oct. 2, 2014 for U.S. Appl. No. 14/183,163.
Office action dated Oct. 9, 2014 for U.S. Appl. No. 14/252,189.
Office action dated Nov. 7, 2012 for U.S. Appl. No. 12/794,507.
Office action dated Dec. 2, 2014 for U.S. Appl. No. 14/095,629.
Office action for Australian Patent Application No. 2010263172, Jul. 9, 2014, 4 Pages.
Office Action for Canadian Patent Application No. 2,765,949, Mailed Apr. 3, 2014, 4 Pages.
Office Action for Chinese Patent Application No. 201080028875.2, Mailed Feb. 13, 2014, 5 pages (With English Summary).
Office Action for European Patent Application No. EP 10722512.0, Dec. 17, 2012, 5 Pages.
Office Action for Israel Patent Application No. IL 217200, Jan. 21, 2013, 4 Pages.

(56) References Cited

OTHER PUBLICATIONS

Office action for Israel Patent Application No. IL 217200, Mar. 18, 2014, 8 Pages.
Office action for Korean Patent Application No. 10-2011-7030953, May 30, 2014, 5 Pages.
Office action for Russian Patent Application No. 2012101828/10(002474), Mar. 28, 2014, 5 Pages.
PCT International Search Report and Written Opinion for PCT/US2013/040221, Sep. 23, 2013, 16 Pages.
PCT International Search Report and Written Opinion, PCT Application No. PCT/US2010/021264, Apr. 14, 2010, 7 pages.
PCT International Search Report and Written Opinion, PCT/2013/045994, Oct. 25, 2013, 16 Pages.
PCT International Search Report and Written Opinion, PCT/US2010/037477, Sep. 24, 2010, 10 pages.
PCT International Search Report and Written Opinion, PCT/US2011/049012, Apr. 10, 2012, 9 Pages.
PCT International Search Report and Written Opinion, PCT/US2011/026373, Oct. 20, 2011, 14 Pages.
PCT International Search Report and Written Opinion, PCT/US2012/061193, Mar. 28, 2013, 12 Pages.
PCT International Search Report and Written Opinion, PCT/US2012/068617, Jun. 13, 2013, 8 Pages.
PCT International Search Report and Written Opinion, PCT/US2013/062925, Nov. 25, 2013, 12 Pages.
Pohl, et al. Principle and applications of digital PCR. Expert Rev Mol Diagn. Jan. 2004;4(1):41-7.
Puisieux, et al. Oligoclonality of tumor-infiltrating lymphocytes from human melanomas. J Immunol. Sep. 15, 1994;153(6):2807-18.
Rasmussen, et al. Quantitation of minimal residual disease in multiple myeloma using an allele-specific real-time PCR assay. Exp Hematol. Sep. 2000;28(9):1039-45.
Reischl, et al. Quantitative PCR. A survey of the present technology. Mol Biotechnol. Feb. 1995;3(1):55-71.
Robins, et al. High-throughput sequencing of T-cell receptors. Sep. 2010. Poster.
Robins, et al. Overlap and effective size of the human CD8+ T cell receptor repertoire. Sci Transl Med. Sep. 1, 2010;2(47):47ra64. doi: 10.1126/scitranslmed.3001442.
Robins, et al. Overlap of the human CD8+ T cell receptor repertoire. Oct. 2010. Poster.
Robins. 2010. Overlap and effective size of the human CD8+ T cell repertoire. Keystone Symposia. Immunological Mechanisms of Vaccination (Oral Presentation).
Robins. Detecting and monitoring lymphoma with high-throughput sequencing. Oncotarget. Apr. 2011;2(4):287-8.
Rock, et al. CDR3 length in antigen-specific immune receptors. J Exp Med. Jan. 1, 1994;179(1):323-8.
Roshal, et al. Immaturity associated antigens are lost during induction for T cell lymphoblastic leukemia: implications for minimal residual disease detection. Cytometry B Clin Cytom. May 2010;78(3):139-46. doi: 10.1002/cyto.b.20511.
Rozen, et al. Primer3 on the WWW for general users and for biologist programmers. Methods Mol Biol. 2000;132:365-86.
Saada, et al. Models for antigen receptor gene rearrangement: CDR3 length. Immunol Cell Biol. Jun. 2007;85(4):323-32. Epub Apr. 3, 2007.
Sandberg, et al. Capturing whole-genome characteristics in short sequences using a naïve Bayesian classifier. Genome Res. Aug. 2001;11(8):1404-9.
Santalucia. Physical principles and visual-OMP software for optimal PCR design. Methods Mol Biol. 2007;402:3-34.
Santamaria, et al. Beta-cell-cytotoxic CD8+ T cells from nonobese diabetic mice use highly homologous T cell receptor alpha-chain CDR3 sequences. J Immunol. Mar. 1, 1995;154(5):2494-503.
Silver, et al. Selection of housekeeping genes for gene expression studies in human reticulocytes using real-time PCR. BMC Mol Biol. Oct. 6, 2006;7:33.
Standard Sequencing Primers, Max Planck Genome Center Cologne, Jan. 15, 2011, downloaded from https://genomecentre.mpipz.mpg.de/SeqOrderDB/export/sequencing-primers.html.
Stein, et al. Chemokine control of lymphocyte trafficking: a general overview. Immunology. Sep. 2005;116(1):1-12.
Steinmetz, et al. Chemokines and B cells in renal inflammation and allograft rejection. Frontiers in Bioscience (Schol. Ed.), Jun. 1, 2009, vol. 1, pp. 13-22.
Szczepanski, et al. Minimal residual disease in leukaemia patients. Lancet Oncol. Jul. 2001;2(7):409-17.
Tewhey, et al. Corrigendum: Microdroplet-based PCR enrichment for large-scale targeted sequencing. Nat Biotechnol. Feb. 2010;28(2):178.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Triebel, et al. A unique V-J-C-rearranged gene encodes a gamma protein expressed on the majority of CD3+ T cell receptor-alpha/beta-circulating lymphocytes. J Exp Med. Feb. 1, 1988;167(2):694-9.
Van Der Velden, et al. Optimization of PCT-based minimal residual disease diagnostics for childhood acute lymphoblastic leukemia in a multi-center setting. Leukemia. Apr. 2007;21(4):706-13. Epub Feb. 8, 2007.
Van Der Velden, et al. Real-time quantitative PCR for detection of minimal residual disease before allogeneic stem cell transplantation predicts outcome in children with acute lymphoblastic leukemia. Leukemia. Sep. 2001;15(9):1485-7.
Van Dongen, et al. Prognostic value of minimal residual disease in acute lymphoblastic leukaemia in childhood. Lancet. Nov. 28, 1998;352(9142):1731-8.
Venturi, et al. TCR beta-chain sharing in human CD8+ T cell responses to cytomegalovirus and EBV. J Immunol. Dec. 1, 2008;181(11):7853-62.
Venturi, et al. The molecular basis for public T-cell responses? Nat Rev Immunol. Mar. 2008;8(3):231-8. doi: 10.1038/nri2260.
Verhagen, et al. Application of germline IGH probes in real-time quantitative PCR for the detection of minimal residual disease in acute lymphoblastic leukemia. Leukemia. Aug. 2000;14(8):1426-35.
Vogelstein, et al. Digital PCR. Proc Natl Acad Sci U S A. Aug. 3, 1999;96(16):9236-41.
Ward, et al. Mechanisms of chemokine and antigen-dependent T-lymphocyte navigation. Biochem J. Feb. 15, 2009;418(1):13-27. doi: 10.1042/BJ20081969.
Wood. 9-color and 10-color flow cytometry in the clinical laboratory. Arch Pathol Lab Med. May 2006;130(5):680-90.
U.S. Appl. No. 61/045,586, filed Apr. 16, 2008, Han et al.
U.S. Appl. No. 12/945,678, filed Nov. 12, 2010, Faham et al.
U.S. Appl. No. 13/174,086, filed Jun. 30, 2011, Faham et al.
U.S. Appl. No. 13/196,885, filed Aug. 2, 2011, Moorhead et al.
U.S. Appl. No. 13/369,031, filed Feb. 8, 2012, Faham et al.
U.S. Appl. No. 13/487,980, filed Jun. 4, 2012, Faham et al.
U.S. Appl. No. 13/627,497, filed Sep. 26, 2012, Faham et al.
U.S. Appl. No. 13/861,941, filed Apr. 12, 2013, Pepin et al.
U.S. Appl. No. 13/905,406, filed May 30, 2013, Faham et al.
Arstila et al., "A direct estimate of the human αβ T cell receptor diversity," Science 286:958-961 (1999).
Bagnara, et al. IgV gene intraclonal diversification and clonal evolution in B-cell chronic lymphocytic leukaemia. Br J Haematol. Apr. 2006;133(1):50-8.
Batzoglou. The many faces of sequence alignment. Briefings in Bioinformatics. 2005; 6:6-22.
Beishuizen, et al. Analysis of Ig and T-cell receptor genes in 40 childhood acute lymphoblastic leukemias at diagnosis and subsequent relapse: implications for the detection of minimal residual disease by polymerase chain reaction analysis. Blood. Apr. 15, 1994;83(8):2238-47.
Bene, et al. How and why minimal residual disease studies are necessary in leukemia: a review from WP10 and WP12 of the European LeukaemiaNet. Haematologica. Aug. 2009;94(8):1135-50. Epub Jul. 7, 2009.

(56) References Cited

OTHER PUBLICATIONS

Benichou, et al. Rep-Seq: uncovering the immunological repertoire through next-generation sequencing. Immunology. Mar. 2012;135(3):183-91. doi: 10.1111/j.1365-2567.2011.03527.x.
Bonarius, et al. Monitoring the T-Cell Receptor Repertoire at Single-Clone Resolution. PLoS One. Dec. 20, 2006;1:e55.
Boria, et al. Primer sets for cloning the human repertoire of T cell receptor variable regions. BMC Immunology. 2008; 9:50.
Boyd et al. Measurement and clinical monitoring of human lymphocyte clonality by massively parallel VDJ pyrosequencing. Sci Transl. Med. 1(12):12ra23 (2009).
Boyd, et al. Individual variation in the germline Ig gene repertoire inferred from variable region gene rearrangements. J Immunol. Jun. 15, 2010;184(12):6986-92. Epub May 21, 2010.
Brehm-Stecher, et al. Single-cell microbiology: tools, technologies, and applications. Microbiology and molecular biology reviews. 2004; 68(3):538-559.
Brisco, et al. Determining the repertoire of IGH gene rearrangements to develop molecular markers for minimal residual disease in B-lineage acute lymphoblastic leukemia. J Mol Diagn. May 2009;11(3):194-200. Epub Mar. 26, 2009.
Bruggemann, et al. Clinical significance of minimal residual disease quantification in adult patients with standard-risk acute lymphoblastic leukemia. Blood. Feb. 1, 2006;107(3):1116-23. Epub Sep. 29, 2005.
Campana. Minimal residual disease in acute lymphoblastic leukemia. Semin Hematol. Jan. 2009;46(1):100-6.
Campbell et al., "Subclonal phylogenetic structures in cancer revealed by ultra-deep sequencing," PNAS 105(35):13081-13086 (2008).
Choi, et al. Clonal evolution in B-lineage acute lymphoblastic leukemia by contemporaneous VH-VH gene replacements and VH-DJH gene rearrangements. Blood. Mar. 15, 1996;87(6):2506-12.
Choi, et al. Relapse in children with acute lymphoblastic leukemia involving selection of a preexisting drug-resistant subclone. Blood. Jul. 15, 2007;110(2):632-9. Epub Mar. 19, 2007.
The International Search Report for PCT Application PCT/US2009/006053 dated Jun. 15, 2010.
Costabile, et al. Molecular approaches in the diagnosis of primary immunodeficiency diseases. Hum Mutat. Dec. 2006;27(12):1163-73.
Cronn, et al. Multiplex sequencing of plant chloroplast genomes using Solexa sequencing-by-synthesis technology. Nucleic Acids Res. Nov. 2008;36(19):e122.
Curran et al., "Nucleotide sequencing of psoriatic arthritis tissue before and during methotrexate administration reveals a complex inflammatory T cell infiltrate with very few clones exhibiting features that suggest they drive the inflammatory process by recognizing autoantigens," J Immunol 172:1935-1944 (2004).
Currier, et al. Spectratype/immunoscope analysis of the expressed TCR repertoire. Current Protocols in Immunology. 2000; Supplement 38:10.28.1-10.28.24.
Davi, et al. Lymphocytic progenitor cell origin and clonal evolution of human B-lineage acute lymphoblastic leukemia. Blood. Jul. 15, 1996;88(2):609-21.
Davis, et al. Staining of cell surface human CD4 with2-F-pyrimidine-containing RNA amptamers for flow cytometry. Nucleic Acids Research. 1998; 26(17):3915-3924.
Deng et al., "Gene profiling involved in immature CD4+ T lymphocyte responsible for systemic lupus erythematosus," Molecular Immunology 43:1497-1507 (2006).
Dohm, et al. Substantial biases in ultra-short read data sets from high throughput DNA sequencing. Nucleic Acids Research. 2008; 36:e105.
Dou, et al. Analysis of T cell receptor Vbeta gene usage during the course of disease in patients with chronic hepatitis B. J Biomed Sci. Nov.-Dec. 1998;5(6):428-34.
Du et al., "TCR spectratyping revealed T lymphocytes associated with graft-versus-host disease after allogeneic hematopoietic stem cell transplantation," Leukemia & Lymphoma 48(8):1618-1627 (2007).
Edd, et al. Controlled encapsulation of single cells into monodisperse picoliter drops. Lap Chip. 2008; 8(8):1262-1264.
European office action dated Mar. 28, 2012 for EP Application No. 09764927.1.
Freeman et al., "Profiling the T-cell receptor beta-chain repertoire by massively parallel sequencing," Genome Res. 19(10):1817-1824 (2009).
Fritz et al., "Alterations in the spinal cord T cell repertoire during relapsing experimental autoimmune encephalomyelitis," J Immunol 164:6662-6668 (2000).
Garcia-Castello, et al. Detection of clonal immunoglobulin and T-cell receptor gene recombination in hematological malignancies: monitoring minimal residual disease. Cardiovascular & Haematological Disorders—Drug Targets. 2009; 9:124-135.
Germano, et al. Clonality profile in relapsed precursor-B-ALL children by GeneScan and sequencing analyses. Consequences on minimal residual disease monitoring. Leukemia. Aug. 2003;17(8):1573-82.
Giuggio, et al. Evolution of the intrahepatic T cell repertoire during chronic hepatitis C virus infection. Viral Immunol. 2005;18(1):179-89.
Golembowski, et al. Clonal evolution in a primary cutaneous follicle center B cell lymphoma revealed by single cell analysis in sequential biopsies. Immunobiology. Apr. 2000;201(5):631-44.
Gonzalez, et al. Incomplete DJH rearrangements as a novel tumar target for minimal residual disease quantitation in multiple myeloma using real-time PCR. Leukemia. 2003; 17:1051-1057.
Gonzalez, et al. Incomplete DJH rearrangements of the IgH gene are frequent in multiple myeloma patients: immunobioligcal characteristics and clinical applications. Leukemia. 2003; 17:1398-1403.
Gorski, et al. Circulating T cell repertoire complexity in normal individuals and bone marrow recipients analyzed by CDR3 size spectratyping. Correlation with immune status. J Immunol May 15, 1994;152(10):5109-19.
Green, et al. Clonal diversity of Ig and T-cell-receptor gene rearrangements identifies a subset of childhood B-precursor acute lymphoblastic leukemia with increased risk of relapse. Blood. Aug. 1, 1998;92(3):952-8.
Gurrieri, et al. Chronic lymphocytic leukemia B cells can undergo somatic hypermutation and intraclonal immunoglobulin V(H)DJ(H) gene diversification. J Exp Med. Sep. 2, 2002;196(5):629-39.
Han, et al. Immunorepertoire analysis by multiplex PCR amplification and high throughput sequencing. Abstract. The 96 Annual Meeting of the American Association of Immunologists, Seattle, Washington, May 8-12, 2009. Available at http://jimmunol.org//cgi/content/meeting_abstract/182/1_MeetingAbstracts/42.6?sid=257929f1-97a9-4330-8e96-1750aa240e69. Accessed Nov. 24, 2010.
Heger, M. Studies Highlight Challenges of Immune Repertoire Sequencing's Clinical Applicability. Available at http://www.genomeweb.com/sequencing/studies-highlight-challenges-immune-repertoire-sequencings-clinical-applicabilit?hq_e=el&hq_m=966798&hq_1=10&hq_v=2357e2f0b3. Accessed Apr. 6, 2011.
Holt, "Q &A: BC cancer agency's Robert Holt on sequencing the immune repertoire in immune reconstitution," Genome Web (www.genomeweb.com) Jun. 30, 2009.
Illumina. Data Sheet: Sequencing. Genomic Sequencing. Pub. No. 770.2008-016 Copyright 2010. Reference states: "Current as of Jan. 30, 2009."
International search report and written opinion dated Sep. 22, 2011 for PCT Application No. US11/000791.
International search report and written opinion dated Oct. 19, 2011 for PCT Application No. US11/000792.
Ishii et al., "Isolation and expression profiling of genes upregulated in the peripheral blood cells of systemic lupus erythematosus patients," DNA Research 12:429-439 (2005).

(56) References Cited

OTHER PUBLICATIONS

Jacobi et al., "Activated memory B cell subsets correlate with disease activity in systemic lupus erythematosus: delineation by expression of CD27, IgD, and CD95," Arthritis & Rheumatism 58(6):1762-1773 (2008).

Jacobi et al., "Correlation between circulating CD27high plasma cells and disease activity in patients with systemic lupus erythematosus," Arthritis & Rheumatism 48(5):1332-1342 (2003).

Jena, et al. Amplification of genes, single transcripts and cDNA libraries from one cell and direct sequence analysis of amplified products derived from one molecule. J. Immunol. Methods. 1996; 190:199-213.

Kato et al., "Analysis of accumulated T cell clonotypes in patients with systemic lupus erythematosus," Arthritis & Rheumatism 43(12):2712-2721 (2000).

Kim, et al An efficient and reliable DNA extraction method for preimplantation genetic diagnosis: a comparison of allele drop out and amplification rates using different single cell iysis methods. Fertility and Sterility. 2009; 92: 814-818.

Kim, et al. Polony multiplex analysis of gene expression (PMAGE) in mouse hypertrophic cardiomyopathy. Science. Jun. 8, 2007;316(5830):1481-4.

Kneba, et al. Analysis of rearranged T-cell receptor beta-chain genes by polymerase chain reaction (PCR0 DNA sequencing and automated high resolution PCR fragment analysis. Blood. 1995; 86:3930-3937.

Kobari, et al. T cells accumulating in the inflamed joints of a spontaneous murine model of rheumatoid arthritis become restricted to common clonotypes during disease progression. Int Immunol. Jan. 2004;16(1):131-8.

Langerak, et al. Immunoglobulin/T-cell receptor clonality diagnostics. Exoert Opin. Med. Diagn. 2007; 1(3):451-461.

Langerak, et al. Polymerase chain reaction-based clonality testing in tissue samples with reactive lymphoproliferations: usefulness and pitfalls. A report of the BIOMED-2 Concerted Action BMH4-CT98-3936. Leukemia. Feb. 2007;21(2):222-9. Epub Dec. 14, 2006.

Laplaud et al., "Blood T-cell receptor β chain transcriptome in multiple sclerosis. Characterization of the T cells with altered CDR3 length distribution," Brain 127:981-995 (2004).

Laplaud et al., "Serial blood T cell repertoire alterations in multiple sclerosis patients; correlation with clinical and MRI parameters," J Neroimmunol 177:151-160 (2006).

Li, et al. An improved one-tube RT-PCR protocol for analyzing single-cell gene expression in individual mammalian cells. Anal. Bioanal. Chem. 2010; 397: 1853-1859.

Li, et al. Clonal rearrangements in childhood and adult precursor B acute lymphoblastic leukemia: a comparative polymerase chain reaction study using multiple sets of primers. Eur J Haematol. Oct. 1999;63(4):211-8.

Li, et al. Detailed clonality analysis of relapsing precursor B acute lymphoblastic leukemia: implications for minimal residual disease detection. Leukemia Research. 2001; 25:1033-1045.

Li, et al. Sequence analysisn of clonal immunoglobulin and T-cell receptor gene rearrangements in children with acute lymphoblastic leukemia at diagnosis and at relapse: implications for pathogenesis and for the clinical utility of PCR-based methods of minimal residual disease detection. Blood. 2003; 102:4520-4526.

Li, et al. Utilization of Ig heavy chain variable, diversity, and joining gene segments in children with B-lineage acute lymphoblastic leukemia: implications for the mechanisms of VDJ recombination and for pathogenesis. Blood. Jun. 15, 2004;103(12):4602-9. Epub Mar. 9, 2004.

Logan, et al. High-throughput VDJ sequencing for quantification of minimal residual disease in chronic lymphocytic leukemia and immune reconstitution assessment. Proc Natl Acad Sci U S A. Dec. 27, 2011;108(52):21194-9. Epub Dec. 12, 2011.

Lovisa, et al. IGH and IGK gene rearrangements as PCR targets for pediatric Burkitt's lymphoma and mature B-ALL MRD analysis. Lab Invest. Oct. 2009;89(10):1182-6. Epub Aug. 10, 2009.

Luo et al., "Analysis of the interindividual conservation of T cell receptor α- and β-chain variable regions gene in the peripheral blood of patients with systemic lupus erythematosus," Clin Exp Immunol 154:316-324 (2008).

Margulies, et al. Genome sequencing in microfabricated high-density picolitre reactors. Nature. Sep. 15, 2005;437(7057):376-80. Epub Jul. 31, 2005.

Mato et al., "Correlation of clonal T cell expansion with disease activity in systemic lupus erythematosus," Int Immunol 9(4):547-554 (1997).

Matolcsy, et al. Clonal evolution of B cells in transformation from low- to high-grade lymphoma. Eur J Immunol. Apr. 1999;29(4):1253-64.

Matsumoto et al., "CDR3 spectratyping analysis of the TCR repertoire in myasthenia gravis," J Immunol 176:5100-5107 (2006).

Matsumoto et al., "Complementarity-determining region 3 spectratyping analysis of the TCR repertoire in multiple sclerosis," J Immunol 170:4846-4853 (2003).

Meleshko, et al. Rearrangements of IgH, TCRD and TCRG genes as clonality marker of childhood acute lymphoblastic leukemia. Exp Oncol. Dec. 2005;27(4):319-24.

Menezes et al., "A public T cell clonotype within a heterogeneous autoreactive repertoire is dominant in driving EAE," J Clin Invest 117(8):2176-2185 (2007).

Michalek, et al. Detection and long-term in vivo monitoring of individual tumor-specific T cell clones in patients with metastatic melanoma. J Immunol. Jun. 1, 2007;178(11):6789-95.

Moss, et al. The human T cell reeptor in health and disease. Annu. Rev. Immunol. 1992; 10:71-96.

Muraro et al., "Molecular tracking of antigen-specific T cell clones in neurological immune-mediated disorders," Brain 126:20-31 (2003).

Nardi, et al. Quantitative monitoring by polymerase colony assay of known mutations resistant to ABL kinase inhibitors. Oncogene. Jan. 31, 2008;27(6):775-82. Epub Aug. 6, 2007, 1-8.

Neale, et al. Comparative analysis of flow cytometry and polymerase chain reaction for the detection of minimal residual disease in childhood acute lymphoblastic leukemia. Leukemia. May 2004;18(5):934-8.

Nguyen, et al. Identification of errors introduced during high throughput sequencing of the T cell receptor repertoire. BMC Genomics. Feb. 11, 2011;12:106.

Notification of Grant dated Jul. 26, 2011 for patent serial No. GB 2467704.

Novak, et al. Single-cell multiplex gene detection and sequencing With microfluidically generated agarose emulsions. Angewandte Chernie. 2011; 50: 390-395, with supplemental material.

Office action dated May 9, 2012 for U.S. Appl. No. 13/100,395.

Office action dated Sep. 15, 2011 for U.S. Appl. No. 12/615,263.

Office action dated Dec. 6, 2012 for U.S. Appl. No. 13/100,395.

Ogle, et al. Direst measurement of lymphocyte receptor diversity. Nucleic Acids Research. 2003; 31(22):e139.

Okajima et al., "Analysis of T cell receptor Vβ diversity in peripheral CD4+ and CD8+ T lymphocytes in patients with autoimmune thyroid diseases," Clin Exp Immunol 155:166-172 (2008).

Packer et al., "Optimized clonotypic analysis of T-cell receptor repertoire in immune reconstitution," Exp. Hematol 35(3):516-521 (2007).

Panzer-Grumayer, et al. Immunogenotype changes prevail in relapses of young children with TEL-AML1-positive acute lymphoblastic leukemia and derive mainly from clonal selection. Clin Cancer Res. Nov. 1, 2005;11(21):7720-7.

Pels, et al. Clonal evolution as pathogenetic machanism in relapse of primary CNS lymphoma. Neurology. Jul. 13, 2004;63(1):167-9.

Pira, et al. Human naive CD4 T-cell clones specific for HIV envelope persist for years in vivo in the absence of antigenic challenge. J Acquir Immune Defic Syndr. Oct. 1, 2005;40(2):132-9.

Pop, et al. Bioinformatics challenges of new sequencing technology. Trends Genet. Mar. 2008;24(3):142-9.

Ray, et at. Single cell multiplex PCR amplification of five dystrophin gene exons combined with gender determination. Molecular Human Reproduction. 2001; 7(5): 489-494.

(56) References Cited

OTHER PUBLICATIONS

Reddy, et al. Systems analysis of adaptive immunity by utilization of high-throughput technologies. Curr Opin Biotechnol. Aug. 2011;22(4):584-9. Epub May 12, 2011.
Reinartz, et al. Massively parallel signature sequencing (MPSS) as a tool for in-depth quantitative gene expression profiling in all organisms. Brief Funct Genomic Proteomic. Feb. 2002;1(1):95-104.
Ria, et al. Collagen-specific T-cell repertoire in blood and synovial fluid varies with disease activity in early rheumatoid arthritis. Arthritis Res Ther. 2008;10(6):R135. Epub Nov. 17, 2008.
Rickison, et al. Human cytotoxic T lymphocyte responses to Epstein-Barr virus infection. Annu Rev Immunol. 1997;15:405-31.
Risitano et al., "In-vivo dominant immune responses in aplastic anaemia: molecular tracking of putatively pathogenetic T-cell clones by TCR β-CDR3 sequencing," Lancet 364:355-364 (2004).
Robins et al., "Comprehensive assessment of T-cell receptor beta-chain diversity in alphabeta T cells," Blood 114(19):4099-4107 (2009).
Robins, et al. Ultra-sensitive detection of rare T cell clones. Immunol Methods. Jan. 31, 2012;375(1-2):14-9. Epub Sep. 10, 2011.
Rosenquist, et al. Clonal evolution as judged by immunoglobulin heavy chain gene rearrangements in relapsing precursor-B acute lymphoblastic leukemia. Eur J Haematol. Sep. 1999;63(3):171-9.
Rougemont, et al. Probabilistic base calling of Solexa sequencing data. BMC Bioinformatics. 2008; 9:431.
Ryan, et al. Clonal evolution of lymphoblastoid cell lines. Lab Invest. Nov. 2006;86(11):1193-200. Epub Oct. 2, 2006.
Schaufelberger, et al. An uneven expression of T cell receptor V genes in the arterial wall and peripheral blood in giant cell arteritis. Inflammation. Dec. 2008;31(6):372-83.
Scholler, et al. Analysis of T cell receptor alpha beta variability in lymphocytes infiltrating melanoma primary tumours and metastatic lesions. Cancer Immunol Immunother. Oct. 1994;39(4):239-48.
Schwab et al., "CD8+ T-cell clones dominate brain infiltrates in Rasmussen encephalitis and persist in the periphery," Brain 132:1236-1246 (2009).
Shen, et al. Comparing platforms for C. elegans mutant identification using high-throughput whole-genome sequencing. PLoS One. 2008;3(12):e4012.
Skulina et al., "Multiple sclerosis: brain-infiltrating CD8+ T cells persist as clonal expansions in the cerebrospinal fluid and blood," PNAS 101(8):2428-2433 (2004).
Sramkova, et al. Detectable minimal residual disease before allogeneic hematopoietic stem cell transplantation predicts extremely poor prognosis in children with acute lymphoblastic leukemia. Pediatr Blood Cancer. Jan. 2007;48(1):93-100.
Steenbergen, et al. Distinct ongoing Ig heavy chain rearrangement processes in childhood B-precursor acute lymphoblastic leukemia. Blood. Jul. 15, 1993;82(2):581-9.
Steward, et al. A polymerase chain reaction study of the stability of Ig heavy-chain and T-cell receptor delta gene rearrangements between presentation and relapse of childhood B-lineage acute lymphoblastic leukemia. Blood. Mar. 1, 1994;83(5):1355-62.
Struyk, et al. T cell receptors in rheumatoid arthritis. Arthritis Rheum. May 1995;38(5):577-89.
Sumida et al., "T cell receptor repertoire of infiltrating T cells in lips of Sjögren's syndrome patients," J Clin Invest 89:681-685 (1992).
Sumida et al., "T cell receptor Vα repertoire of infiltrating T cells in labial salivary glands from patients with Sjögren's syndrome," J Rheumatol 21: 1655-1661 (1994).
Tackenberg et al., "Clonal expansions of CD4+ β helper T cells in autoimmune myasthenia gravis," Eur J Immunol 37:849-863 (2007).
Tajiri, et al. Cell-microarray analysis of antigen-specific B-cells: single cell analysis of antigen receptor expression and specificity. Cytometry Part A. 2007; 71A: 961-967.
Thornhill, et al. A comparison of different lysis buffers to assess allele dropout from single cells for preimplantation genetic diagnosis. Prenatal Diagnosis. 2001; 21: 490-497.
Tokimitsu, et al. Single lymphocyte analysis with a microwell array chip. Cytometry. 2007; Part A, 71A: 1003-1010.

UK Combined Search Report and Office action dated Jun. 29, 2012 for UK application No. GB1209668.1.
UK Combined Search Report and Office action dated May 26, 2011 for UK application No. GB1105068.9.
UK office action dated May 25, 2011 for UK application No. GB1009641.0.
UK office action dated Oct. 20, 2010 for UK application No. GB1009641.0.
UK Search Report and office action dated Jan. 12, 2012 for UK application No. GB1120209.0.
UK Search Report and office action dated Jul. 7, 2010 for UK application No. GB1009641.0.
Umibe et al., "Clonal expansion of T cells infiltrating in the airways of non-atopic asthmatics," Clin Exp Immunol 119:390-397 (2000).
Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. Dec. 2003;17(12):2257-317.
Wang, et al. High throughput sequencing reveals a complex pattern of dynamic interrelationships among human T cell subsets. Proc Natl Acad Sci U S A. Jan. 26, 2010; 107(4): 1518-1523.
Wang, et al. Quantitative measurement of pathogen-specific human memory T cell repertoire diversity using a CDR3 beta-specific microarray. BMC Genomics. Sep. 19, 2007;8:329.
Warren et al., "Profiling model T-cell metagenomes with short reads," Bioinformatics 25(4):458-464 (2009).
Warren, et al. Exhaustive T-cell repertoire sequencing of human peripheral blood samples reveals signatures of antigen selection and a directly measured repertoire size of at least 1 million clonotypes. Genome Res. Feb. 24, 2011. [Epub ahead of print].
Weinstein et al., "High-throughput sequencing of the zebrafish antibody repertoire," Science 324:807-810 (2009).
Wells, et al. Strategies for preimplantation genetic diagnosis of single gene disorders by DNA amplification. Prenatal Diagnosis. 1998; 18: 1389-1401.
Wetmur, et al. An emulsion polymerase chain reaction-based method for molecular haplotyping. Methods in Molecular Biology. 1996; 410: 351-361.
Wetmur, et al. Linking emulsion PCR haplotype analysis. chapter 11, in Park (editor), PCR Protocols, Methods En Molecular Biology. 2011; 687: 165-175.
Wetmur, et al. Molecular haplotyping by linking emulsion PCR: analysis of paraoxonase 1 haplotypes and phenotypes. Nucleic Acids Research. 2005; 33(8):2615-2619.
Wlodarski, et al. Molecular strategies for detection and quantitation of the clonal cytotoxic T-cell responses in aplastic anemia and myelodysplastic syndrome. Blood. 2006; 108:2632-2641.
Wlodarski, et al. Pathologic clonal cytotoxic T-cell responses: nonrandom nature of the T-cell-receptor restriction in large granular lymphocyte leukemia. Blood. 2005; 106:2769-2779.
Yin et al., "Antiretroviral therapy restores diversity in the T-cell receptor Vβ repertoire of CD4 T-cell subpopulations among human immunodeficiency virus type 1-infected children and adolescents," Clin Vac Immunol 16(9):1293-1301 (2009).
Yon, et al. Precise gene fusion by PCR. Nucleic Acids Research. 1989; 17(12):4895.
Zaliova, et al. Quantification of fusion transcript reveals a subgroup with distinct biological properties and predicts relapse in BCR/ABL-positive ALL: implications for residual disease monitoring. Leukemia. May 2009;23(5):944-51. Epub Jan. 22, 2009.
Zeng, et al. High-performance single cell genetic analysis using microfluidic emulsion generator arrays. Anal. Chem. 2010; 82:3183-3190.
Zhou, et al. High throughput analysis of TCR-beta rearrangement and gene expression in single cells. 2006; 86:314-321.
Alatrakchi, et al. T-cell clonal in patients with B-cell lymphoproliferative disorders. J Immunother. Sep. 1998;21(5):363-70.
Bruggemann, et al. Standardized MRD quantification in European ALL trials: proceedings of the Second International Symposium on

(56) References Cited

OTHER PUBLICATIONS

MRD assessment in Kiel, Germany, Sep. 18-20, 2008. Leukemia. Mar. 2010;24(3):521-35. doi: 10.1038/leu.2009.268. Epub Dec. 24, 2009.
Chen, A novel approach for the analysis of T-cell reconstitution by using a T-cell receptor beta-based oligonucleotide microarray in hematopoietic stem cell transplantation. Exp Hematol. May 2007;35(5):831-41.
Gerlinger, et al. How Darwinian models inform therapeutic failure initiated by clonal heterogeneity in cancer medicine. Br J Cancer. Oct. 12, 2010;103(8):1139-43. doi: 10.1038/sj.bjc.6605912. Epub Sep. 28, 2010.
Guo, et al. Sequence changes at the V-D junction of the VH1 heavy chain of anti-phosphocholine antibodies alter binding to and protection against *Streptococcus pneumoniae*. Int Immunol May 1997;9(5):665-77.
Howe, et al. T cell receptor clonotype analysis of T cell responses: Diagnostic application of a clonotypic database. Blood. 2003; 102:Abstract 3918.
Office action dated Mar. 13, 2013 for U.S. Appl. No. 13/763,978.
Office action dated Mar. 20, 2013 for U.S. Appl. No. 13/487,980.
Office action dated Apr. 22, 2013 for U.S. Appl. No. 13/214,111.
Office action dated Jun. 6, 2013 for U.S. Appl. No. 13/100,365.
Office action dated Jun. 6, 2013 for U.S. Appl. No. 13/100,389.
Office action dated Jun. 20, 2013 for U.S. Appl. No. 13/214,111.
Office action dated Jul. 5, 2013 for U.S. Appl. No. 13/763,978.
Sfanos, et al. Phenotypic analysis of prostate-infiltrating lymphocytes reveals TH17 and Treg skewing. Clin Cancer Res. Jun. 1, 2008;14(11):3254-61. doi: 10.1158/1078-0432.CCR-07-5164.
Sing, et al. A molecular comparison of T lymphocyte populations infiltrating the liver and circulating in the blood of patients with chronic hepatitis B: evidence for antigen-driven selection of a public complementarity-determining region 3 (CDR3) motif. Hepatology. May 2001;33(5):1288-98.
Szczepanski, et al. Comparative analysis of Ig and TCR gene rearrangements at diagnosis and at relapse of childhood precursor-B-ALL provides improved strategies for selection of stable PCR targets for monitoring of minimal residual disease. Blood. Apr. 1, 2002;99(7):2315-23.
Szczepanski, et al. Why and how to quantify minimal residual disease in acute lymphoblastic leukemia? Leukemia. Apr. 2007;21(4):622-6. Epub Feb. 15, 2007.
UK combined search and examination report dated Mar. 20, 2013 for GB 1300533.5.
Van Der Velden, et al. Analysis of minimal residual disease by Ig/TCR gene rearrangements: guidelines for interpretation of real-time quantitative PCR data. Leukemia. Apr. 2007;21(4):604-11. Epub Feb. 8, 2007.
Van Der Velden, et al. Detection of minimal residual disease in hematologic malignancies by real-time quantitative PCR: principles, approaches, and laboratory aspects. Leukemia. Jun. 2003;17(6):1013-34.
Wu, et al. High-throughput sequencing detects minimal residual disease in acute T lymphoblastic leukemia. Sci Transl Med. May 16, 2012;4(134):134ra63. doi: 10.1126/scitranslmed.3003656.
PCT/US2014/061260, Appln filed Oct. 17, 2014, Faham et al.
Drossman, et al. High-speed separations of DNA sequencing reactions by capillary electrophoresis. Anal Chem. May 1, 1990;62(9):900-3.
Office action dated Nov. 20, 2014 for U.S. Appl. No. 13/214,111.
Andreasson, et al. The human IgE-encoding transcriptome to assess antibody repertoires and repertoire evolution. J Mol Biol. Sep. 15, 2006;362(2):212-27. Epub Aug. 14, 2006.
Office action dated Oct. 7, 2013 for U.S. Appl. No. 13/459,701.
Office action dated Oct. 16, 2013 for U.S. Appl. No. 13/487,980.
Office action dated Nov. 6, 2013 for U.S. Appl. No. 13/468,323.
Office action dated Nov. 27, 2013 for U.S. Appl. No. 13/196,885.
U.S. Appl. No. 61/112,693, filed Nov. 7, 2008, Faham et al.
Abath, et al. Single-tube nested PCR using immobilized internal primers. Biotechniques. Dec. 2002;33(6):1210-2, 1214.
Altin, et al. The role of CD45 and CD45-associated molecules in T cell activation. Immunol Cell Biol. Oct. 1997;75(5):430-45.
Arnaout. Specificity and overlap in gene segment-defined antibody repertoires. C Genomics. Oct. 28, 2005;6:148.
Damle, et al. B-cell chronic lymphocytic leukemia cells express a surface membrane phenotype of activated, antigen-experienced B lymphocytes. Blood. Jun. 1, 2002;99(11):4087-93.
De Bona, et al. Optimal spliced alignments of short sequence reads. Bioinformatics. Aug. 15, 2008;24(16):i174-80. doi: 10.1093/bioinformatics/btn300.
Diluvio, et al. Identical TCR beta-chain rearrangements in streptococcal angina and skin lesions of patients with psoriasis vulgaris. J Immunol. Jun. 1, 2006;176(11):7104-11.
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Droege, et al. The Genome Sequencer FLX System—longer reads, more applications, straight forward bioinformatics and more complete data sets. J Biotechnol. Aug. 31, 2008;136(1-2):3-10. doi: 10.1016/j.jbiotec.2008.03.021. Epub Jun. 21, 2008.
Eisenstein. Personalized, sequencing-based immune profiling spurs startups. Nat Biotechnol. Mar. 2013;31(3):184-6. doi: 10.1038/nbt0313-184b.
Erlich, et al. Alta-Cyclic: a self-optimizing base caller for next-generation sequencing. Nat Methods. Aug. 2008;5(8):679-82. doi: 10.1038/nmeth.1230. Epub Jul. 6, 2008.
European opposition dated Oct. 14, 2014 for EP Application No. 09764971.1.
European opposition dated Oct. 15, 2014 for EP Application No. 09764971.1. (in French only).
Furmanski, et al. Public T cell receptor beta-chains are not advantaged during positive selection. J Immunol. Jan. 15, 2008;180(2):1029-39.
Giga—Roche 454 FLX technology how it works. Fiche technique du Centre Interdisciplinaire de Genoproteomique Appliquee (Universite de Liege, Belgique). Accessed Oct. 15, 2014.
Gomes, et al. Single-tube nested PCR using immobilized internal primers for the identification of dengue virus serotypes. J Virol Methods. Oct. 2007;145(1):76-9. Epub Jun. 15, 2007.
Gupta. Single-molecule DNA sequencing technologies for future genomics research. Trends Biotechnol. Nov. 2008;26(11):602-11. doi: 10.1016/j.tibtech.2008.07.003. Epub Aug. 21, 2008.
Heger. Roche's 454 Eyes Immune Repertoire Sequencing as Key Application for Long-Read Platform. Feb. 2, 2010. http://www.genomeweb.com/print/932624.
IlluminA Systems & Software, Technology Spotlight, DNA Sequencing with Solexa® Technology, Illumina, Inc., Pub. No. 770-2007-002, 2007.
Jurkat, Clone 6-1 (ATCC TIB-152) Webpage retrievable from the ATCC under http://www.lgcstandards-atcc.org/Products/A11MB-152.aspx#characteristics. Accessed Oct. 14, 2014.
Lin, et al. Multiplex genotype determination at a large number of gene loci. Proc Natl Acad Sci U S A. Mar. 19, 1996;93(6):2582-7.
Lowe, et al. A computer program for selection of oligonucleotide primers for polymerase chain reactions. Nucleic Acids Res. Apr. 11, 1990;18(7):1757-61.
Mardis. Next-generation DNA sequencing methods. Annu Rev Genomics Hum Genet. 2008;9:387-402. doi: 10.1146/annurev.genom.9.081307.164359.
Miceli, et al. The roles of CD4 and CD8 in T cell activation. Semin Immunol. May 1991;3(3):133-41. Abstract only.
Office action dated May 2, 2011 for U.S. Appl. No. 12/425,310.
Office action dated May 8, 2014 for U.S. Appl. No. 12/425,310.
Office action dated Aug. 6, 2010 for U.S. Appl. No. 12/425,310.
Quick. SOLiD System—a next-gen DNA sequencing platform announced, Gizmag online magazine, http://www.mizmag.com/go/8248, pp. 1-5, Oct. 2007.
Robins. Immunosequencing: applications of immune repertoire deep sequencing. Curr Opin Immunol. Oct. 2013;25(5):646-52. doi: 10.1016/j.coi.2013.09.017. Epub Oct. 16, 2013.

(56) References Cited

OTHER PUBLICATIONS

Sequenta and iRepertoire Join Forces on Blood Cancer Testing. BusinessWire. Aug. 8, 2013. http://www.businesswire.com/news/home/20130808005363/en/Sequenta-iRepertoire-Join-Forces-Blo...#.VGTT9Wd0yUk.
Shendure, et al. Advanced sequencing technologies: methods and goals. Nat Rev Genet. May 2004;5(5):335-44.
Shendure, et al. Next-generation DNA sequencing. Nat Biotechnol. Oct. 2008;26(10):1135-45. doi: 10.1038/nbt1486.
Stanley. Essentials of Immunology & Serology, Delmar, Thomson Learning, Chapter 7, T cells, p. 95, 2002.
Striebich, et al. Selective accumulation of related CD4+ T cell clones in the synovial fluid of patients with rheumatoid arthritis. J Immunol. Oct. 15, 1998;161(8):4428-36.
Supplemental material of Weinstein, et al. High-throughput sequencing of the zebrafish antibody repertoire. Science. May 8, 2009;324(5928):807-10. doi: 10.1126/science.1170020. www.sciencemag.org/cgi/content/full/324/5928/807/DC1.
Vanderborght, et al. Dynamic T cell receptor clonotype changes in synovial tissue of patients with early rheumatoid arthritis: effects of treatment with cyclosporin A (Neoral). J Rheumatol. Mar. 2002;29(3):416-26.
Wang, et al. HIV integration site selection: analysis by massively parallel.pyrosequencing reveals association with epigenetic modifications. Genome Res. Aug. 2007;17(8):1186-94. Epub Jun. 1, 2007.
U.S. Appl. No. 14/075,075, filed Nov. 8, 2013, Faham et al.
U.S. Appl. No. 14/404,435, filed Nov. 26, 2014, Faham et al.
Bertness, et al. T-cell receptor gene rearrangements as clinical markers of human T-cell lymphomas. N Engl J Med. Aug. 29, 1985;313(9):534-8.
Qu, et al. Efficient frequency-based de novo short-read clustering for error trimming in next-generation sequencing. Genome Res. Jul. 2009;19(7):1309-15. doi: 10.1101/gr.089151.108. Epub May 13, 2009.
Weiss, et al. Clonal rearrangements of T-cell receptor genes in mycosis fungoides and dermatopathic lymphadenopathy. N Engl J Med. Aug. 29, 1985;313(9):539-44.
U.S. Appl. No. 14/317,087, filed Jun. 27, 2014, Asbury et al.
PCT/US2014/044971, Appln filed Jun. 30, 2014, Asbury et al.
PCT/US2014/047909, Appln filed Jul. 31, 2014, Klinger et al.
U.S. Appl. No. 14/363,276, filed Jun. 5, 2014, Faham et al.
U.S. Appl. No. 14/363,956, filed Jun. 9, 2014, Faham et al.
U.S. Appl. No. 14/364,961, filed Jun. 12, 2014, Faham et al.
U.S. Appl. No. 14/366,840, filed Jun. 19, 2014, Faham.
U.S. Appl. No. 14/383,101, filed Sep. 4, 2014, Faham et al.
U.S. Appl. No. 14/383,102, filed Sep. 4, 2014, Faham.
Nie, et al. Optical detection of single molecules. Annu Rev Biophys Biomol Struct. 1997;26:567-96.
Office action dated Aug. 26, 2014 for U.S. Appl. No. 14/075,075.
Notice of allowance dated Sep. 12, 2014 for U.S. Appl. No. 13/214,111.
Office action dated Oct. 8, 2014 for U.S. Appl. No. 13/459,701.
PCT/US2013/065493, Appln filed Oct. 17, 2013, Faham et al.
PCT/US2013/065509, Appln filed Oct. 17, 2013, Faham et al.
PCT/US2013/065757, Appln filed Oct. 18, 2013, Faham et al.
PCT/US2014/017416, Appln filed Feb. 20, 2014, Pepin et al.
U.S. Appl. No. 12/615,263, filed Nov. 9, 2011, Faham et al.
U.S. Appl. No. 13/100,365, filed May 4, 2011, Faham et al.
U.S. Appl. No. 13/100,389, filed May 4, 2011, Faham et al.
U.S. Appl. No. 13/100,395, filed May 4, 2011, Faham et al.
U.S. Appl. No. 13/214,111, filed Aug. 19, 2011, Faham et al.
U.S. Appl. No. 13/459,701, filed Apr. 30, 2012, Faham et al.
U.S. Appl. No. 13/468,323, filed May 10, 2012, Faham et al.
U.S. Appl. No. 13/596,581, filed Aug. 28, 2012, Zheng et al.
U.S. Appl. No. 13/688,414, filed Nov. 29, 2012, Faham et al.
U.S. Appl. No. 13/763,978, filed Feb. 11, 2013, Faham et al.
U.S. Appl. No. 13/834,794, filed Mar. 15, 2013, Pepin et al.
U.S. Appl. No. 13/835,093, filed Mar. 15, 2013, Faham et al.
U.S. Appl. No. 13/859,210, filed Apr. 9, 2013, Asbury et al.
U.S. Appl. No. 14/089,517, filed Nov. 25, 2013, Han.
U.S. Appl. No. 14/185,846, filed Feb. 20, 2014, Pepin et al.
U.S. Appl. No. 14/197,615, filed Mar. 5, 2014, Carlton et al.
U.S. Appl. No. 14/202,990, filed Mar. 10, 2014, Zheng.
U.S. Appl. No. 14/242,520, filed Apr. 1, 2014, Klinger et al.
U.S. Appl. No. 14/343,286, filed Mar. 6, 2014, Faham et al.
European search report and opinion dated Mar. 13, 2014 for EP Application No. 13195379.6.
European search report and opinion dated Jul. 26, 2013 for EP Application No. 11777704.5.
Greenberg, et al. Profile of immunoglobulin heavy chain variable gene repertoires and highly selective detection of malignant clonotypes in acute lymphoblastic leukemia. J Leukoc Biol. Jun. 1995;57(6):856-64.
International preliminary report on patentability dated May 19, 2011 for PCT/US2009/006053.
Notice of allowance dated Jan. 27, 2014 for U.S. Appl. No. 13/100,365.
Notice of allowance dated Feb. 21, 2014 for U.S. Appl. No. 13/468,323.
Notice of allowance dated Mar. 14, 2012 for U.S. Appl. No. 12/615,263.
Notice of allowance dated Aug. 30, 2013 for U.S. Appl. No. 13/763,978.
Notice of allowance dated Nov. 6, 2013 for U.S. Appl. No. 13/100,389.
Notice of allowance dated Dec. 5, 2013 for U.S. Appl. No. 13/214,111.
Office action dated Apr. 4, 2014 for U.S. Appl. No. 13/459,701.
Thor Straten, et al. T-cell clonotypes in cancer.J Transl Med. Apr. 8, 2004;2(1):11.
U.S. Appl. No. 14/436,851, filed Apr. 17, 2015, Klinger et al.
U.S. Appl. No. 14/436,855, filed Apr. 17, 2015, Carlton et al.
U.S. Appl. No. 14/437,470, filed Apr. 21, 2015, Faham.
Office action dated May 8, 2015 for U.S. Appl. No. 14/242,299.
U.S. Appl. No. 14/329,873, filed Jul. 11, 2014, Faham et al.
U.S. Appl. No. 14/350,516, filed Apr. 8, 2014, Faham et al.
U.S. Appl. No. 14/350,785, filed Apr. 9, 2014, Faham et al.
Kou, et al. T-Cell receptor Vbeta repertoire CDR3 length diversity differs within CD45RA and CD45RO T-cell subsets in healthy and human immunodeficiency virus-infected children. Clin Diagn Lab Immunol. Nov. 2000;7(6):953-9.
Miqeu, et al. Statistical analysis of CDR3 length distributions for the assessment of T and B cell repertoire biases. Mol Immunol. Feb. 2007;44(6):1057-64. Epub Aug. 22, 2006.
Office action dated May 16, 2014 for U.S. Appl. No. 13/196,885.
Notice of allowance dated Dec. 15, 2014 for U.S. Appl. No. 13/196,885.
Office action dated Dec. 10, 2014 for U.S. Appl. No. 14/329,873.
Office action dated May 22, 2015 for U.S. Appl. No. 14/243,875.
Office action dated May 22, 2015 for U.S. Appl. No. 14/329,873.
Office action dated Jul. 17, 2015 for U.S. Appl. No. 14/075,075.
Xu, et al. Simultaneous isolation of DNA and RNA from the same cell population obtained by laser capture microdissection for genome and transcriptome profiling. J Mol Diagn. Mar. 2008;10(2):129-34. doi: 10.2353/jmoldx.2008.070131. Epub Feb. 7, 2008.
Han, et al. Immunorepertoire analysis by multiplex PCR amplification and high throughput sequencing, J. of Immunol., vol. 182, Apr. 15, 2009, Abstract.
Wang, et al. Immunorepertoire analysis by multiplex PCR amplification and high throughput sequencing. Poster-Program 42.6, The 96th Annual Meeting of the America Association of Immunologists, Seattle, USA. May 8-12, 2009.
Office action dated Jul. 8, 2015 for U.S. Appl. No. 14/176,551.
Office action dated Jun. 19, 2015 for U.S. Appl. No. 13/905,406.
Office action dated Aug. 11, 2014 for U.S. Appl. No. 13/196,885.
Abbott, et al. "Design and use of signature primers to detect carry-over of amplified material", *J Virol Methods*, 46(1):51-59, Abstract Only (1994).
Ahmadzadeh et al. "FOXP3 expression accurately defines the population of intratumoral regulatory T cells that selectively accumulate in metastatic melanoma lesions", *Blood*, 112(13): 4953-4960 (2008).
Altman, et al. "Phenotypic analysis of antigen-specific T lymphocytes", The *Journal of Immunology*, 187(1):7-9 (2011).

(56) References Cited

OTHER PUBLICATIONS

Altschul, et al. "Basic local alignment search tool", *J Mol Biol.*, 215(3):403-410 (1990).
Arden, et al. "Human T-cell receptor variable gene segment families", *Immunogenetics*, 42(6):455-500, Abstract Only (1995).
Armand, P. et al., "Detection of circulating tumour DNA in patients with aggressive B-cell non-Hodgkin lymphoma", *Brit. J. Haematol.*, vol. 163, pp. 123-126 (2013).
Aslanzadeh. "Preventing PCR amplification carryover contamination in a clinical laboratory", *Ann Clin Lab Sci.*, 34(4):389-396 (2004).
Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", *Blood*, 96(2): 640-646 (2000).
Ateya, et al. "The good, the bad, and the tiny: a review of microflow cytometry", *Anal Bioanal Chem.*, 391(5): 1485-1498 (2008). doi: 10.1007/s00216-007-1827-5. Epub Jan. 29, 2008.
Babrzadeh et al. "Development on High-throughput Sequencing Technology: emPCR Titration and Barcode Design", Stanford School of Medicine, 2 pages (2011).
Baldauf, "Phylogeny for the faint of heart: a tutorial," Trends in Genetics, 19(6): 345-351 (2003).
Barbas, et al. "Assembly of combinatorial antibody libraries on phage surfaces: the gene III site", *PNAS*, 88(18): 7978-7982, Abstract Only (1991).
Barker, et al. "A second type II restriction endonuclease from Thermus aquaticus with an unusual sequence specificity", *Nucleic Acids Res.*, 12(14): 5567-5581 (1984).
Baum and McCune et al. "Direct measurement of T-cell receptor repertoire diversity with AmpliCot", *Nat Methods*, 3(11): 895-901 (2006).
Becker-André and Hahlbrock. "Absolute mRNA quantification using the polymerase chain reaction (PCR). A novel approach by a PCR aided transcript titration assay (PATTY)", *Nucleic Acids Res.*, 17(22): 9437-9446 (1989).
Becton-Dickinson, CD marker handbook. bdbiosciences.com/go/mousecdmarkers, p. 1-47 (2010).
Becton-Dickinson T-Cell Research Tools, "Novel multicolor flow cytometry tools for the study of CD4+ T-cell differentiation and plasticity", 16 pages (2009).
Ben-Ezra, et al. Effect of fixation on the amplification of nucleic acids from paraffin-embedded material by the polymerase chain reaction, *The Journal of Histochemistry and Cytochemistry*, 39(3): 351-354 (1991).
Benecke. "DNA typing in forensic medicine and in criminal investigations: a current survey", *Naturwissenschaften*, 84(5): 181-188 (1997).
Benichou, J. et al., "The restricted DH gene reading frame usage in the expressed human antibody repertoire is selected based upon its amino acid content", J Immunol., 190(11): 5567-77, 29 pages (2013).
Bentley, et al. "Accurate whole human genome sequencing using reversible terminator chemistry", *Nature*, 456(7218):53-59 (2008). doi: 10.1038/nature07517.
Bereczki, et al. "Optimization of PCR amplification for B- and T-cell clonality analysis on formalin-fixed and paraffin-embedded samples", *Pathology Oncology Research*, 13(3): 209-214 (2007). Epub Oct. 7, 2007.
Berger, et al. "The clonotypic T cell receptor is a source of tumor-associated antigens in cutaneous T cell lymphoma", *Annals of the New York Academy of Sciences*, 941:106-122, Abstract Only (2001).
Berget, et al. "Detection of clonality in follicular lymphoma using formalin-fixed, paraffin-embedded tissue samples and BIOMED-2 immunoglobulin primers", J Clin Pathol., 64(1):37-41 (2011). doi: 10.1136/jcp.2010.081109. Epub Oct. 28, 2010.
Bernard et al. "Color multiplexing hybridization probes using the apolipoprotein E locus as a model system for genotyping", Anal Biochem., 273(2):221-228 (1999).
Berquam-Vrieze, K. et al., "Cell of origin strongly influences genetic selection in a mouse model of T-ALL", *Blood*, 118:4646-4656 (2011).
Berzofsky, et al. "Progress on new vaccine strategies for the immunotherapy and prevention of cancer", *J Clin Invest.*, 113(11): 1515-1525 (2004).
Biagi, et al. "Responses to human CD40 ligand/human interleukin-2 autologo cell vaccine in patients with B-cell chronic lymphocytic leukemia", *Clin Cancer Res.*, 11(19 Pt 1): 6916-6923 (2005).
Biggerstaff, et al. "Enumeration of leukocyte infiltration in solid tumors by confocal laser scanning microscopy", *BMC Immunol.*, 7:16, 13 pages (2006).
Brochet et al. "IMGT/V-QUEST: the highly customized and integrated system for IG and TR standardized V-J and V-D-J sequence analysis", *Nucleic Acids Research*, vol. 36, Web Server issue W503-W508 (2008).
Bolotin, D.A. et al., "Next generation sequencing for TCR repertoire profiling: Platform-specific features and correction algorithms", *Eur. J. Immunol.*, 42:3073-3083 (2012).
Bonner et al. "Fluorescence activated cell sorting", Rev Sci Instrum., 43(3):404-409, Abstract Only (1972).
Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.
Boudinot et al. "New perspectives for large-scale repertoire analysis of immune receptors", *Molecular Immunology*, 45: 2437-2445 (2008).
Bousso. "Generation of MHC-peptide tetramers: a new opportunity for dissecting T-cell immune responses", Microbes Infect., 2(4):425-429, Abstract Only (2000).
Boyce, et al. "Human regulatory T-cell isolation and measurement of function", *BD Biosciences*, pp. 1-20 (2010).
Bravo and Irizarry. "Model-Based Quality Assessment and Base-Calling for Second-Generation Sequencing Data", Biometrics, 66(3): 665-674 (2010).
Brenner, et al. "In vitro cloning of complex mixtures of DNA on microbeads: physical separation of differentially expressed cDNAs", *PNAS*, 97(4): 1665-1670 (2000).
Brentjens, et al. "CD19-targeted T cells rapidly induce molecular remissions in adults with chemotherapy-refractory acute lymphoblastic leukemia", Sci Transl Med., 5(177): 177ra38 (2013). doi: 10.1126/scitranslmed.3005930.
Brisco, et al. "Outcome prediction in childhood acute lymphoblastic leukaemia by molecular quantification of residual disease at the end of induction", *Lancet*, 343:196-200 (1994).
Brockman et al, "Quality scores and SNP detection in sequencing-by-synthesis systems," Genome Research, 18: 763-770 (2008).
Brody, et al. "Active and passive immunotherapy for lymphoma: proving principles and improving results", J Clin Oncol., 29(14):1864-1875, Abstract Only (2011). doi: 10.1200/JCO.2010. 33.4623. Epub Apr. 11, 2011.
Brody, et al., "Immunotransplant for mantle cell lymphoma: Phase I/II study preliminary results", *Journal of Clinical Oncology*, ASCO Annual Meeting Abstracts Part 1, vol. 29, No. 15, 1 page (2011).
Brody, et al. "Lymphoma immunotherapy: vaccines, adoptive cell transfer and immunotransplant", *Immunotherapy*, 1(5): 809-824 (2009). doi: 10.2217/imt.09.50.
Brown, et al. "Current techniques for single-cell lysis", *J. R. Soc. Interface*, 5:S131-S138 (2008).
Brownie et al. "The elimination of primer-dimer accumulation in PCR", Nucleic Acids Research, 25(16): 3235-3241 (1997).
Brüggemann, et al. "Rearranged T-cell receptor beta genes represent powerful targets for quantification of minimal residual disease in childhood and adult T-cell acute lymphoblastic leukemia", *Leukemia*, 18(4): 709-719 (2004).
Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.
Buccisano, et al. "Monitoring of minimal residual disease in acute myeloid leukemia", Curr Opin Oncol., 21(6):582-588, Abstract Only (2009). doi: 10.1097/CCO.0b013e3283311856.

(56) References Cited

OTHER PUBLICATIONS

Butkus, B. "Hutch Team Uses ddPCR to Quantify T-Cell Response in Tumors; Adaptive Biotech Eyes Market", *PCR Insider*, Dec. 12, 2013, 3 pages http://www.genomeweb.com/print/1323296.

Bystrykh. "Generalized DNA Barcode Design Based on Hamming Codes", *PLoS ONE*, 7(5): e36852, 1-8 (2012).

Campana, et al. "Role of minimal residual disease monitoring in adult and pediatric acute lymphoblastic leukemia", *Hematol Oncol Clin North Am.*, 23(5): 1083-1098 (2009). doi: 10.1016/j.hoc.2009.07.010.

Carlotti, et al. "Transformation of follicular lymphoma to diffuse large B-cell lymphoma may occur by divergent evolution from a common progenitor cell or by direct evolution from the follicular lymphoma clone", *Blood*, 113(15): 3553-3557 (2009). doi: 10.1182/blood-2008-08-174839. Epub Feb. 6, 2009.

Carlson, et al. "Immune Profiling Suggests an IGH Signaling-Dependent Subtype of Aggressive B-ALL", *Blood*, 120: 1428, Abstract (2012).

Carlson, et al. "Deep sequencing of the human TCRγ and TCRβ repertoires provides evidence that TCRβ rearranges after αβ, γδT cell commitment". Presented at the ASHG 2011 Conference. Oct. 2011. Poster. 1 page.

Carlson, et al. "Detection of tumor tagging clones in multiple myeloma via high throughput sequencing is robust to significant levels of SHM", Presented for the 2014 ASH Annual Meeting. Poster, 1 page. Dec. 5-9, 2014.

Carlson, C.S. et al. "Using synthetic templates to design an unbiased multiplex PCR assay", *Nature Communications*, 4:2680, pp. 1-9 (2013).

Casali, et al. "Human monoclonals from antigen-specific selection of B lymphocytes and transformation by EBV", *Science*, 234(4775): 476-479, Abstract Only (1986).

Casbon et al. "A method for counting PCR template molecules with application to next-generation sequencing", *Nucleic Acids Research*, 39(12): e81, 8 pages (2011).

Catherwood, M.A. et al., "Improved clonality assessment in germinal centre/post germinal centre non-Hodgkin's lymphomas with high rates of somatic hypermutation", *J. Clin. Pathol.*, 60:524-528, Abstract (2007).

Chan et al. "Evaluation of Nanofluidics Technology for High-Throughput SNP Genotyping in a Clinical Setting", *The Journal of Molecular Diagnostics*, 13(3): 305-312 (2011).

Chattopadhyay, et al. "A live-cell assay to detect antigen-specific CD4+ T cells with diverse cytokine profiles", *Nat Med.*, 11(10): 1113-1117 (2005). Epub Sep. 25, 2005.

Chen et al. "Identification of racehorse and sample contamination by novel 24-plex STR system", Forensic Science International: Genetics, 4:158-167 (2010).

Chen, et al. "Microfluidic cell sorter with integrated piezoelectric actuator", *Biomed Microdevices*, 11(6): 1223-1231 (2009). doi: 10.1007/s10544-009-9341-5.

Chen, Y. et al., "T-cell receptor gene expression in tumour-infiltrating lymphocytes and peripheral blood lymphocytes of patients with nasopharyngeal carcinoma", *British Journal of Cancer*, 72(1): 117-22 (1995).

Chen, et al. "Total Gene Synthesis: Novel Single-Step and Convergent Strategies Applied to the Construction of a 779 Base Pair Bacteriorhodopsis", *Gene. J. Am. Chem Soc.*, 116: 8799-8800, Abstract Only (1994).

Chiu, et al. "Non-invasive prenatal assessment of trisomy 21 by multiplexed maternal plasma DNA sequencing: large scale validity study", *BMJ*, 342:c7401, 9 pages (2011). doi: 10.1136/bmj.c7401.

Churchill and Waterman. "The Accuracy of DNA Sequences: Estimating Sequence Quality", *Genomics*, 14:89-98 (1992).

Chute, et al. "Detection of immunoglobulin heavy chain gene rearrangements in classic hodgkin lymphoma using commercially available BIOMED-2 primers", *Diagn Mol Pathol.*, 17(2): 65-72 (2008). doi: 10.1097/PDM.0b013e318150d695.

Citri et al. "Comprehensive qPCR profiling of gene expression in single neuronal cells", *Nature Protocols*, 7(1): 118-127 (2012).

Cleary, et al. "Production of complex nucleic acid libraries using highly parallel in situ oligonucleotide synthesis", *Nat Methods*, 1(3): 241-248 (2004). Epub Nov. 18, 2004.

Clemente, et al. "Deep sequencing of the T-cell receptor repertoire in CD8+ T-large granular lymphocyte leukemia identifies signature landscapes", Blood, 122(25): 4077-85 (2013). doi: 10.1182/blood-2013-05-506386. Epub Oct. 22, 2013.

Cooper, et al. "BRAF inhibition is associated with increased clonality in tumorinfiltrating lymphocytes", Oncoimmunology, 2(10):e26615 (2013). Epub Oct. 15, 2013.

Craig et al. "Identification of genetic variants using bar-coded multiplex sequencing", *Nature Methods*, 5(10): 887-893 (2008) and Supplemental Materials.

Cronin, et al. "Comprehensive next-generation cancer genome sequencing in the era of targeted therapy and personalized oncology", *Biomark Med.*, 5(3):293-305 (2011). (Abstract only). doi: 10.2217/bmm.11.37.

Dahl et al. "Multiplex amplification enabled by selective circularization of large sets of genomic DNA fragments", Nucleic Acids Res., 33(8): e71 (2005).

Davila, et al. Efficacy and toxicity management of 19-28z CART cell therapy in B cell acute lymphoblastic leukemia, Sci Transl Med., 6(224):224ra25 (2014). doi: 10.1126/scitranslmed.3008226.

Davis, et al. "Interrogating the repertoire: broadening the scope of peptide-MHC multimer analysis", *Nat Rev Immunol.*, 11(8):551-558 (2011). doi: 10.1038/nri3020.

Dean, et al. "Rapid amplification of plasmid and phage DNA using Phi 29 DNA polymerase and multiply-primed rolling circle amplification", *Genome Res.*, 11(6): 1095-1099 (2001).

Decoste et al. "Relative and Absolute Quantitative Real-Time PCR-Based Quantifications of hcnC and phlD Gene Transcripts in Natural Soil Spiked with *Pseudomonas* sp. Strain LBUM300", *Applied and Environmental Microbiology*, 77(1): 41-47 (2011).

Dedhia, et al. "Evaluation of DNA extraction methods and real time PCR optimization on formalin-fixed paraffin-embedded tissues", *Asian Pac J Cancer Prev.*, 8(1): 55-59 (2007).

Deiman, et al. "Characteristics and applications of nucleic acid sequence-based amplification (NASBA)", *Mol Biotechnol.*, 20(2): 163-179, Abstract Only (2002).

DeKosky et al. "High-throughput sequencing of the paired human immunoglobulin heavy and light chain repertoire", *Nature Biotechnology*, 31(2): 166-169 (2013).

Delaney, et al. "Evolution and Clinical Implications of the T cell Repertoire Following Cord Blood Transplant", Biology of Blood and Marrow Transplant, vol. 19, Issue 2, S201-S202. Published Feb. 2013.

Deschoolmeester, et al. "Tumor infiltrating lymphocytes: an intriguing player in the survival of colorectal cancer patients", *BMC Immunology*, 11:19, 12 pages (2010). doi: 10.1186/1471-2172-11-19.

Desmarais, et al. High-throughput sequencing of memory and naïve T cell receptor repertoires at the RNA and DNA levels reveals differences in relative expression of expanded TCR clones. Adaptive Technologies. Seattle W A. Poster, 1 page. Presented May 5, 2012.

Desmarais and Robins. "High-throughput sequencing of memory and naïve T cell receptor repertoires at the RNA and DNA levels reveals differences in relative expression of expanded TCR clones", The Journal of Immunology, 188: 178.12 (2012).

Dictor et al. "Resolving T-cell receptor clonality in two and genotype in four multiplex polymerase chain reactions", *Haematologica*, 90(11): 1524-1532 (2005).

Diederichsen, et al. "Prognostic value of the CD4+/CD8+ ratio of tumour infiltrating lymphocytes in colorectal cancer and HLA-DR expression on tumour cells", *Cancer Immunol Immunother.*, 52(7):423-428 (2003). Epub Apr. 15, 2003.

Diehl, et al. "BEAMing: single-molecule PCR on microparticles in water-in-oil emulsions", *Nat Methods*, 3(7):551-559, Abstract Only (2006).

Ding, et al. "Clonal evolution in relapsed acute myeloid leukaemia revealed by whole-genome sequencing", *Nature*, 481(7382):506-510 (2012). doi: 10.1038/nature10738.

Diviacco, et al. "A novel procedure for quantitative polymerase chain reaction by coamplification of competitive templates", *Gene*, 122(2):313-320 (1992).

(56) References Cited

OTHER PUBLICATIONS

Do and Batzoglou. "What is the expectation maximization algorithm?", *Nature Biotechnology*, 26(8): 897-899 (2008).
Dobosy, J. et al. "RNase H-dependent PCR (rhPCR): improved specificity and single nucleotide polymorphism detection using blocked cleavable primers", *BMC Biotechnology*, 11(80):1-18 (2011).
Drmanac, et al. "Human genome sequencing using unchained base reads on self-assembling DNA nanoarrays", *Science*, 327(5961):78-81 (2010). doi: 10.1126/science.1181498. Epub Nov. 5, 2009.
Dudgeon, et al. "The evolution of thymic lymphomas in p53 knockout mice", Genes Dev., 28(23): 2613-20 (2014). doi: 10.1101/gad.252148.114.
Dunn, et al. "Focus on TILs: Prognostic significance of tumor infiltrating lymphocytes in human glioma", *Cancer Immun.*, 7:12, 16 pages (2007).
Eason et al. "Characterization of synthetic DNA bar codes in *Saccharomyces cerevisiae* gene-deletion strains," *PNAS*, 101(30): 11046-11051 (2004).
Eichler, et al. "Haplotype and interspersion analysis of the FMR1 CGG repeat identifies two different mutational pathways for the origin of the fragile X syndrome", *Hum Mol Genet.*, 5(3):319-330 (1996).
Eichler, et al. "Length of uninterrupted CGG repeats determines instability in the FMR1 gene", *Nat Genet.*, 8(1):88-94, Abstract Only (1994).
Eid et al. "Real-time DNA sequencing from single polymerase molecules", *Science*, 323(5910):133-138 (2009). doi: 10.1126/science.1162986. Epub Nov. 20, 2008.
Eis, et al. "An invasive cleavage assay for direct quantitation of specific RNAs", *Nat Biotechnol.*, 19(7):673-676, Abstract Only (2001).
Elkord et al. "T regulatory cells in cancer: recent advances and therapeutic potential", *Expert Opinion on Biological Therapy*, 10(11): 1573-1586 (2010).
Emerson, et al. "Correlation of TCR diversity with immune reconstitution after cord blood transplant", Presented at the American Society of Clinical Oncology's annual meeting. May 2012. Poster. 1 page.
Emerson, R.O. et al. "High-throughput sequencing of T-cell receptors reveals a homogeneous repertoire of tumour-infiltrating lymphocytes in ovarian cancer", *Journal of Pathology*, 231: 433-440 (2013).
Emerson, et al. "CD4+ and CD8+ T cell β antigen receptors have different and predictable V and J gene usage and CDR3 lengths", Presented at the Annual Meeting of the American Association of Immunologists in Boston, MA May 2012. Poster.
Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.
Emerson, et al. TCR repertoire diversity assessed with immunosequencing is associated with patient mortality following cord blood transplant. Presented for the 2014 ASH Annual Meeting. Poster. 1 page. Dec. 5-9, 2014.
Estorninho, et al. "A novel approach to tracking antigen-experienced CD4 T cells into functional compartments via tandem deep and shallow TCR clonotyping", J Immunol., 191(11): 5430-40 (2013). doi: 10.4049/jimmunol.I300622. Epub Oct. 25, 2013.
EP Application No. 09764927.1, Notice of Opposition dated Oct. 14, 2014.
EP Application No. 09764927.1, European Opposition dated Oct. 15, 2014 (in French only).
Esendagli et al. "Malignant and non-malignant lung tissue areas are differentially populated by natural killer cells and regulatory T cells in non-small cell lung cancer", Lung Cancer, 59(1): 32-40 (2008).
European Patent Application No. 09764927.1, EPO's Communication of Notices of Opposition, dated Nov. 21, 2014.
European Patent Application No. 09764927.1, Patentee's Observations/Response dated May 27, 2015.
European Patent Application No. 09764927.1, Opponent's Response to Submission of the Patentee dated. Nov. 23, 2015.

Ewing and Green, "Base-calling of automated sequencer traces using Phred. I. Accuracy Assessment," Genome Research, 8: 175-185 (1998).
Faham, M. et al. "Deep-sequencing approach for minimal residual disease detection in acute lymphoblastic leukemia", *Blood,* 120(26): 5173-5180 (2012).
Felsenstein, et al. "Evolutionary Trees from DNA Sequences: A Maximum Likelihood Approach", J Mol. Evol, 17:368-376 (1981).
Ferradini et al. "Analysis of T Cell Receptor Variability in Tumor-infiltrating Lymphocytes from a Human Regressive Melanoma", *J. Clin. Invest.*, pp. 1183-1190 (1993).
Ferrero, et al. "Multiple myeloma shows no intra-disease clustering of immunoglobulin heavy chain genes", *Haematologica*, 97(6): 849-853 (2012). doi: 10.3324/haematol.2011.052852. Epub Dec. 29, 2011.
Fisher et al. "The Relation Between the No. Of Species and the Number of Individuals in a Random Sample of an Animal Population", *Journal of Animal Ecology*, 12(1): 42-58 (1943).
Flaherty et al. "Ultrasensitive detection of rare mutations using next-generation targeted resequencing", *Nucleic Acids Research*, 40(1): e2, 12 pages (2012).
Flicek and Birney, "Sense from sequence reads: methods for alignment and assembly," Nature Methods Supplement, 6(11s): S6-S12 (2009).
Frampton, et al. "Development and validation of a clinical cancer genomic profiling test based on massively parallel DNA sequencing", *Nat Biotechnol.*, 31(11): 1023-1031 (2013). doi: 10.1038/nbt.2696. Epub Oct. 20, 2013.
Frank. "BARCRAWL and BARTAB: software tools for the design and implementation of barcoded primers for highly multiplexed DNA sequencing," *BMC Bioinformatics*, 10: 362 (2009).
Frederiksson et al., "Multiplex amplification of all coding sequences within 10 cancer genes by Gene-Collector", Nucleic Acids Research, 35(7): e47 (2007).
Freeman, et al. "Quantitative RT-PCR: Pitfalls and Potential", *Biotechniques*, 6(1): 112-125 (1999).
Fridman, et al. "Prognostic and predictive impact of intra- and peritumoral immune infiltrates", *Cancer Research*, 71(17): 5601-5605 (2011). doi: 10.1158/0008-5472.CAN-11-1316. Epub Aug. 16, 2011.
Fu et al. "Counting individual DNA molecules by the stochastic attachment of diverse labels", *PNAS*, 108(22): 9026-9031 and Supporting Materials, 8 pages (2011).
Fuller, et al. "The challenges of sequencing by synthesis", *Nat Biotechnol.*, 7(11): 1013-23 (2009) (Abstract only). doi: 10.1038/nbt.1585. Epub Nov. 6, 2009.
Gauss, et al. "Mechanistic constraints on diversity in human V(D)J recombination", *Mol Cell Biol.*, 16(1):258-269 (1996).
Gawad, et al. "Massive evolution of the immunoglobulin heavy chain loc in children with B precursor acute lymphoblastic leukemia", *Blood*, 120(22):4407-4417 (2012). doi: 10.1182/blood-2012-05-429811. Epub Aug. 28, 2012.
Gerlinger, M. et al. "Ultra deep T cell receptor sequencing reveals the complexity and intratumour heterogeneity of T cell clones in renal cell carcinomas", *Journal of Pathology*, 231:424-432 (2013).
Giannoni, et al. Allelic exclusion and peripheral reconstitution by TCR transgenic T cells arising from transduced human hematopoietic stem/progenitor cells, Mol Ther., 21(5):1044-54 (2013). doi: 10.1038/mt.2013.8. Epub Feb. 5, 2013.
Gilbert, et al. "The isolation of nucleic acids from fixed, paraffin-embedded tissues—which methods are useful when?", *PLoS One*, 2(6):e537, 12 pages (2007).
Giuggio, et al. "Evolution of the intrahepatic T cell repertoire during chronic hepatitis C virus infection", *Viral Immunology,* 18(1):179-189 (2005).
Gloor et al. "Microbiome profiling by Illumina sequencing of combinatorial sequence-tagged PCR products," *PLoS ONE*, 5(10): e15406, 15 pages (2010).
Godelaine, et al. "Polyclonal CTL responses observed in melanoma patients vaccinated with dendritic cells pulsed with a MAGE-3.A1 peptide", *J Immunol.*, 171(9):4893-4897 (2003).

(56) References Cited

OTHER PUBLICATIONS

Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gottenberg, et al. "Markers of B-lymphocyte activation are elevated in patients with early rheumatoid arthritis and correlated with disease activity in the ESPOIR cohort", Arthritis Res Ther., 11(4): R114 (2009). doi: 10.1186/ar2773. Epub Jul. 23, 2009.
Gratama and Kern. "Flow cytometric enumeration of antigen-specific T lymphocytes", Cytometry A, 58(1): 79-86 (2004).
Gratama, et al. "Measuring antigen-specific immune responses", 2008 update. Cytometry A., 73(11): 971-974 (2008). doi: 10.1002/cyto.a.20655.
Greenman, et al. "Patterns of somatic mutation in human cancer genomes", Nature, 446(7132): 153-158 (2007).
Gribben, JG. "Stem cell transplantation in chronic lymphocytic leukemia", Biol. Blood Marrow Transplant., 15(1 Suppl): 53-58 (2009). doi: 10.1016/j.bbmt.2008.10.022.
Grupp, et al. "Chimeric antigen receptor-modified T cells for acute lymphoid leukemia", N Engl J Med., 368(16):1509-18 (2013). doi: 10.1056/NEJMoa1215134. Epub Mar. 25, 2013.
Grupp, et al. "Adoptive transfer of autologous T cells improves T-cell repertoire diversity and long-term B-cell function in pediatric patients with neuroblastoma", Clin Cancer Res., 18(24):6732-41 (2012). dol: 10.1158/1078-0432.CCR-12-1432. Epub Oct. 23, 2012.
Gulliksen, et al. "Real-time nucleic acid sequence-based amplification in nanoliter volumes", Anal Chem., 76(1): 9-14, Abstract Only (2004).
Gunderson et al. "Decoding Randomly Ordered DNA Arrays", Genome Research, 14: 870-877 (2004).
Hadrup, et al. "Parallel detection of antigen-specific T-cell responses by multidimensional encoding of MHC multimers", Nat Methods, 6(7): 520-526 (2009) (Abstract Only). doi: 10.1038/nmeth.1345. Epub Jun. 21, 2009.
Halldórsdóttir, et al. "Application of BIOMED-2 clonality assays to formalin-fixed paraffin embedded follicular lymphoma specimens: superior performance of the IGK assays compared to IGH for suboptimal specimens", Leukemia & Lymphoma, 48(7): 1338-1343 (2007).
Hamady, et al. "Error-correcting barcoded primers for pyrosequencing hundreds of samples in multiplex", Nature Methods, 5(3):235-237 (2008). doi: 10.1038/nmeth.1184. Epub Feb. 10, 2008.
Hanahan, et al. "Hallmarks of cancer: the next generation", Cell, 144(5): 646-674 (2011). doi: 10.1016/j.cell.2011.02.013.
Harismendy et al. "Evaluation of next generation sequencing platforms for population targeted sequencing studies", Genome Biology, 10:R32, 13 pages (2009).
Harris et al. "Single-Molecule DNA Sequencing of a Viral Genome", Science, 320: 106-109 (2008).
Hathcock, et al. "ATM influences the efficiency of TCR—rearrangement, subsequent TCRβ-dependent T cell development, and generation of the pre-selection TCRβ CDR3 repertoire", PLoS One, 8(4):e62188 (2013). doi: 10.1371/journal.pone.0062188. Print 2013.
Hawkins, et al. "Whole genome amplification—applications and advances", Curr Opin Biotechnol., 13(1): 65-67 (2002).
He, et al. "IgH gene rearrangements as plasma biomarkers in Non-Hodgkin's lymphoma patients", Oncotarget, 2(3): 178-185 (2011).
Hensel et al. "Simultaneous identification of bacterial virulence genes by negative selection", Science, 269(5222): 400-403 (1995).
Hill, et al. "Using ecological diversity measures with bacterial communities", FEMS Microbiol Ecol., 43(1):1-11 (2003). doi: 10.1111/j.1574-6941.2003.tb01040.x.
Hirohata, et al. "Regulation of human B cell function by sulfasalazine and its metabolites", Int Immunopharmacol., 2(5): 631-640, Abstract Only (2002).
Hodges, E. et al. "Diagnostic role of tests for T cell receptor (TCR) genes", J Clin Pathol., 56(1): 1-11 (2003).
Holder and Lewis. "Phylogeny estimation: traditional and bayesian approaches. Nat Rev Genet.", 4(4): 275-84 (2009).

Holt and Jones. "The new paradigm of flow cell sequencing", Genome Research, 18:839-846 (2008).
Hoogenboom, et al. "Multi-subunit proteins on the surface of filamentophage: methodologies for displaying antibody (Fab) heavy and light chains", Nucleic Acids Res., 19(15): 4133-4137 (1991).
Hoogendoorn, et al. "Primary allogeneic T-cell responses against mantle cell lymphoma antigen-presenting cells for adoptive immunotherapy after stem cell transplantation", Clin Cancer Res., 11(14): 5310-5318 (2005).
Hoos, et al. "Improved endpoints for cancer immunotherapy trials", J Natl Cancer Inst., 102(18): 1388-1397 (2010). doi: 10.1093/jnci/djq310. Epub Sep. 8, 2010.
Hoover and Lubkowski. "DNAWorks: an automated method for designing oligonucleotides for PCR-based gene synthesis", Nucleic Acids Res., 30(10): e43, 7 pages (2002).
Hosono, et al. "Unbiased whole-genome amplification directly from clinical samples", Genome Res., 13(5): 954-964 (2003). Epub Apr. 14, 2003.
Hoven, et al. "Detection and isolation of antigen-specific B cells by the fluorescence activated cell sorter (FACS)", J Immunol Methods, 117(2): 275-284, Abstract Only, 2 pages (1989).
Huang, et al. "Isolation of cell-free DNA from maternal plasma using manual and automated systems", Methods Mol Biol., 444: 203-208, Abstract Only (2008). doi: 10.1007/978-1-59745-066-9_15.
Huh, et al. "Microfluidics for flow cytometric analysis of cells and particles", Physiol Meas., 26(3): R73-98, Abstract Only (2005). Epub Feb. 1, 2005.
Huijsmans, et al. "Comparative analysis of four methods to extract DNA from paraffin-embedded tissues: effect on downstream molecular applications", BMC Res Notes, 3:239, 9 pages (2010). doi: 10.1186/1756-0500-3-239.
Huse, et al. "Generation of a large combinatorial library of the immunoglobulin repertoire in phage lambda", Science, 246(4935): 1275-1281, Abstract Only (1989).
Huse et al. "Accuracy and quality of massively parallel DNA pyrosequencing", Genome Biology, 8: R143 (2007).
Iancu, et al. "Profile of a serial killer: cellular and molecular approaches to study individual cytotoxic T-cells following therapeutic vaccination", J Biomed Biotechnol., 2011: 452606 (2011). doi: 10.1155/2011/452606. Epub Nov. 14, 2010.
Illumina. Genome analyzer pipeline software version 1.0 user guide. Part #1004759, 176 pages (2008).
Illumina. Data Sheet, "TruSeq™ exome enrichment kit", 5 pages (2011).
Illumina. "Technical Note: Systems and Software. Calling sequencing SNPs", 3 pages (2010).
Illumina. TruSeq Sample Preparation Kit and Data Sheet. Illumina, Inc., San Diego, CA, 4 pages (2011).
Jabara et al. "Accurate sampling and deep sequencing of the HIV-1 protease gene using a Primer ID", PNAS, 108(50): 20166-20171 (2011).
Jaffe, et al. "Classification of lymphoid neoplasms: the microscope as a tool for disease discovery", Blood, 112(12): 4384-4399 (2008). doi: 10.1182/blood-2008-07-077982.
Jalla, et al. "Enumeration of lymphocyte subsets using flow cytometry: Effect of storage before and after staining in a developing country setting", Indian J Clin Biochem., 19(2): 95-99 (2004). doi: 10.1007/BF02894264.
Jochems and Schlom. "Tumor-infiltrating immune cells and prognosis: the potential link between conventional cancer therapy and immunity", Exp Biol Med (Maywood), 236(5): 567-579 (2011). doi: 10.1258/ebm.2011.011007. Epub Apr. 12, 2011.
Jones, et al. "Human autoimmunity after lymphocyte depletion is caused by homeostatic T-cell proliferation", Proc Natl Acad Sci USA, 110(50) :20200-5 (2013). doi: 10.1073/pnas.1313654110. Epub Nov. 26, 2013.
Jung, et al. "Unraveling V(D)J recombination; insights into gene regulation", Cell, 116(2): 299-311 (2004).
Kalos, M. et al. "T Cells with Chimeric Antigen Receptors Have Potent Antitumor Effects and Can Establish Memory in Patients with Advanced Leukemia", Science Translational Medicine, 3(95ra73): 1-11 (2011).

(56) References Cited

OTHER PUBLICATIONS

Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt.2012.06.005. Epub Jun. 12, 2012.

Kedzierska, et al. "Tracking phenotypically and functionally distinct T cell subsets via T cell repertoire diversity", Mol Immunol., 45(3): 607-618 (2008). Epub Aug. 24, 2007.

Kinde et al. "Detection and quantification of rare mutations with massively parallel sequencing," PNAS, 108(23): 9530-9535 and Supporting Information, 16 pages (2011).

Kircher, et al. "Improved base calling for the Illumina Genome Analyzer using machine learning strategies", Genome Biol., 10(8): R83, 9 pages (2009). doi: 10.1186/gb-2009-10-8-r83. Epub Aug. 14, 2009.

Kirsch, et al. "Defining immunoglobulin somatic hypermutation in de novo diffuse large b-cell lymphoma patients: potential application prognosis and risk stratification", Presented for the 2014 ASH Annual Meeting. Poster. 1 page. Dec. 5-9, 2014.

Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.

Kivioja et al. "Counting absolute numbers of molecules using unique molecular identifiers," Nature Methods, 9(1): 72-76 (2012).

Klarenbeek, P.L. et al. "Human T-cell memory consists mainly of unexpanded clones", Immunology Letters, 133: 42-48 (2010).

Klebanoff, et al. "Therapeutic cancer vaccines: are we there yet?", Immunol Rev., 239(1): 27-44 (2011). doi: 10.1111/j.1600-065X.2010.00979.x.

Klenerman, et al. "Tracking T cells with tetramers: new tales from new tools", Nat Rev Immunol., 2(4):263-272 (2002).

Kneba, et al. "Characterization of clone-specific rearrangement T-cell receptor gamma-chain genes in lymphomas and leukemias by the polymerase chain reaction and DNA sequencing", Blood, 84(2):574-581 (1994).

Koboldt et al., "VarScan: variant detection in massively parallel sequencing of individual and pooled samples", Bioinformatics, 25(17): 2283-2285 (2009).

Koch, et al. "Tumor infiltrating T lymphocytes in colorectal cancer: Tumor-selective activation and cytotoxic activity in situ," Ann Surg., 244(6): 986-992; discussion 992-993 (2006).

Kojima et al. "PCR amplification from single DNA molecules on magnetic beads in emulsion: application for high-throughput screening of transcription factor targets", Nucleic Acids Research, 33: 17, e150, 9 pages (2005).

Kohlmann, et al. "Integration of next-generation sequencing into clinical practice: are we there yet?", Semin Oncol., 39(1): 26-36, Abstract Only (2012). doi: 10.1053/j.seminoncol.2011.11.008.

Krause et al. "Epitope-Specific Human Influenza Antibody Repertoires Diversify by B Cell Intraclonal Sequence Divergence and Interclonal Convergence", The Journal of Immunology, 187: 3704-3711 (2011).

Krueger, et al. "Large scale loss of data in low-diversity illumina sequencing libraries can be recovered by deferred cluster calling", PLoS One, 6(1): e16607, 7 pages (2011). doi: 10.1371/journal.pone.0016607.

Ku, et al. "Exome sequencing: dual role as a discovery and diagnostic tool", Ann Neurol., 71(1):5-14, Abstract Only (2012). doi: 10.1002/ana.22647.

Kumar, et al. "PEG-labeled nucleotides and nanopore detection for single molecule DNA sequencing by synthesis", Sci Rep., 2:684, 8 pages (2012). Epub Sep. 21, 2012.

Kwak, et al. "Induction of immune responses in patients with B-cell lymphoma against the surface-immunoglobulin idiotype expressed by their tumors", N Engl J Med., 327(17):1209-1215 (1992).

Kyu et al. "Frequencies of human influenza-specific antibody secreting cells or plasmablasts post vaccination from fresh and frozen peripheral blood mononuclear cells", Journal of Immunological Methods, 340: 42-47 (2009).

Ladányi, A., et al. "Prognostic impact of B-cell density in cutaneous melanoma", Cancer Immunol. Immunother, 60(12): 1729-1738 (2011).

Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and multiple myeloma (MM)", Blood, vol. 120, No. 21, Abstract 788 (Conference Abstract), Entire Abstract (2012).

Landwehr-Kenzel, et al. "Novel GMP-compatible protocol employing an allogeneic B cell bank for clonal expansion of allospecific natural regulatory T cells", Am J Transplant., 14(3):594-606 (2014). doi: 10.1111/ajt.12629. Epub Jan. 27, 2014.

Larimore, K., et al. "Shaping of Human Germline IgH Repertoires Revealed by Deep Sequencing", The Journal of Immunology, 189(6): 3221-3230 (2012).

Lassmann, et al. "Application of BIOMED-2 primers in fixed and decalcified bone marrow biopsies: analysis of immunoglobulin H receptor rearrangements in B-cell non-Hodgkin's lymphomas", J Mol Diagn., 7(5): 582-591 (2005).

Lazareva-Ulitsky et al, "On the quality of tree-based protein classification," Bioinformatics, 21(9): 1876-1890 (2005).

Lee, et al. "Characterization of circulating T cells specific for tumor-associated antigens in melanoma patients", Nat Med., 5(6): 677-685, Abstract Only (1999).

Lee, et al. "Prognostic implications of type and density of tumour-infiltrating lymphocytes in gastric cancer", Br J Cancer, 99(10): 1704-1711 (2008). doi: 10.1038/sj.bjc.6604738. Epub Oct. 21, 2008.

Lefranc. "IMGT, the international ImMunoGeneTics database", Nucleic Acids Res., 31(1):307-310 (2003).

Leiden, J.M. et al. "The Complete Primary Structure of the T-Cell Receptor Genes From an Alloreactive Cytotoxic Human T-Lymphocyte Clone", Immunogenetics, 24(1): 17-23 (1986).

Leisner, et al. "One-pot, mix-and-read peptide-MHC tetramers", PLoS One, 3(2):e1678, 11 pages (2008). doi: 10.1371/journal.pone.0001678.

Lennon, et al. "A scalable, fully automated process for construction of sequence-ready barcoded libraries for 454", Genome Biol., 11(2):R15, 9 pages (2010). doi: 10.1186/gb-2010-11-2-r15. Epub Feb. 5, 2010.

Leary, et al. "Development of personalized tumor biomarkers using massively parallel sequencing", Sci Transl Med., 2(20): 20ra14 (2010). doi: 10.1126/scitranslmed.3000702.

Leone, et al. "Molecular beacon probes combined with amplification by NASBA enable homogeneous, real-time detection of RNA", Nucleic Acids Research, 26(9): 2150-2155 (1998).

Leproust, et al. "Synthesis of high-quality libraries of long (150mer) oligonucleotides by a novel depurination controlled process", Nucleic Acids Res., 38(8): 2522-2540 (2010). doi: 10.1093/nar/gkq163. Epub Mar. 22, 2010.

Lessin, et al. "Molecular diagnosis of cutaneous T-cell lymphoma: polymerase chain reaction amplification of T-cell antigen receptor beta-chain gene rearrangements", J Invest Dermatol., 96(3): 299-302 (1991).

Li, et al. "β cell-specific CD4+ T cell clonotypes in peripheral blood and the pancreatic islets are distinct", J Immunol., 183(11): 7585-7591 (2009). doi: 10.4049/jimmunol.0901587. Epub Nov. 16, 2009.

Li et al, "Mapping short DNA sequencing reads and calling variants using mapping quality scores," Genome Research, 18: 1851-1858 (2008).

Liedtke, et al. "A comparison of methods for RNA extraction from lymphocytes for RT-PCR", PCR Methods and Applications, 4(3): 185-187 (1994).

Liu, et al. "CD127 expression inversely correlates with FoxP3 and suppressive function of human CD4+T reg cells", J Exp Med., 203(7): 1701-1711 (2006). Epub Jul. 3, 2006.

Lo, et al. T cell immunodominance is dictated by the positively selecting self-peptide, Elife, 3:e01457 (2014). doi: 10.7554/eLife.01457. Epub Jan. 14, 2014.

Logan, et al., "High-throughput immunoglobulin gene sequencing quantifies minimal residual disease in CLL with 10e-6 sensitivity and strongly predicts relapse after allogeneic hematopoietic cell transplantation", Blood, vol. 118 (21), Abstract 2542 (2011).

(56) References Cited

OTHER PUBLICATIONS

Logan, et al., "Massively parallel immunoglobulin gene sequencing provides ultra-sensitive minimal residual disease detection and predicts post-transplant relapse in acute lymphoblastic leukemia by three to six months", *Blood*, vol. 118 (21), Abstract 4104 (2011).
Lossos, et al. "Transformation of follicular lymphoma to diffuse large-cell lymphoma: alternative patterns with increased or decreased expression of c-myc and its regulated genes", *PNAS*, 99(13): 8886-8891 (2002). Epub Jun. 19, 2002.
Lowman, et al. "Monovalent phage display: a method for selecting variant proteins from random libraries", *Methods: A Companion to Methods in Enzymology*, 3: 205-216, Abstract Only (1991).
Lyamichev, et al. "Polymorphism identification and quantitative detection of genomic DNA by invasive cleavage of oligonucleotide probes", *Nat Biotechnol.*, 17(3): 292-396 (1999).
Mackay, et al. "Real-time PCR in virology", *Nucleic Acids Res.*, 30(6): 1292-305 (2002).
Mahmoud, S.M.A. et al. "Tumor-Infiltrating CD8+ Lymphocytes Predict Clinical Outcome in Breast Cancer", *Journal of Clinical Oncology*, 29(15): 1949-1955 (2011).
Maldonado, et al. "Intramuscular therapeutic vaccination targeting HPV16 induces T cell responses that localize in mucosal lesions", Sci Transl Med., 6(221): 221ra13 (2014). doi: 10.1126/scitranslmed.3007323.
Malyguine, et al. "ELISPOT Assay for Monitoring Cytotoxic T Lymphocytes (CTL) Activity in Cancer Vaccine Clinical Trials", *Cells*, 1(2): 111-126 (2012). doi: 10.3390/cells1020111.
Manion et al., "Reducing Error in Next Generation Sequencing Data with NextGENe Software's Condensation Tool™", Mar. 2009, pp. 1-3. XP055226038.
Manrao, et al. "Reading DNA at single-nucleotide resolution with a mutant MspA nanopore and phi29 DNA polymerase", *Nat Biotechnol.*, 30(4): 349-353 (2012). doi: 10.1038/nbt.2171.
Mar et al. "Inferring steady state single-cell gene expression distributions from analysis of mesoscopic samples", *Genome Biology*, 7(12): R119, 12 pages (2006).
Marrero, et al. "High-throughput sequencing of islet-infiltrating memory CD4+ T cells reveals a similar pattern of TCR Vβ usage in prediabetic and diabetic NOD mice", PLoS One, 8(10):e76546 (2013). doi: 10.1371/journal.pone.0076546. eCollection 2013.
Martin-Jimenez, et al. "Molecular characterization of heavy chain immunoglobulin gene rearrangements in Waldenström's macroglobulinemia and IgM monoclonal gammopathy of undetermined significance", *Haematologica*, 92(5): 635-642 (2007).
Mary et al. "Analysis of gene expression at the single-cell level using microdroplet-based microfluidic technology", *Biomicrofluidics*, 5: 024109-1-024109-10 (2011).
Matsubara, et al. "Microchamber array based DNA quantification and specific sequence detection from a single copy via PCR in nanoliter volumes", *Biosens Bioelectron*, 20(8): 1482-1490, Abstract Only (2005).
Mazor et al. "Antibody internalization studied using a novel IgG binding toxin fusion", *Journal of Immunological Methods*, 321: 41-59 (2007).
Mazumder, et al., "Detection of multiple myeloma cells in peripheral blood using high-throughput sequencing assay" *Blood*, vol. 120, No. 21, Abstract 321 (Conference Abstract), Entire Abstract (2012).
McCloskey et al. "Encoding PCR products with batch-stamps and barcodes," *Biochem. Genet.*, 45: 761-767 (2007).
McGoldrick, et al. "Cytomegalovirus-specific T cells are primed early after cord blood transplant but fail to control virus in vivo", *Blood*, 121(14): 2796-2803 (2013). doi: 10.1182/blood-2012-09-453720. Epub Feb. 14, 2013.
Mei et al. "Blood-borne human plasma cells in steady state are derived from mucosal immune responses", *Blood*, 113(11): 2461-2469 (2009).
Meijer et al. "Isolation of Human Antibody Repertoires with Preservation of the Natural Heavy and Light Chain Pairing", *J. Mol. Biol.*, 358: 764-772 (2006).

Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.
Meier et al. "Simultaneous evaluation of T-cell and B-cell clonality, t(11;14) and t(14;18), in a single reaction by a four-color multiplex polymerase chain reaction assay and automated High-Resolution fragment analysis", *American Journal of Pathology*, 159(6): 2031-2043 (2001).
Meier, et al. "The influence of different stimulation conditions on the assessment of antigen-induced CD154 expression on CD4+ T cells", *Cytometry A.*, (11):1035-1042 (2008). doi: 10.1002/cyto.a.20640.
Metzker, "Sequencing Technologies—The Next Generation", *Nature Reviews, Genetics*, 11:31-46 (2010).
Meyer et al. "Targeted high-throughput sequencing of tagged nucleic acid samples", *Nucleic Acids Research*, 35(15): e97, 5 pages (2007).
Michálek, et al. "Identification and monitoring of graft-versus-host specific T-cell clone in stem cell transplantation", *The Lancet*, 361(9364): 1183-1185 (2003).
Miller, et al., "Assembly algorithms for next-generation sequencing data", Genomics, 95(6): 315-327 (2010).
Miltenyi, et al. "High gradient magnetic cell separation with MACS", *Cytometry*, 11(2): 231-238 (1990).
Miner et al. "Molecular barcodes detect redundancy and contamination in hairpin-bisulfite PCR", *Nucleic Acids Research*, 32(17): e135, 4 pages (2004).
Mitra, et al. "Fluorescent in situ sequencing on polymerase colonies", *Anal Biochem.*, 320(1): 55-65, Abstract Only (2003).
Mittelstadl, et al. "Thymocyte responsiveness to endogenous glucocorticoids is required for immunological fitness", J Clin Invest., 122(7):2384-94 (2012). doi: 10.1172/JCI63067. Epub Jun. 1, 2012.
Miyashita, et al. "N-Methyl substituted 2',4'-BNANC: a highly nuclease-resistant nucleic acid analogue with high-affinity RNA selective hybridization", *Chem Commun* (Camb), (36): 3765-3767, Abstract Only (2007). Epub Jul. 9, 2007.
Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).
Molloy, et al. "Soluble T cell receptors: novel immunotherapies", *Curr Opin Pharmacol.*, 5(4): 438-443 (2005) (Abstract Only).
Moody, et al. "Antigen-specific B cell detection reagents: use and quality control", *Cytometry A.*, 73(11): 1086-1092 (2008). doi: 10.1002/cyto.a.20599.
Morgan, et al. "Cancer regression in patients after transfer of genetically engineered lymphocytes", *Science*, 314(5796): 126-129 (2006). Epub Aug. 31, 2006.
Morozova et al. "Applications of New Sequencing Technologies for Transcriptome Analysis", *Annu. Rev.Genomics Hum. Genet.*, 10: 135-151 (2009).
Morrissy et al. "Next-generation tag sequencing for cancer gene expression profiling", *Genome Research*, 19: 1825-1835 (2009).
Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.
Mueller, et al. "Human Treg responses allow sustained recombinant aden-associated virus-mediated transgene expression", J Clin Invest., 123(12): 5310-5318 (2013). doi: 10.1172/JCI70314. Epub Nov. 15, 2013.
Muraro, et al. "T cell repertoire following autologous stem cell transplantation for multiple sclerosis", J Clin Invest., 124(3): 1168-72 (2014). doi: 10.1172/JCI71691. Epub Feb. 17, 2014.
Murugan, et al. "Statistical inference of the generation probability of T-cell receptors from sequence repertoires", *PNAS*, 109(40): 16161-16166 (2012). doi: 10.1073/pnas.1212755109. Epub Sep. 17, 2012.
Naito, et al. "CD8+ T cells infiltrated within cancer cell nests as a prognostic factor in human colorectal cancer", *Cancer Research*, 58(16): 3491-3494 (1998).
Nakano, et al. "Single-molecule PCR using water-in-oil emulsion", *J Biotechnol.*, 102(2): 117-124, Abstract Only (2003).
Navarrete, et al. "Upfront immunization with autologous recombinant idiotype Fab fragment without prior cytoreduction in indolent

(56) References Cited

OTHER PUBLICATIONS

B-cell lymphoma", *Blood*, 117(5): 1483-1491 (2011). doi: 10.1182/blood-2010-06-292342. Epub Nov. 2, 2010.
Needleman and Wunsch. "A general method applicable to the search for similarities in the amino acid sequence of two proteins", *J Mol Biol.*, 48(3): 443-453 (1970).
Neller, et al. "High frequency of herpesvirus-specific clonotypes in the human T cell repertoire can remain stable over decades with minimal turnover", J Virol., 87(1): 697-700 (2013). doi: 10.1128/NI.02180-12. Epub Oct. 17, 2012.
Nelson. "CD20+ B cells: the other tumor-infiltrating lymphocytes", *The Journal of Immunology*, 185(9): 4977-4982 (2010). doi: 10.4049/jimmunol.1001323.
Newman, et al. "Identification of an antigen-specific B cell population", *J Immunol Methods*, 272(1-2): 177-187, Abstract Only (2003).
Nielsen, et al. "Peptide nucleic acid (PNA). A DNA mimic with a pseudopeptide backbone", *Chem. Soc. Rev.*, 26:73-78, Abstract Only (1997).
Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.
Nucleis product webpage, "Exonuclease I-Shrimp alkaline phosphatase clean up of PCR products," (Published on webpage 2013) Downloaded Dec. 15, 2015.
Oble, et al. "Focus on TILs: prognostic significance of tumor infiltrating lymphocytes in human melanoma", *Cancer Immunity*, 9: 3, 20 pages (2009).
O'Brian et al., "Sorting out mix-ups. The provenance of tissue sections may be confirmed by PCR using microsatellite markers", Am. J. Clin. Pathol., 106(6): 758-764 (1996). (Abstract Only).
Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.
Ohtani. "Focus on TILs: prognostic significance of tumor infiltrating lymphocytes in human colorectal cancer", *Cancer Immunity*, 7: 4, 9 pages (2007).
Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab.2010.01.014. Epub Jan. 15, 2010.
Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).
Pagès, Franck. Tumor-associated immune parameters for personalized patient care. Sci Transl Med., 5(214):214fs42 (2013). doi: 10.1126/scitranslmed.3007942.
Palmowski, et al. "The use of HLA class I tetramers to design a vaccination strategy for melanoma patients", *Immunol Rev.*, 188: 155-163 (2002) (Abstract Only).
Palomaki, et al. "DNA sequencing of maternal plasma reliably identifies trisomy 18 and trisomy 13 as well as Down syndrome: an international collaborative study", *Genet Med.*, 14(3): 296-305 (2012). doi: 10.1038/gim.2011.73. Epub Feb. 2, 2012.
Pan, et al. "A new FACS approach isolates hESC derived endoderm using transcription factors", *PLoS One*, 6(3): e17536, 9 pages (2011). doi: 10.1371/journal.pone.0017536.
Parameswaran et al. "A pyrosequencing-tailored nucleotide barcode design unveils opportunities for large-scale sample multiplexing", *Nucleic Acids Research*, 35(19): e130, 9 pages (2007).
Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.
Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.
Paszkiewicz et al, "De novo assembly of short sequence reads," Briefings in Bioinformatics, 11(5): 457-472 (2010).

Payne, et al. "Peripheral blood mononuclear cells of patients with breast cancer can be reprogrammed to enhance anti-HER-2/neu reactivity and overcome myeloid-derived suppressor cells", Breast Cancer Res Treat., 142(1):45-57 (2013). doi: 10.1007/s10549-013-2733-5. Epub Oct. 25, 2013.
Peet. "The Measurement of Species Diversity", *Annual Review of Ecology and Systematics*, 5: 285-307, Abstract Only (1974).
Petrosino, et al. "Metagenomic pyrosequencing and microbial identification", *Clin Chem.*, 55(5): 856-866 (2009). doi: 10.1373/clinchem.2008.107565. Epub Mar. 5, 2009.
PCT/US2009/006053, Written Opinion dated Jun. 15, 2010, 4 pages.
PCT/US2010/037477, International Preliminary Report on Patentability dated Jan. 4, 2012, 7 pages.
PCT/US2011/000791, International Preliminary Report on Patentability dated Nov. 6, 2012, 10 pages.
PCT/US2011/049012, International Preliminary Report on Patentability dated Feb. 26, 2013, 5 pages.
Pekin, D. et al. "Quantitative and sensitive detection of rare mutations using droplet-based microfluidics", *Lab Chip*, 11(3): 2156-2166 (2011).
Perkel, J. "Overcoming the Challenges of Multiplex PCR", *Biocompare Editorial Article*, Oct. 23, 2012, 6 Pages, can be retrieved at URL:http://www.biocompare.com/Editorial-Articles/117895-Multiplex-PCR/>.
Plasilova et al. "Application of the Molecular Analysis of the T-Cell Receptor Repertoire in the Study of Immune-Mediated Hematologic Diseases", *Hematology*, 8(3): 173-181 (2003).
Polstra, et al. "Development of real-time NASBA assays with molecular beacon detection to quantify mRNA coding for HHV-8 lytic and latent genes", *BMC Infect Dis.*, 2: 18 (2002). Epub Sep. 4, 2002.
Pourmand, et al. "Direct electrical detection of DNA synthesis", *PNAS*, 103(17): 6466-6470 (2006). Epub Apr. 13, 2006.
Polz and Cavanaugh. "Bias in Template-to-Product Ratios in Multitemplate PCR", *Applied and Environmental Microbiology*, 64(10): 3724-3730 (1998).
Porter, et al. "Chimeric antigen receptor-modified T cells in chronic lymphoid leukemia", N Engl J Med., 365(8):725-33 (2011). doi: 10.1056/NEJMoa1103849. Epub Aug. 10, 2011.
Prabakaran et al. "454 antibody sequencing—error characterization and correction", *BMC Research Notes*, 4: 404 (2011).
Putnam, et al. "Clinical grade manufacturing of human alloantigen-reactive regulatory T cells for use in transplantation", Am J Transplant., 13(11): 3010-20 (2013). doi: 10.1111/ajt.12433. EpubSep. 18, 2013.
Qiu et al. "DNA sequence-based "bar codes" for tracking the origins of expressed sequence tags from a maize cDNA library constructed using multiple mRNA sources", *Plant Physiology*, 133(2): 475-481 (2003).
Quince et al. "Removing Noise From Pyrosequenced Amplicons", *BMC Informatics*, 12: 38 (2011).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", *Semin Cancer Biol.*, 20(4): 254-260 (2010). doi: 10.1016/j.semcancer.2010.06.002. Epub Jul. 1, 2010.
Reddy, et al. "Monoclonal antibodies isolated without screening by analyzing the variable-gene repertoire of plasma cells", *Nature Biotechnology*, 28(9): 965-969 (2010). doi: 10.1038/nbt.1673. Epub Aug. 29, 2010.
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.

(56) References Cited

OTHER PUBLICATIONS

Robert, et al. "CTLA4 blockade broadens the peripheral T-cell receptor repertoire", Clin Cancer Res., 20(9):2424-32 (2014). doi: 10.1158/1078-0432.CCR-13-2648. Epub Feb. 28, 2014.
Robins, et al. "CD4+ and CD8+ T cell β antigen receptors have different and predictable V and J gene usage and CDR3 lengths", *J. Immunol.*, 188: 115.10, Abstract (2012).
Robins, H. et al. "Digital Genomic Quantification of Tumor Infiltrating Lymphocytes", *Science Translational Medicine*, 5:214ra169, 19 pages, Supplementary Materials (2013).
Robins, et al. "Effects of aging on the human adaptive immune system revealed by high-throughput DNA sequencing of T cell receptors", *J Immunol.*, 188: 47.16, Abstract (2012).
Robins, et al. "Immune profiling with high-throughput sequencing." Presented for the ASHI 2011 conference. Oct. 2011. Poster. 1 page.
Robins, H. et al. "The Computational Detection of Functional Nucleotide Sequence Motifs in the Coding Regions of Organisms", *Exp Biol Med*, 233(6): 665-673 (2008).
Ronaghi, et al. "A sequencing method based on real-time pyrophosphate", *Science*, 281(5375): 363, 365, 5 pages (1998).
Rosenberg, S.A. et al. "New Approach to the Adoptive Immunotherapy of Cancer with Tumor-Infiltrating Lymphocytes", *Science*, 233(4770): 1318-1321 (1986).
Roshal, M. et al. "Immaturity Associated Antigens are Lost During Induction for T Cell Lymphoblastic Leukemia: Implications for Minimal Residual Disease Detection", *Cytometry Part B (Clinical Cytometry)*, 78:139-146 (2010).
Rothberg, et al. "An integrated semiconductor device enabling non-optical genome sequencing", *Nature*, 475(7356): 348-352 (2011). doi: 10.1038/nature10242.
Rothberg et al. "The development and impact of 454 sequencing", *Nature Biotechnology*, 26(10): 1117-1124 (2008).
Rozen, S. et al. "Primer3 on the WWW for General Users and for Biologist Programmers", *Methods in Molecular Biology, Bioinfomatics Methods and Protocols*, 132:365-386 (2000).
Saada, R. et al. "Models for antigen receptor gene rearrangement: CDR3 length", *Immunology and Cell Biology*, 85:323-332 (2007).
Salzberg. "Mind the gaps", *Nature Methods*, 7(2): 105-106 (2010).
Sanchez-Freire et al. "Microfluidic single-cell real-time PCR for comparative analysis of gene expression patterns", *Nature Protocols*, 7(5): 829-838 (2012).
Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Sandberg, et al. "Capturing whole-genome characteristics in short sequences using a naïve Bayesian classifier", *Genome Res.*, 11(8): 1404-9 (2001).
Santalucia, Jr., J. "Physical Principles and Visual-OMP Software for Optimal PCR Design," *Methods in Molecular Biology*, 402(PCR Primer Design):3-33, 40 pages (2007).
Santamaria, P. et al. "Beta-Cell-Cytotoxic CD8 T Cells from Nonobese Diabetic Mice Use Highly Homologous T Cell Receptor a-Chain CDR3 Sequences", *The Journal of Immunology*, 154(5):2494-2503 (1995).
Sartorius Stedim Biotech product brochure, "Primer removal after a PCR reaction with Vivacon® 2", (2010).
Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005). Epub Dec. 12, 2005.
Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).
Schlissel, M.S. et al. "Leukemia and lymphoma: a cost of doing business for adaptive immunity", *Genes Dev.*, 20(12): 1539-1544 (2006).
Schloss, PD et al. Reducing the Effects of PCR Amplification and Sequencing Artifacts on 16S Rrna-Based Studies. PLoS One. Dec. 14, 2011, vol. 6, No. 12; e27310; DOI: 1 0.1371/journal.pone.0027310.
Schmitt et al. "Detection of ultra-rare mutations by next-generation sequencing," *PNAS*, 109(36): 14508-14513 and Supporting Information, 9 pages (2012).
Schrappe, M. et al. "Late MRD response determines relapse risk overall and in subsets of childhood T-cell ALL: results of the AIEOP-BFM-ALL 2000 study", *Blood*, 118(8): 2077-2084 (2011).
Schreiber et al. "Cancer immunoediting: integrating immunity's roles in cancer suppression and promotion", *Science*, 331(6024): 1565-1570 (2011). doi: 10.1126/science.1203486.
Schweiger et al. "Genome-wide massively parallel sequencing of formaldehyde fixed-paraffin embedded (FFPE) tumor tissues for copy-number- and mutation-analysis", *PLoS One*, 4(5): e5548, 7 pages (2009). doi: 10.1371/journal.pone.0005548. Epub May 14, 2009.
Sebastian, E. et al., "Molecular Characterization of immunoglobulin gene rearrangements in diffuse large B-cell lymphoma", *Am. J. Pathol.*, 181: 1879-1888, Abstract (2012). (Epub: Sep. 28, 2012).
Sehouli et al. "Epigenetic quantification of tumor-infiltrating T-lymphocytes" *Epigenetics*, 6(2): 236-246 (2011). Epub Feb. 1, 2011.
Seitz, et al. "Reconstitution of paired T cell receptor α- and β-chains from microdissected single cells of human inflammatory tissues", *PNAS*, 103: 12057-12062 (2006).
Seo, et al. "Four-color DNA sequencing by synthesis on a chip using photocleavable fluorescent nucleotides", *PNAS*, 102(17): 5926-5931 (2005). Epub Apr. 13, 2005.
Sfanos et al. "Human Prostate-Infiltrating CD8+ T Lymphocytes are Oligoclonal and PD-1-+", *The Prostate*, 69(15): 1694-1703 (2009).
Shendure, et al. "Accurate multiplex polony sequencing of an evolved bacterial genome", *Science*, 309(5741): 1728-1732, Abstract Only (2005). Epub Aug. 4, 2005.
Sherwood, A. et al. "Deep Sequencing of the Human TCRγ and TCRβ Repertoires Suggests that TCR β Rearranges After αβ and γδ T Cell Commitment", Science Translational Medicine, *Sci. Transl. Med.*, 3(90): 1-7 (2011).
Sherwood, et al. "New Technologies for Measurements of Tumor Infiltrating Lymphocytes", Presented Nov. 7, 2012 Moscone Center, Exhibit Halls ABC.
Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.
Shino, et al. "Usefulness of immune monitoring in lung transplantation using adenosine triphosphate production in activated lymphocytes", *The Journal of Heart and Lung Transplant*, 31: 996-1002 (2012).
Shiroguchi et al. "Digital RNA sequencing minimizes sequence-dependent bias and amplification noise with optimized single-molecule barcodes", *PNAS*, 109(4): 1347-1352 (2012).
Shoemaker et al. "Quantitative phenotypic analysis of yeast deletion mutants using a highly parallel molecular bar-coding strategy," *Nature Genetics*, 14(4): 450-456 (1996).
Shumaker, et al. "Mutation detection by solid phase primer extension", *Hum Mutat.*, 7(4): 346-354, Abstract Only (1996).
Sia, et al. "Microfluidic devices fabricated in poly(dimethylsiloxane) for biological studies", *Electrophoresis*, 24(21): 3563-3576, Abstract Only (2003).
Silver, N. et al. "Selection of housekeeping genes for gene expression studies in human reticulocytes using real-time PCR", *BMC Molecular Biology*, 7(33):1-9 (2006).
Sims, et al. "Fluorogenic DNA sequencing in PDMS microreactors", *Nat Methods*, 8(7): 575-580 (2011). doi: 10.1038/nmeth.1629.
Sims, et al. "MHC-peptide tetramers for the analysis of antigen-specific T cells", *Expert Rev Vaccines*, 9(7): 765-774 (2010). doi: 10.1586/erv.10.66.
Sint, D., et al. "Advances in multiplex PCR: balancing primer efficiencies and improving detection success", *Methods in Ecology and Evolution*, 3(5): 898-905 (2012).

(56) References Cited

OTHER PUBLICATIONS

Smith, et al. "Comparison of biosequences", *Advances in Applied Mathematics*, 2: 482-489 (1981).
Smith et al. "Rapid generation of fully human monoclonal antibodies specific to a vaccinating antigen", *Nature Protocols*, 4(3): 372-384 and CORRIGENDA (2009).
Smith et al. "Rapid whole-genome mutational profiling using next-generation sequencing technologies", *Genome Research*, 18: 1638-1642 (2008).
Smith et al. "Quantitative phenotyping via deep barcode sequencing", *Genome Research*, 19: 1836-1842 (2009).
Smith et al, "Using quality scores and longer reads improves accuracy of Solexa read mapping," BMC Bioinformatics, 9: 128 (2008).
Sobrino, et al. "SNPs in forensic genetics: a review on SNP typing methodologies", *Forensic Sci Int.*, 154(2-3): 181-194, Abstract Only (2005). Epub Jan. 11, 2005.
Spreafico, et al. "A circulating reservoir of pathogenic-like CD4+ T cells shares a genetic and phenotypic signature with the inflamed synovial micro-environment", *Ann Rheum Dis.*, 0: 1-7 (2014). doi: 10.1136/annrheumdis-2014-206226. [Epub ahead of print].
Srinivasan et al. "Effect of fixatives and tissue processing on the content and integrity of nucleic acids", *Am J Pathol.*, 161(6): 1961-1971 (2002).
Srivastava and Robins. "Palindromic nucleotide analysis in human T cell receptor rearrangements", PLoS One, 7(12):e52250 (2012). doi: 10.1371/journal.pone.0052250. Epub Dec. 21, 2012.
Standard Sequencing Primers, Max Planck Genome Center Cologne, Jan. 15, 2011, 2 pages, downloaded from https://genomecentre.mpipz.mpg.de/SeqOrderDB/export/sequencing-primers.html.
Steenbergen, et al. "Frequent ongoing T-cell receptor rearrangements in childhood B-precursor acute lymphoblastic leukemia: implications for monitoring minimal residual disease", *Blood*, 86(2): 692-702, Abstract Only (1995).
Stein and Nombela-Arrieta. "Chemokine control of lymphocyte trafficking: a general overview", *Immunology*, 116(10):1-12 (2005).
Steinmetz, O.M. et al. "Chemokines and B cells in renal inflammation and allograft rejection", *Frontiers in Bioscience* (Schol. Ed.), 1:13-22 (2009).
Stemmer, et al. "Single-step assembly of a gene and entire plasmid from large numbers of oligodeoxyribonucleotides", *Gene*, 164(1): 49-53 (1995).
Stewart and Schwartz. "Immunoglobulin V regions and the B cell", *Blood*, 83(7): 1717-1730 (1994).
Stickler, et al. "An in vitro human cell-based assay to rank the relative immunogenicity of proteins", *Toxicol Sci.*, 77(2): 280-289 (2004). Epub Dec. 22, 2003.
Stiller et al. "Direct multiplex sequencing (DMPS)—a novel method for targeted high-throughput sequencing of ancient and highly degraded DNA", *Genome Research*, 19: 1843-849 (2009).
Stratton. "Exploring the genomes of cancer cells: progress and promise", *Science*, 331(6024): 1553-1558 (2011). doi: 10.1126/science. 1204040.
Swarup and Rajeswari. "Circulating (cell-free) nucleic acids—a promising, non-invasive tool for early detection of several human diseases", *FEBS Letters*, 581(5): 795-799 (2007). Epub Feb. 2, 2007.
Szczepanski, T. et al. "Minimal residual disease in leukemia patients", *Lancet Oncology*, 2:409-417 (2001).
Takamatsu, et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).
Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).
Taubenheim et al. "High Rate of Antibody Secretion is not Integral to Plasma Cell Differentiation as Revealed by XBP-1 Deficiency", *The Journal of Immunology*, 189: 3328-3338 (2012).
Tautz, et al. "Cryptic simplicity in DNA is a major source of genetic variation", *Nature*, 322(6080): 652-656 (1986).

Tawfik, et al. "Man-made cell-like compartments for molecular evolution", *Nat Biotechnol.*, 16(7): 652-656, Abstract Only (1998).
ten Bosch et al. "Keeping Up With the Next Generation Massively Parallel Sequencing in Clinical Diagnostics", *Journal of Molecular Diagnostics*, 10(6): 484-492 (2008).
Tewhey, R. et al. "Corrigendum: Microdroplet-based PCR enrichment for large-scale targeted sequencing", *Nature Biotechnology*, 28(2):178, 1 page (2010).
Tewhey, R. et al. "Microdroplet-based PCR enrichment for large-scale targeted sequencing," *Nature Biotechnology*, 27(11):1025-1031 (2009).
Thiel, et al. "Antigen-specific cytometry—new tools arrived!", *Clin Immunol.*, 111(2): 155-161, Abstract Only (2004).
Toriello et al. "Integrated microfluidic bioprocessor for single-cell gene expression analysis", *PNAS*, 105(51): 20173-20178 (2008).
Triebel, F. et al. "A Unique V-J-C-Rearranged Gene Encodes a γ Protein Expressed on the Majority of CD3+ T Cell Receptor-a/fr Circulating Lymphocytes", *J. Exp. Med.*, 167:694-699 (1988).
Tsai et al. "Discovery of rare mutations in populations: Tilling by sequencing", Plant Physiology, 156(3):1257-1268 (and Supplemental Data) (2011).
Tsankova, et al. "Peripheral T -cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", *Oncotarget*, 3(4): 502-513 (2012).
Turcotte and Rosenberg. "Immunotherapy for metastatic solid cancers", *Adv Surg.*, 45: 341-360 (2011).
Unrau and Deugau. "Non-cloning amplification of specific DNA fragments from whole genomic DNA digests using DNA 'indexers'", *Gene.*, 145(2): 163-169, Abstract Only, 2 pages (1994).
Uppaluri et al. "Focus on TILs: prognostic significance of tumor infiltrating lymphocytes in head and neck cancers", *Cancer Immunity*, 8:16, 10 pages (2008).
Urban, et al. "A systematic and quantitative analysis of PCR template contamination", *J Forensic Sci.*, 45(6): 1307-1311 (2000).
Urquhart, et al. "Rate-controlled delivery systems in drug and hormone research", *Annu Rev Pharmacol Toxicol.*, 24: 199-236, Abstract Only (1984).
Van Der Velden, V.H.J., et al. "Optimization of PCR-based minimal residual disease diagnostics for childhood acute lymphoblastic leukemia in a multi-center setting," *Leukemia*, 21:706-713 (2007).
Van Der Velden, V.H.J., et al. "Real-time quantitative PCR for detection of minimal residual disease before allogeneic stem cell transplantation predicts outcome in children with acute lymphoblastic leukemia", *Leukemia*, 15:1485-1487 (2001).
Van Dongen, J.J.M. et al. "Prognostic value of minimal residual disease in acute lymphoblastic leukaemia in childhood", *The Lancet*, 352:1731-1738 (1998).
Varley and Mitra. "Nested patch PCR enables highly multiplexed mutation discovery in candidate genes", *Genome Research*, 18: 1844-1850 (2008).
Venturi, et al. "A mechanism for TCR sharing between T cell subsets and individuals revealed by pyrosequencing", *J Immunol.*, 186(7): 4285-4294 (2011). doi: 10.4049/jimmunol.1003898. Epub Mar. 7, 2011.
Venturi, V. et al. "TCR β-Chain Sharing in Human CD8+ T Cell Responses to Cytomegalovirus and EBV", *The Journal of Immunology*, 181:7853-7862 (2008).
Venturi, V. et al. "The molecular basis for public T-cell responses?", *Nature Reviews*, 8:231-238 (2008).
Verhagen, O.J.H.M., et al. "Application of germline IGH probes in real-time quantitative PCR for the detection of minimal residual disease in acute lymphoblastic leukemia", *Leukemia*, 14:1426-1435 (2000).
Vester, et al. "LNA (locked nucleic acid): high-affinity targeting of complementary RNA and DNA", *Biochemistry*, 43(42): 13233-13241, Abstract Only (2004).

(56) References Cited

OTHER PUBLICATIONS

Vlassov, et al. "Circulating nucleic acids as a potential source for cancer biomarkers", *Curr Mol Med.*, 10(2): 142-165 (2010).
Vogelstein et al. "Cancer genome landscapes", *Science*, 339(6127): 1546-1558 (2013). doi: 10.1126/science.1235122.
Vogelstein and Kinzler. "Digital PCR," *Genetics, PNAS*, 96:9236-9241 (1999).
Wälchli, et al. "A practical approach to T-cell receptor cloning and expression", *PLoS One*, 6(11): e27930, 11 pages (2011). doi: 10.1371/journal.pone.0027930. Epub Nov. 21, 2011.
Wang, et al. "Balanced-PCR amplification allows unbiased identification of genomic copy changes in minute cell and tissue samples", *Nucleic Acids Research*, 32(9): e76, 10 pages (2004).
Ward and Marelli-Berg. "Mechanisms of chemokine and antigen-dependent T-lymphocyte navigation", *Biochem. J.*, 418:13-27 (2009).
Welch and Link. "Genomics of AML: clinical applications of next-generation sequencing", *American Society of Hematology*, 2011: 30-35 (2011). doi: 10.1182/asheducation-2011.1.30.
Wells, et al. "Rapid evolution of peptide and protein binding properties in vitro", *Curr Opin Biotechnol.*, 3(4): 355-362, Abstract Only (1992).
Weng, et al. "Minimal residual disease monitoring with high-throughput sequencing of T cell receptors in cutaneous T cell lymphoma", Sci Transl Med., 5(214):214ra171 (2013). doi: 10.1126/scitranslmed.3007420.
Westermann and Pabst. "Distribution of lymphocyte subsets and natural killer cells in the human body", *Clin Investig.*, 70(7): 539-544 (1992).
Weusten, et al. "Principles of quantitation of viral loads using nucleic acid sequence-based amplification in combination with homogeneo detection using molecular beacons", *Nucleic Acids Res.*, 30(6): e26, 7 pages (2002).
White et al. "High-throughput microfluidic single-cell RT-qPCR", *PNAS*, 108(34): 13999-14004 (2011).
Whiteford, et al. "Swift: primary data analysis for the Illumina Solexa sequencing platform", *Bioinformatics*, 25(17): 2194-2199 (2009). doi: 10.1093/bioinformatics/btp383. Epub Jun. 23, 2009.
Williams, et al. "Amplification of complex gene libraries by emulsion PCR", *Nat Methods*, 3(7): 545-550 (2006).
Wolda. "Similarity Indices, Sample Size and Diversity", *Oecologia* (Berl), 50:296-302 (1981).
Wolfl, et al. "Activation-induced expression of CD137 permits detection, isolation, and expansion of the full repertoire of CD8+ T cells responding to antigen without requiring knowledge of epitope specificities", *Blood*, 110(1): 201-210 (2007). Epub Mar. 19, 2007.
Wolfl, et al. "Use of CD137 to study the full repertoire of CD8+ T cells without the need to know epitope specificities", *Cytometry A.*, 73(11): 1043-1049 (2008). doi: 10.1002/cyto.a.20594.
Wood, B. "9-Color and 10-Color Flow Cytometry in the Clinical Laboratory", *Arch Pathol Lab Med*, 130:680-690 (2006).
Wood, et al. "Using next-generation sequencing for high resolution multiplex analysis of copy number variation from nanogram quantities of DNA from formalin-fixed paraffin-embedded specimens", *Nucleic Acids Research*, 38(14): e151, 11 pages (2010). doi: 10.1093/nar/gkq510. Epub Jun. 4, 2010.
Wrammert et al. "Rapid cloning of high-affinity human monoclonal antibodies against influenza virus", *Nature*, 453: 667-672 (2008).
Wu, et al. "High-throughput sequencing of T-cell receptor gene loci for minimal residual disease monitoring in T Lymphooblastic Leukemia", Blood, 118: 2545 (Abstr) (2011).
Wu, Y-C. et al. "High-throughput immunoglobulin repertoire analysis distinguishes between human IgM memory and switched memory B-cell populations", *Blood Journal*, 116(7): 1070-1078, 22 pages (2010).
Wu et al. "Focused Evolution of HIV-1 Neutralizing Antibodies Revealed by Structures and Deep Sequencing", *Science*, 333: 1593-1602 (2011).
Wu, H.D. et al. "The Lymphocytic Infiltration in Calcific Aortic Stenosis Predominantly Consists of Clonally Expanded T Cells", *The Journal of Immunology*, 178(8): 5329-5339 (2007).
Xiong, et al. "Chemical gene synthesis: strategies, softwares, error corrections, and applications", *FEMS Microbiol Rev.*, 32(3): 522-540 (2008). doi: 10.1111/j.1574-6976.2008.00109.x. Epub Apr. 2, 2008.
Xiong, et al. "Non-polymerase-cycling-assembly-based chemical gene synthesis: strategies, methods, and progress", *Biotechnol Adv.*, 26(2): 121-134, Abstract Only (2008). Epub Nov. 7, 2007.
Xu, W. et al. "A Novel Universal Primer-Multiplex-PCR Method with Sequencing Gel Electrophoresis Analysis", *PLoS One*, 7(1): e22900, 10 pages (2012).
Yao, et al. "Analysis of the CDR3 length repertoire and the diversity of TCRα chain in human peripheral blood T Lymphocytes", *Cell Mol Immunol.*, 4(3): 215-220 (2007).
Yeh, et al. "Regulating DNA translocation through functionalized soft nanopores", *Nanoscale*, 4(8): 2685-4693, Abstract Only (2012). doi: 10.1039/c2nr30102d. Epub Mar. 15, 2012.
Yassai, M.B. et al. "A clonotype nomenclature for T cell receptors", *Immunogenetics*, 61:493-502 (2009).
York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.
Yu and Fu. "Tumor-infiltrating T lymphocytes: friends or foes?", *Lab Invest.*, 86(3): 231-245 (2006).
Zagnoni, et al. "Droplet Microfluidics for High-throughput Analysis of Cells and Particles", *Methods in Cell Biology*, Chapter 2, 102: 23-48 (2011).
Zehentner et al. "Minimal Disease Detection and Confirmation in Hematologic Malignancies: Combining Cell Sorting with Clonality Profiling", *Clinical Chemistry*, 52(3): 430-437 (2006).
Zeng et al. "High-performance single cell genetic analysis using microfluidic emulsion generator arrays", *Anal. Chem.*, 82(8):3183-3190 (2010).
Zhong, Q. et al. "Multiplex digital PCR: breaking the one target per color barrier of quantitative PCR", Lab Chip, 11:2167-2174 (2011).
Zhou et al. "Isolation of purified and live Foxp3+ regulatory T cells using FACS sorting on scatter plot", *J Mol Cell Biol.*, 2(3): 164-169 (2010). doi: 10.1093/jmcb/mjq007. Epub Apr. 29, 2010.
Zhu, et al. "Immune surveillance by CD8αα+ skin-resident T cells in human herpes virus infection", Nature, 497(7450):494-7 and Corrigendum (2013). doi: 10.1038/nature12110. Epub May 8, 2013.
Zimmerman and Mannhalter. "Technical aspects of quantitative competitive PCR", *Biotechniques*, 21: 268-279 (1996).
US 8,642,750, 02/2014, Robins et al. (withdrawn)

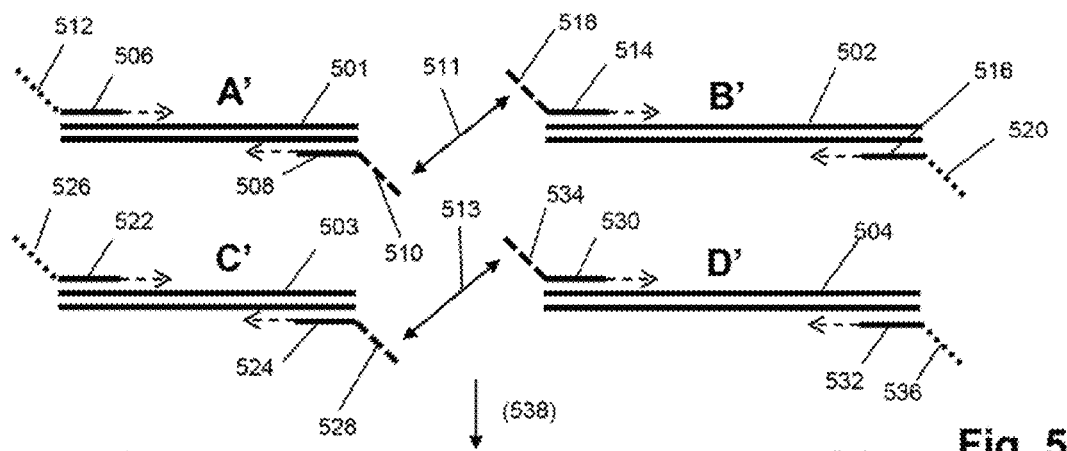
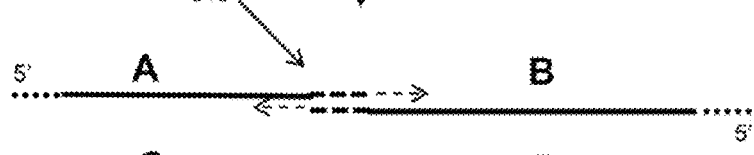
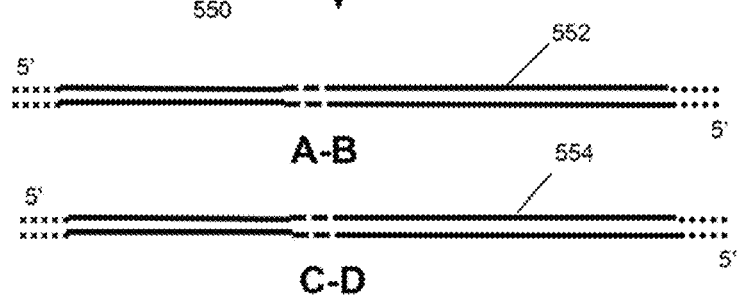

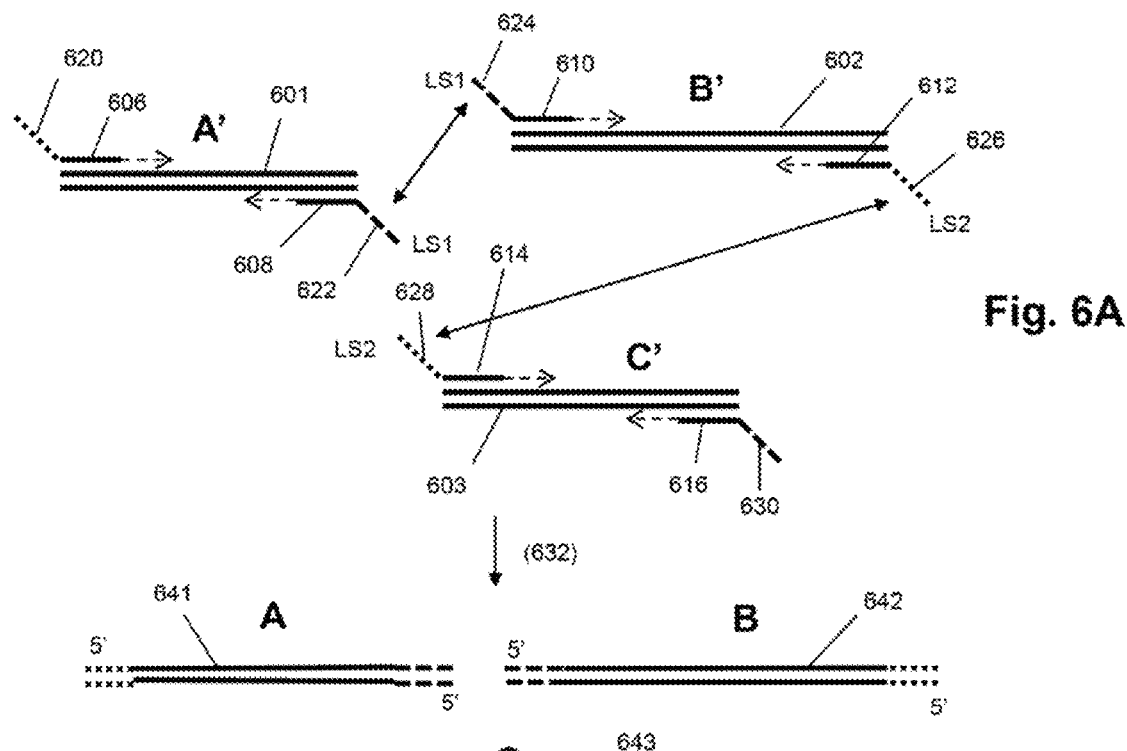
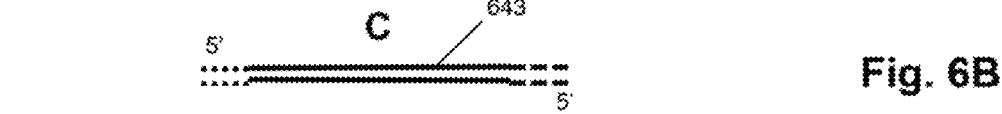
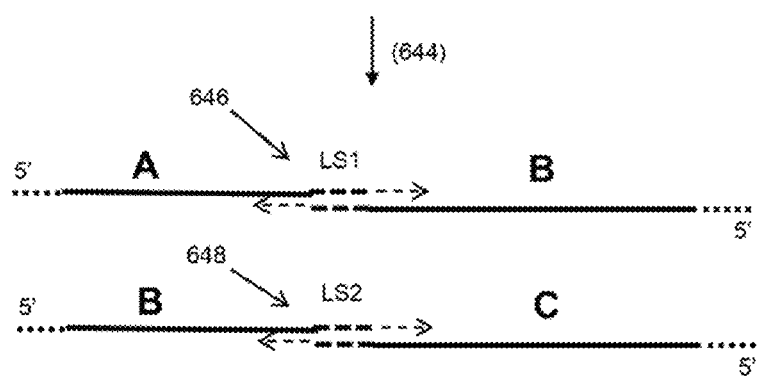
Fig. 6A
Fig. 6B
Fig. 6C

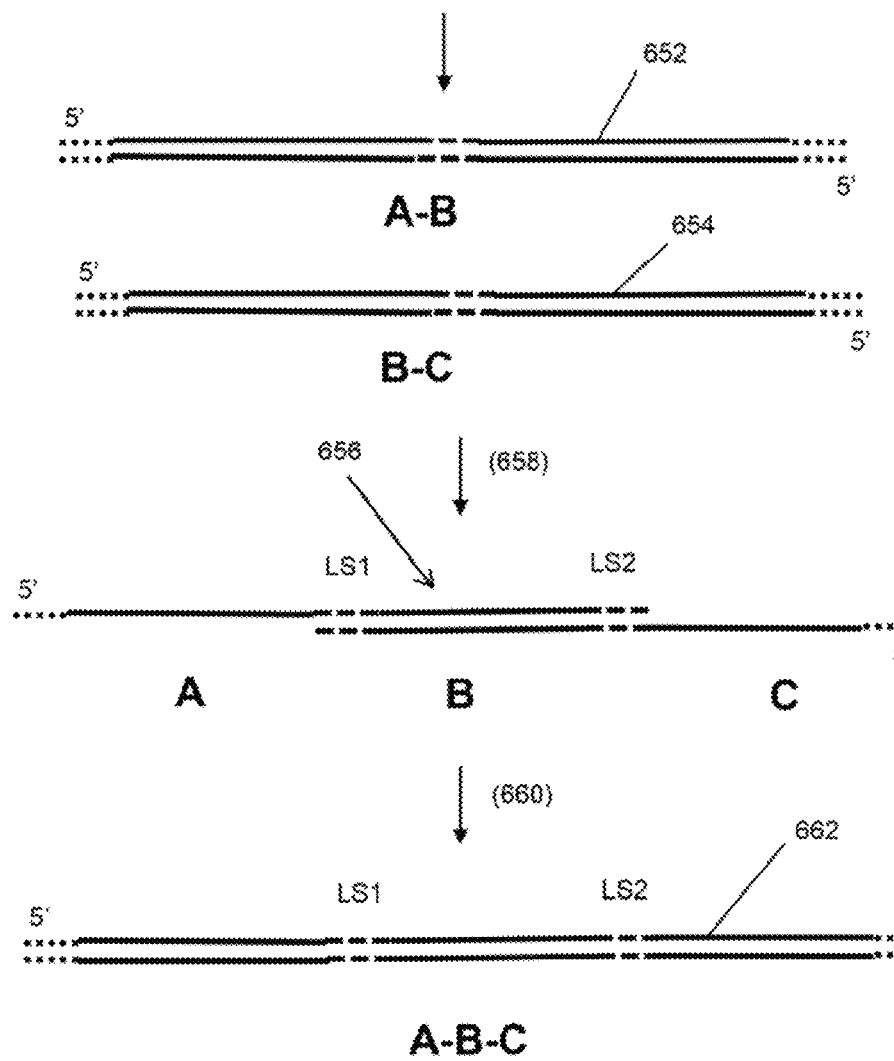

US 9,347,099 B2

SINGLE CELL ANALYSIS BY POLYMERASE CYCLING ASSEMBLY

This application is a and continuation of U.S. application Ser. No. 13/100,395 filed 4 May 2011 (now U.S. Pat. No. 8,507,205), which is a continuation-in-part of U.S. application Ser. No. 12/615,263 filed 9 Nov. 2009 (now U.S. Pat. No. 8,236,503), which claims the benefit of U.S. provisional application Ser. No. 61/112,693 filed 7 Nov. 2008, each of the foregoing applications being incorporated herein by reference in its entirety. U.S. application Ser. No. 13/100,395 also claims priority from U.S. provisional application Ser. No. 61/332,175 filed 6 May 2010, Ser. No. 61/446,822 filed 25 Feb. 2011, and Ser. No. 61/452,594 filed 14 Mar. 2011, all of which are incorporated herein by reference in their entireties.

BACKGROUND

Cytometry plays an indispensable role is many medical and research fields. Image-based and flow cytometers have found widespread use in these fields for counting cells and measuring their physical and molecular characteristics, e.g. Shapiro, Practical Flow Cytometry, 4th Edition (Wiley-Liss, 2003). In particular, flow cytometry is a powerful technique for rapidly measuring multiple parameters on large numbers of individual cells of a population enabling acquisition of statistically reliable information about the population and its subpopulations. The technique has been important in the detection and management of a range of diseases, particularly blood-related diseases, such as hematopoietic cancers, HIV, and the like, e.g. Woijciech, Flow Cytometry in Neoplastic Hematology, Second Edition (Informs Healthcare, 2010); Brown et al, Clinical Chemistry, 46: 8(B): 1221-1229 (2000). Despite this utility, flow cytometry has a number of drawbacks, including limited sensitivity in rare cell detection, e.g. Campana et al, Hematol. Oncol. Clin, North Am., 23(5); 1083-1098 (2009); limitations in the number of cell parameters that can be practically measured at the same time; and costly instrumentation.

In view of the above, it would be advantageous to many medical and research fields if there were available alternative methods and systems for making multiparameter measurements on large numbers of individual cells that overcame the drawbacks of current cytometric approaches.

SUMMARY OF THE INVENTION

The present invention is directed to methods for making multiparameter measurements of target nucleic acids in single cells of a population, particularly cells such, as lymphocytes that contain cell-specific recombined sequences. Aspects of the present invention are exemplified in a number of implementations and applications, some of which are summarized below and throughout the specification.

In one aspect the invention includes a method of analyzing a plurality target nucleic acids in each cell of a population comprising the steps of: (a) providing multiple reactors each containing a single cell in a polymerase cycling assembly (PCA) reaction mixture comprising a pair of outer primers and one or more pairs of linking primers specific for the plurality of target nucleic acids; (b) performing a PCA reaction in the reactors to form fusion products of the target nucleic acids in the reactors; and (c) sequencing the fusion products from the reactors to identify the target nucleic acids of each cell in the population.

In another aspect the invention includes a method of distinguishing multiple subpopulations of lymphocytes comprising the steps of: (a) providing multiple reactors each containing a single lymphocyte in a polymerase cycling assembly (PCA) reaction mixture comprising a pair of outer primers and one or more pairs of linking primers, one or more pairs of such primers being specific for one or more target nucleic acids and at least one pair of such primers being specific for a nucleic acid containing a clonotype; (b) performing a PCA reaction in each reactor to form a fusion product comprising the target nucleic acids and a clonotype of the lymphocyte therein; (c) sequencing the fusion products from the reactors; and (d) classifying each lymphocyte into a subpopulation by the target nucleic acids associated with its clonotype.

These above-characterized aspects, as well as other aspects, of the present invention are exemplified in a number of illustrated, implementations and applications, some of which are shown in the figures and characterized in the claims section that follows. However, the above summary is not intended to describe each illustrated embodiment or every implementation of the present invention.

BRIEF DESCRIPTIONS OF THE DRAWINGS

FIGS. 5A-5F illustrate a multiplex of pairwise assemblies of target sequences.

FIGS. 6A-6E illustrate a method of using PCA to link together three sequences.

DETAILED DESCRIPTION OF THE INVENTION

The practice of the present invention may employ, unless otherwise indicated, conventional techniques and descriptions of organic chemistry, molecular biology (including recombinant techniques), cell biology, and biochemistry, which are within the skill of the art. Such conventional techniques include, but are not limited to, sampling and analysis of blood cells, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A laboratory Manual Series* (Vols. I-IV); *PCR Primer: A Laboratory Manual; and Molecular Cloning: A Laboratory Manual* (all from Cold Spring Harbor Laboratory Press); and the like.

Figure 1:
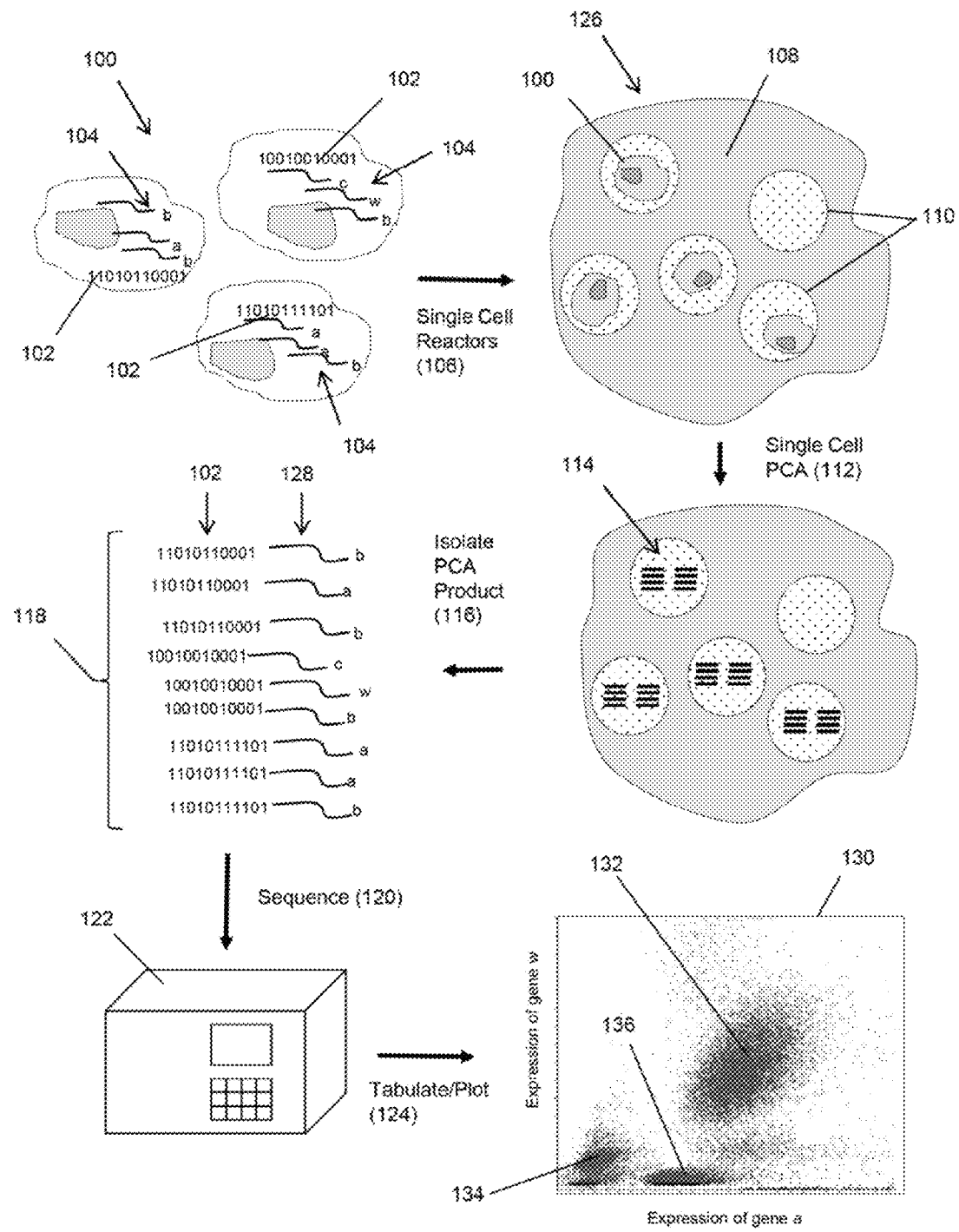
FIG. 1 illustrates steps of one embodiment of the method of the invention.

The invention provides a method of making measurements on individual cells of a population, particularly cells that have identifying nucleic acid sequences, such as lymphoid cells. In one aspect the invention provides a method of making multiparameter measurements on individual cells of such a population. An objective of assays of the invention, is to carry out a polymerase cycling assembly (PCA) reaction on individual cells to link their identifying nucleic acid sequences to other cellular nucleic acids of interest (referred to herein as "target nucleic acids"), the products of such, linking being referred to herein as "fusion products." After their generation, fusion products can be sequenced and tabulated to generate data, especially multiparameter data, for each cell of a population. In one aspect, such data may include gene expression data, data on the presence or absence of one or more predetermined genomic sequences, gene copy number data, or combinations of the foregoing. FIG. 1 gives an overview on one embodiment of the invention. Lymphoid cells (100) each have a distinct identifying nucleic acid (102), which in the figure is represented as a unique binary number. In one aspect, the identifying nucleic acids are the clonotypes of the lymphocytes. In addition, each cell has and/or expresses various nucleic acids of interest (104), or target nucleic acids, represented by the letters "a", "b", "c" and "w", which may be genomic DNA, expressed genes, or the like. Cells (100) are disposed (106) in single cell reactors (110), which in this example are illustrated as micelles of a water-in-oil emulsion (108), although a variety of single cell reactors may be used, including but not limited to, plates with arrays of nanoliter-volume wells, microfluidic devices, and the like, as described more fully below. In one aspect, single-cell emulsion (126) is generated using a microfluidic emulsion generator, such as disclosed by Zeng et al, Anal. Chem., 82: 3183-3190 (2010), or the like.

Reactors (110) contain a PCA reaction mixture that, for example, may comprise a nucleic acid polymerase, outer primers and linking primers (described more fully below), nucleoside triphosphates, a buffer solution, and the like. In some embodiments, a PCA reaction mixture may also include one or more cell lysing reagents, to access of such reagents to target nucleic acids. For each reactor (110) containing a cell, PCA reaction (112) generates fusion products (114) that may comprise one or more pairs of sequences, such that one member of the pair is the identifying nucleic acid of the cell in the reactor and the other member is a nucleic acid of interest, such as an expressed gene. In other embodiments, fusion products may comprise triplets of sequences, or higher order concatenations. In the method of the invention, a single kind of fusion product may be generated for each cell (or per reactor) or a plurality of different kinds of fusion products may be generated for each cell (or per reactor). Such plurality may be in the range of from 2 to 500, or from 2 to 200, or from 2 to 100, or from 2 to 20. In one embodiment, such plurality may be in the range of from 2 to 10.

After completion of PCA reaction (112), emulsion (126) is broken and fusion products (114) are isolated (116). Fusion products (114) are represented in FIG. 1 as conjugates (118) of identifying nucleic acids (102) and target nucleic acids (128). A variety of conventional methods may be used to isolate fusion products (114), including, but not limited to, column chromatography, ethanol precipitation, affinity purification after use of biotinylated primers, gel electrophoresis, or the like. As part of PCA reaction (112) or after isolation (116), additional sequences may be added to fusion products (114) as necessary for sequencing (120). Sequencing may be carried out using a conventional high-throughput instrument (122), e.g. Genome Analyzer IIx (Iliumina, Inc., San Diego), or the like. Data from instrument (122) may be organized and displayed (124) in a variety of ways. In particular, where target nucleic acids are selected gene expression products, e.g. mRNAs, plots may be constructed that display per-cell expression levels of selected gene for an entire population or subpopulation, in a manner similar to that for flow cytometry data, as illustrated by plot (130). Each cell is associated with a unique clonotype that is linked via the PCA reaction to genes expressed in the cell in a proportion related to their cellular abundance. Thus, by counting the number of expressed gene sequences linked to a specific clonotype sequence, one obtains a measure of expression for such gene in the cell associated with the specific clonotype. As illustrated in plot (130), three subpopulations of cells are indicated by the presence of separate clusters (132, 134, and 136) based on expression levels of gene w and gene a. In one aspect, whenever gene expression levels are monitored, at least one gene is selected as an internal standard for normalizing the expression measurements of other genes.

Polymerase Cycling Assembly (PCA) Reaction Formats

Polymerase cycling assembly (PCA) reactions permit a plurality of nucleic add fragments to be fused together to form a single fusion product in one or more cycles of fragment annealing and polymerase extension, e.g. Xiong et al, FEBS Micro biol. Rev., 32: 522-540 (2008). PCA reactions come in many formats. In one format of interest, PCA follows a plurality of polymerase chain reactions (PCRs) taking place in a common reaction volume, wherein each component PCR includes at least one linking primer that permits strands front the resulting amplicon to anneal to strands from another amplicon in the reaction and to be extended to form, a fusion product or a precursor of a fusion product. PCA in its various formats (and under various alternative names) is a well-known method for fragment assembly and gene synthesis, several forms of which are disclosed in the following references: Yon et al, Nucleic Acids Research, 17: 4895 (1989); Chen et al, J. Am. Chem. Soc., 116: 8799-8800 (1994); Stemmer et al, Gene, 164: 49-53 (1995); Hoover et al, Nucleic Acids Research, 30: e43 (2002); Xiong et al, Biotechnology Advances, 26: 121-134 (2008); Xiong et al, FEBS Microbiol. Rev., 32: 522-540 (2008); and the like.

Figure 2A:
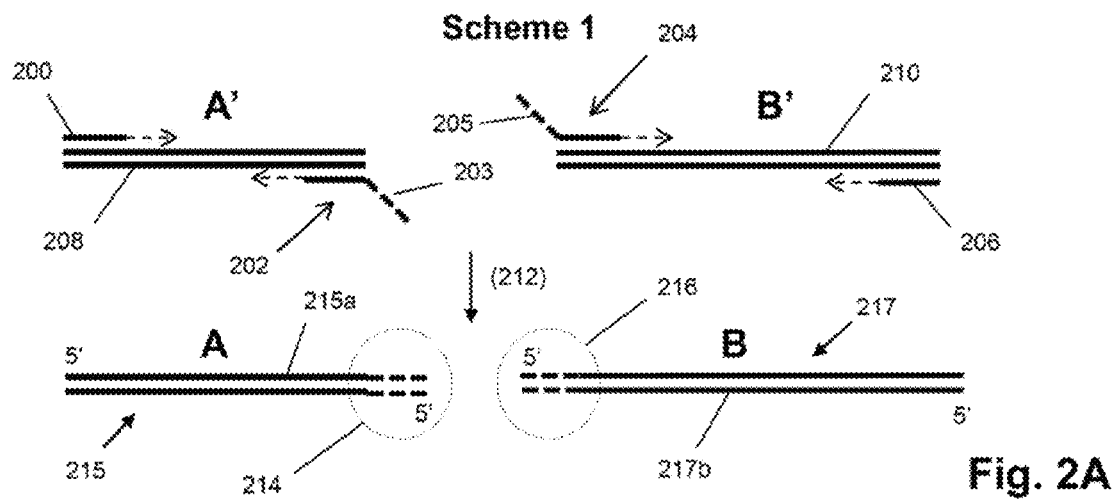
FIGS. 2A-2C illustrate a PCA scheme for linking target sequences where pairs of internal primers have complementary tails.
Figure 2B:
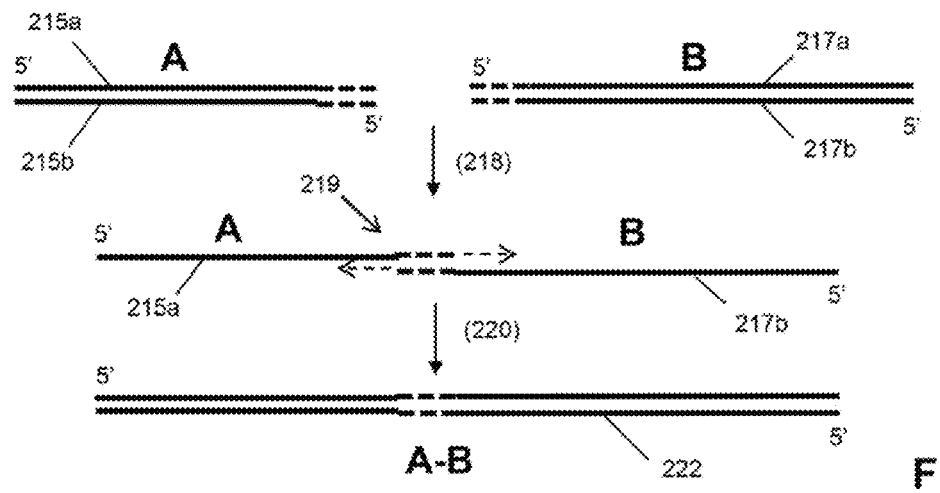
Figure 2C:
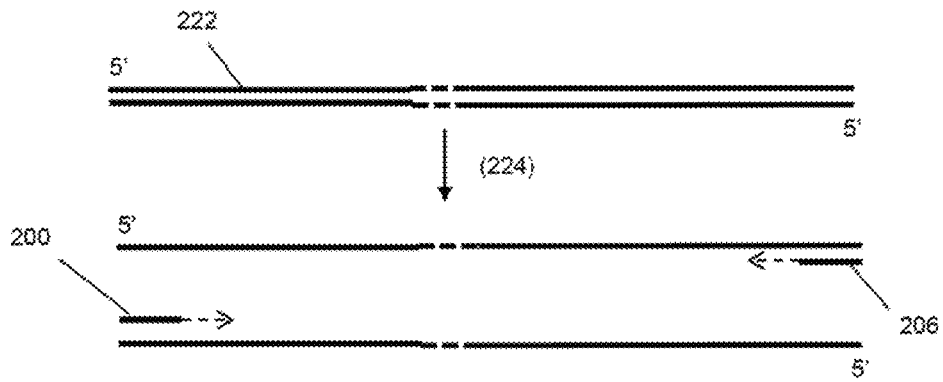

Some PCA formats useful in the present invention are described in FIGS. 2A-2C, 3A-3C, 4A-4C, 5A-5D, and 6A-6E. FIGS. 2A-2C illustrate an exemplary PCA scheme ("Scheme 1") for joining two separate fragments A' (208) and B' (210) into a single fusion product (222). Fragment A' (208) is amplified with primers (200) and (202) and fragment B' (210) is amplified with primers (206) and (204) in the same PCR mixture. Primers (200) and (206) are "outer" primers of the PCA reaction and primers (202) and (204) are the "inner" primers of the PCA reaction. Inner primers (202) and (204) each have a tail (203 and 205, respectively) that are not complementary to A' or B' (or adjacent sequences if A' and B' are segments imbedded in a longer sequence). Tails (203) and (205) are complementary to one another. Generally, such inner primer tails are selected for selective hybridization to its corresponding inner primer (and not elsewhere); but otherwise such tails may vary widely in length and sequence. In one aspect, such tails have a length in the range of from 8 to 30 nucleotides; or a length in the range of from 14 to 24 nucleotides. As the PCRs progress (212), product fragments A (215) and B (217) are produced that incorporate tails (203) and (205) into end regions (214) and (216), respectively. During the PCRs product fragments A (215) and B (217) will denature and some of the "upper" strands (215a) of A anneal (218) to lower strands (217b) of B and the 3' ends are extended (219) to form (220) fusion product A-B (222). Fusion product A-B (222) may be further amplified by an excess of outer primers (200) and (206). In some embodiments, the region of fusion product (222) formed from, tails (203) and (205) may include one or more primer binding sites for use in later analysis, such as high-throughput sequencing. Typically, in PDA reactions the concentrations of outer primers are greater than the concentrations of inner primers so that amplification of the fusion product continues alter initial formation. For example, in one embodiment for fusing two target nucleic acids outer primer concentration may be from about 10 to 100 times that of the inner primers, e.g. 1 µM for outer primers and 0.01 µM for inner primers. Otherwise, a PCA reaction may comprise the components of a PCR.

Figure 3A:
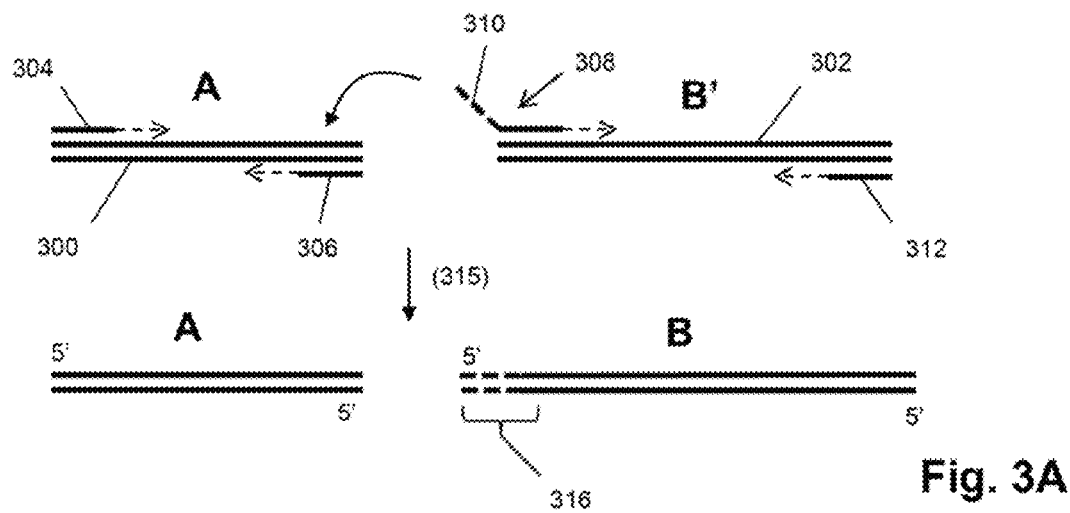
FIGS. 3A-3C illustrate a PCA scheme for linking target sequences where only one primer of each pair of internal primers has a tail mat is complementary to an end of a target sequence.
Figure 3B:
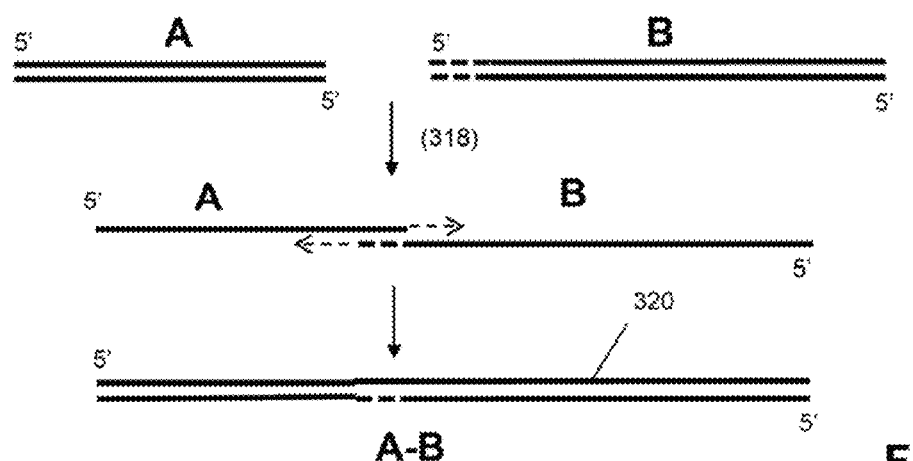
Figure 3C:
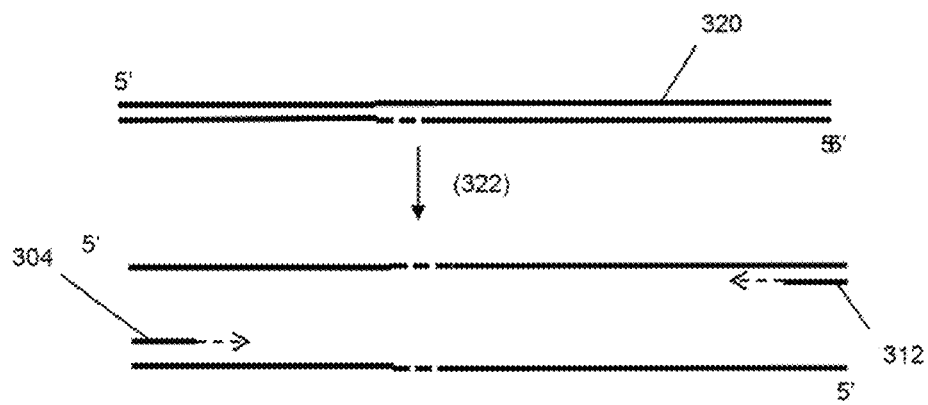

A variation of Scheme 1 is illustrated in FIGS. 3A-3C as Scheme 1(a). As above, fragment A (300) is amplified using primers (304) and (306) and fragment B' (302) is amplified using primers (308) and (312) in PCRs carried out in a common reaction mixture. Outer primers (304) and (312) are employed as above, and inner primer (308) has tail (310); however, instead of tail (310) being complementary to a corresponding tail on primer (306), it is complementary to a segment on the end of fragment A, namely, the same segment that primer (306) is complementary to. The PCRs produce (315) fragments A and B, where B is identical to B' (302) with the addition of segment (316) created by tail (310) of primer (308). As above, as temperature cycling continues (particularly as inner primers become exhausted), the upper fragments of fragment A anneal (318) to the lower fragment of fragment B and are extended to produce fusion product A-B (320), which may be further amplified using primers (304) and (312).

Figure 4A:
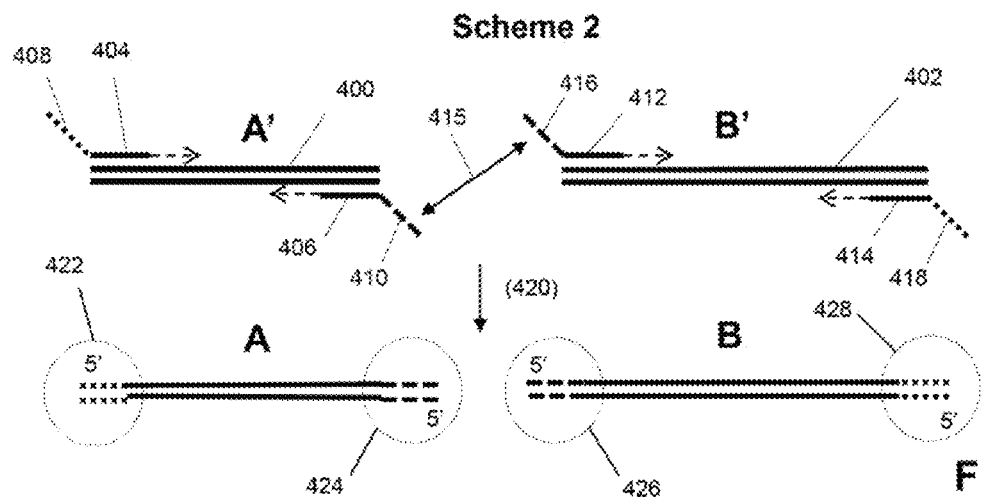
FIGS. 4A-4C illustrate a PCA scheme for linking target sequences where pairs of internal primers have complementary tails and external primers have tails for continued amplification of an assembled product by PCR.
Figure 4B:
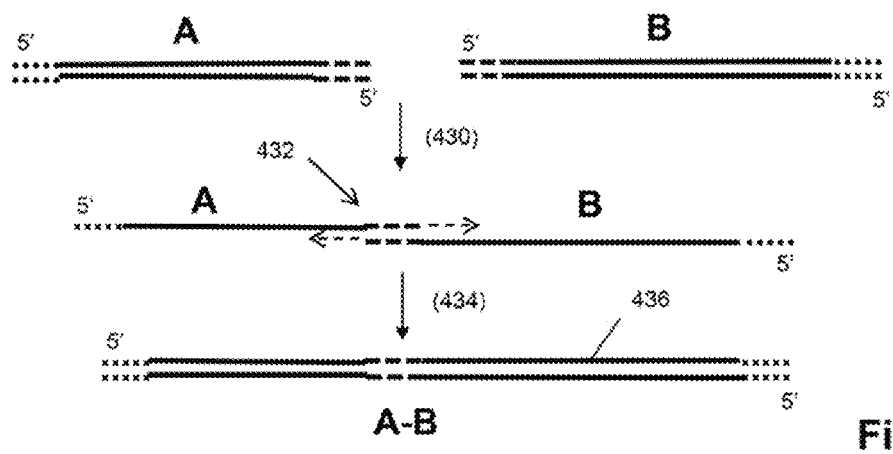
Figure 4C:
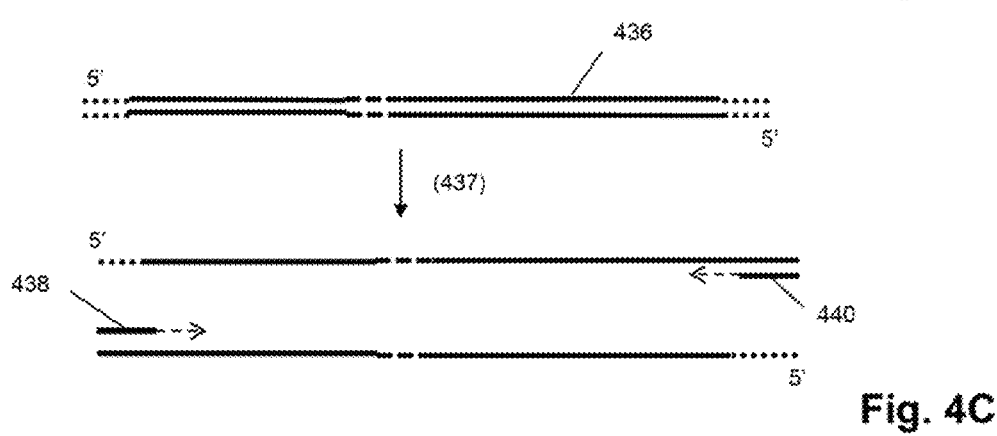

Another embodiment of a PCA that may be used with the invention ("Scheme 2") is illustrated in FIGS. 4A-4C. The embodiment is similar to that of FIGS. 2A-2C, except that outer primers (404) and (414) have tails (408) and (418), respectively, which permit further amplification of a fusion product with predetermined primers. As discussed more fully below, this embodiment is well-suited for multiplexed amplifications. Fragment A' (400) is amplified with primers (404) and (406), having tails (408) and (410), respectively, to produce fragment A, and fragment B' (402) is amplified with primers (412) and (414), having tails (416) and (418), respectively, to produce (420) fragment B. Tails (410 and 416) of inner primers (406 and 412) are selected to complementary (415) to one another. Ends of fragments A and B are augmented by segments (422, 424, 426 and 428) generated by tails (408, 410, 416 and 418, respectively). As with previously described embodiments, upper strands of fragment A anneal (430) to lower strands of fragment B and are extended (432) to form (434) fusion product A-B (436) that may be further amplified (437) using primers (438 and 440) that are the same as primers (404 and 414), but without tails.

As mentioned above, the embodiment of FIGS. 4A-4C, may be used in a multiplex PCA reaction, which is illustrated in FIGS. 5A-5D. There fragments A' (501), B' (502), C' (503), and D' (504) are amplified in PCRs in a common reaction mixture using primer sets (506 and 508) for fragment A', (514 and 516) for fragment B', (522 and 524) for C' and (530 and 532) for D'. All primers have tails: outer primers (506, 516, 522 and 532) each have tails (512, 520, 526 and 536, respectively) that permit both fragment amplification and subsequent fusion product amplification. Sequences of tails (512) and (520) may be the same or different from the sequences of tails (526) and (536), respectively. In one embodiment, the sequences of tails (512, 520, 526 and 536) are the same. Tails of inner primers (518 and 510) are complementary (511) to one another; likewise, tails of inner primers (528 and 534) are complementary (513) to one another. The above PCRs generate fragments A (541), B (542), C (543) and D (544), which further anneal (546) to one another to form complexes (548 and 550) which are extended to form fusion products A-B (552) and C-D (554), respectively.

Figure 5E:
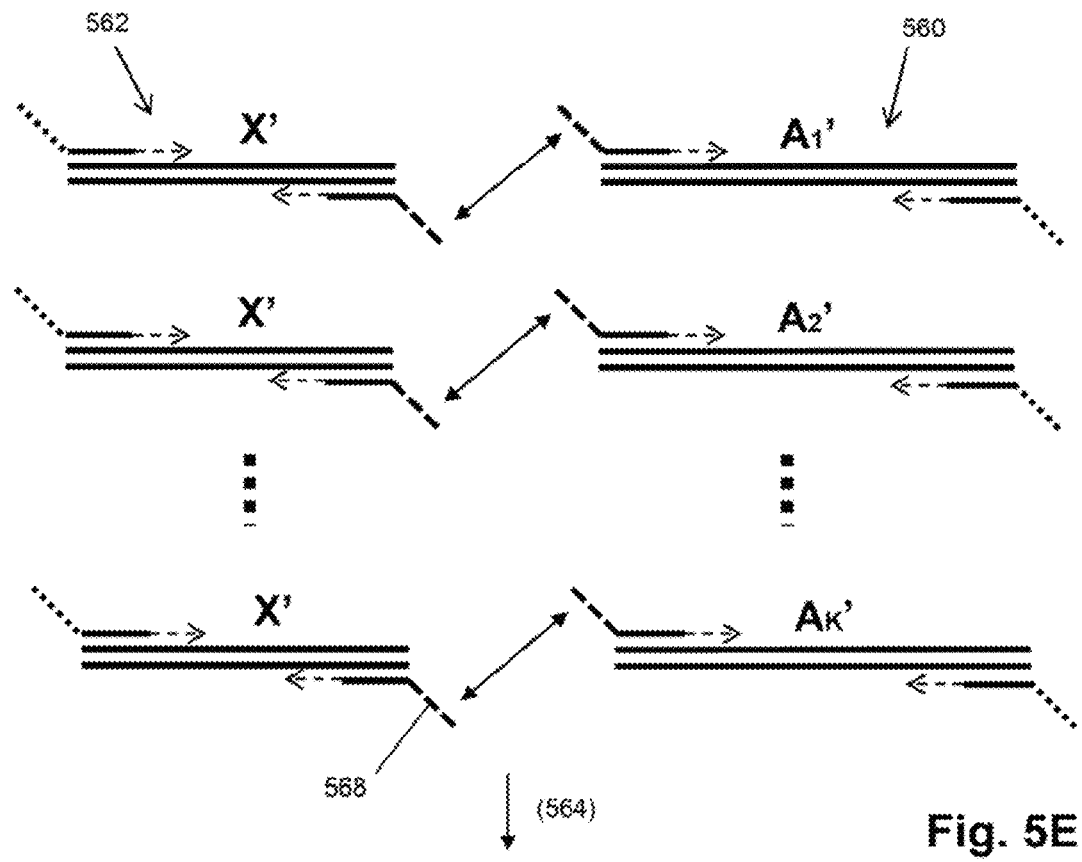
Figure 5F:
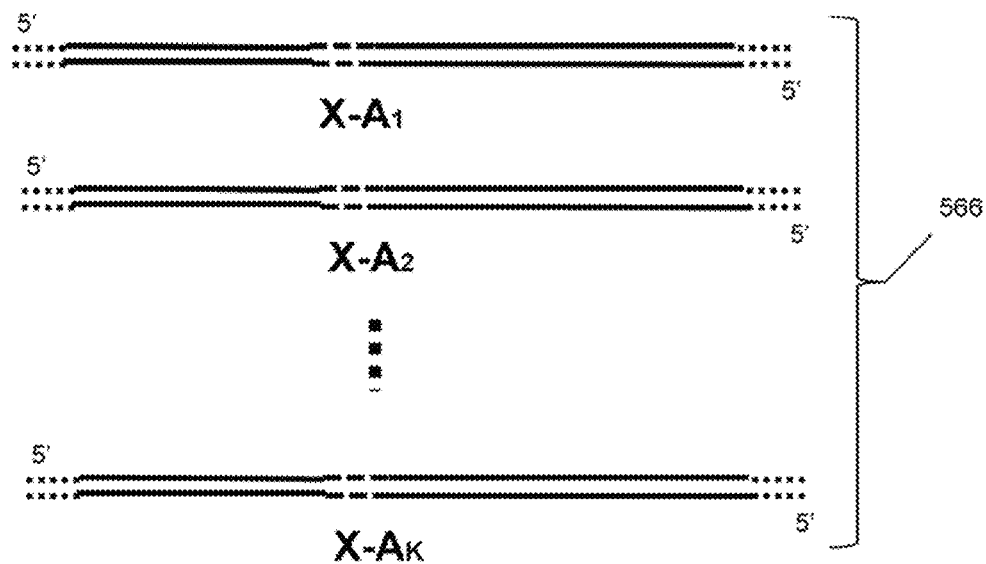

FIGS. 5E and 5F illustrate a generalization of the above embodiment in which multiple different target nucleic acids (560), $A_1'$, $A_2'$, ... $A_K'$, are linked to the same target nucleic acid, X' (562) to form (564) multiple fusion products X-$A_1$, X-$A_2$, ... X-$A_K$ (566). This embodiment is of particular interest when target nucleic acid, X, is a segment of recombined sequence of a lymphocyte, which can be used as a tag for the lymphocyte that it originates from. In one aspect, X is a clonotype, such as a segment of a V(D)J region of either a B cell or T cell. In one embodiment, a plurality of target nucleic acids. $A_1$, $A_2$, ... $A_K$, are fused to the clonotype of its cell of origin. In another embodiment, such plurality is between 2 and 1000; and in another embodiment, it is between 2 and 100; and in another embodiment, it is between 2 and 10. In PCA reactions of these embodiments, the concentration of inner primer (568) may be greater than those of inner primers of the various $A_1$ nucleic acids so that there is adequate quantities of the X amplicon to anneal with the many stands of the $A_1$ amplicons in accordance with a method, of the invention, the fusion products (566) are extracted from the reaction mixture (e.g. via conventional double stranded DNA purification techniques, such as available from Qiagen, or the like) and sequenced. The sequences of the outer primers may be selected to permit direct use for cluster formation without further manipulation for sequencing systems such as a Genome Analyzer (Illumina, San Diego, Calif.). In one aspect, X may be a clonotype and $A_1$, $A_2$, ... $A_K$ may be particular genes or transcripts of interest. After sequencing fusion products, per cell gene expression levels may be tabulated and/or plotted as shown in FIG. 1.

In addition to multiplexed PCA reactions in a parallel sense to simultaneously generate multiple binary fusion products, as illustrated in FIGS. 6A-6E, PCA reactions may be multiplexed in a serial sense to assemble multi-subunit fusion products. As shown in FIG. 6A, fragments A' (601), B' (602) and C' (603) are amplified in a common PCR mixture with primer sets (606 and 608) for A', (610 and 612) for B' and (614 and 616) for C'. All primers have tails: (i) tails (620 and 630) of outer primers (606 and 616) are selected for amplification of outer fragments A' and C' and further amplification of three-way fusion product A-B-C (662) shown in FIG. 6E; (ii) tails (622 and 624) of inner primers (608 and 610) are complementary to one another; and (iii) tails (628 and 626) of inner primers (654 and 612) are complementary to one another. The PCRs generate (632) fragments A (641), B (642) and C (643), which in the reaction form (644) complexes (646 and 648) comprising segments LS1 and LS2, respectively, which in turn are extended to form (650) fusion products A-B (652) and B-C (654). These fusion products are denatured and some cross anneal (658) to one another by way of the common B fragment (656) to form a complex which is extended (660) to form fusion product A-B-C (662). Exemplary, PCA reaction, conditions for the above reaction may be as follows: 39.4 µL distilled water combined with 10 µL of 10× buffer (100 mM Tris-HCl, pH 8.3, 500 mM KCl, 15 mM MgCl2, and 0.01% gelatin), 2 µL of a 10 mM solution of each of the dNTPs, 0.5 µL of Taq polymerase (5 units/µL), 1 µL of each outer primer (from a 100 µM stock solution) and 10 µL of each inner primer (from a 0.1 µM stock solution).

Single Cell Analysis

As mentioned above, in one aspect of the invention, cells from a population are disposed in reactors each containing a single cell. This may be accomplished by a variety of large-scale single-cell reactor platforms known in the art, e.g. Clarke et al, U.S. patent publication 2010/0255471; Mathies et al, U.S. patent publication 2010/0285975; Edd et al, U.S. patent publication 2010/0021984; Colston et al, U.S. patent publication 2010/0173394; Love et al, international patent publication WO2009/145925; Muraguchi et al, U.S. patent publication 2009/0181859; Novak, et al, Angew. Chem. Int. Ed., 50: 390-395 (2011); and the like, which are incorporated herein by reference. In one aspect, cells are disposed in wells of a microwell array where reactions, such as PCA reactions, take place; in another aspect, cells are disposed in micelles of a water-in-oil emulsion, where micelles serve as reactors. Micelle reactors generated by microfluidics devices, e.g. Mathies et al (cited above) or Edd et al (cited above), are of particular interest because uniform-sized micelles may be generated and cells encounter lower shear and stress than in bulk emulsification processes.

Cells of a sample may be suspended in a PCA reaction mixture prior to disposition into reactors. In one aspect, a PCA reaction mixture is substantially the same as a PCR reaction mixture with inner at least one pair of inner primers and at least one pair of outer primers. Optionally, a PCA reaction mixture may comprise a lysing agent to facilitate access of the PCA reagents to target nucleic acids of isolated cells. Lysing conditions of a PCA reaction may vary widely and may be based on the action of heat detergent, protease, alkaline, or combinations of such factors. The following references provide guidance for selection of single-cell lysing conditions where a polymerase-based amplification, such as PCA, is employed; Throuhill et al, Prenatal Diagnosis, 21: 490-497 (2001); Kim et al, Fertility and Sterility, 92: 814-818 (2009); and the like. Exemplary lysis conditions for use with PCA reactions are as follows: 1) cells in $H_2O$ at 96° C. for 15 min, followed by 15 min at 10° C.; 2) 200 mM KOH, 50 mM dithiotheitol, heat to 65° C. for 10 min; 3) for 4 µL protease-based lysis buffer: 1 µL of 17 µM SDS combined with 3 µL of 125 µg/mL proteinase K, followed by incubation at 37° C. for 60 min, then 95° C. for 15 min (to inactivate the proteinase K); 4) for 10 µL of a detergent-based lysis buffer: 2 µL $H_2O$, 2 µL 250 ng/µl, poly A, 2 µL 10 mM EDTA, 2 µL 250 mM dithiothreitol, 2 µL 0.5% N-laurylsarcosin salt solution. Single-cell analysis platforms, incubation times, lysis buffer and/or PCA reaction other components, their concentrations, reactions volumes and the like, are design choices that are optimized for particular applications by one of ordinary skill in the art.

Nucleic Acid Sequencing Techniques

Any high-throughput technique for sequencing nucleic acids can be used in the method of the invention. DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, sequencing by synthesis using allele specific hybridization to a library of labeled clones that is followed by ligation, real time monitoring of the incorporation, of labeled nucleotides during a polymerization step, polony sequencing, SOLID sequencing, and the like. These sequencing approaches can thus be used to sequence fusion products of target nucleic acids of interest and clonotypes based on T-cell receptors (TCRs) and/or B-cell receptors (BCRs). In one aspect of the invention, high-throughput methods of sequencing are employed that comprise a step of spatially isolating individual molecules on a solid surface where they are sequenced in parallel. Such solid surfaces may include non-porous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al. Science, 323: 133-138 (2009)), or bead arrays (as with SOLID sequencing or polony sequencing, e.g. Kim et al, Science, 316: 1481-1414 (2007)). In another aspect, such methods comprise amplifying the isolated molecules either before or after they are spatially isolated on a solid surface. Prior amplification may comprise emulsion-based amplification, such as emulsion PCR, or rolling circle amplification. Of particular interest is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081B1; which are incorporated by reference. In one embodiment, individual molecules disposed and amplified on a solid surface form clusters in a density of at least $10^5$ clusters per $cm^2$; or in a density of at least $5 \times 10^5$ per $cm^2$; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

In one aspect of the invention, multiplex PCR is used to amplify members of a mixture of nucleic acids, particularly mixtures comprising recombined immune molecules such as T cell receptors, B cell receptors, or portions thereof. Guidance for carrying out multiplex PCRs of such immune molecules is found in the following references, which are incorporated by reference: Morley, U.S. Pat. No. 5,296,351; Gorski, U.S. Pat. No. 5,837,447; Dau, U.S. Pat. No. 6,087,096; Von Dongen et al, U.S. patent publication 2006/0234234; European patent publication EP 1544308B1; Faham et al, U.S. patent publication 2010/0151471; Han, U.S. patent publication 2010/0021896; Robins et al, U.S. patent publication 2010/033057; and the like. Such amplification techniques are readily modified by those of ordinary skill in the art to supply outer primers and linking primers of the invention.

Cancer-Related Applications

Detecting cross-lineage rearrangements. Some types of otherwise uncommon rearrangements are common in some cancers and thus can be used to associate them with tumor. For example, cross lineage rearrangements, like T cell receptor (α, β, γ and/or δ) in B cells or B cell receptor (IgH, IgK, and/or IgL) in T cells are common, especially in ALL. The presence of cross lineage rearrangements is likely to support a malignant origin of the clonotype. Demonstrating cross lineage rearrangement can be done by performing linked PCR on a cell by cell basis. Linked PCR amplifies two distinct targets (for example IgH and TCRβ) and create a linked molecule between the two amplified targets. These targets from all the amplified cells can be then pooled and sequenced without losing the information as to whether the two targets are expressed in the same or different cells. In order to get amplification even in the absence of the other rearrangement, another competing product may be used. For example, for B cells, IgH amplification will always occur while the cross lineage TCRβ may or may not occur. Two competing set of primers can be used for the amplification of TCRβ: one that amplifies the rearranged sequences and the other the germ line sequences. Optionally, the two competing sets can be used at different concentrations allowing the rearranged sequence to compete more efficiently when present in the cell. All the cells would have their IgH and TCRβ products amplified and linked, and sequencing would be used to identify those cells with cross lineage rearrangement. Methods for achieving linked PCR are disclosed above. One method to detect cells that do not have functional sequences uses the linked PCR technique mentioned above. In this case, the linking has to occur for the two alleles of the same target. For this purpose, 3 stage PCR can be performed. The first PCR of an immune cell genomic rearrangement is done from one cell with a set of primers (primer A and B) that allow the rearrangement of both alleles to be amplified. Primers A and B are then removed (e.g. by dilution) and a portion of these PCR products can be re-amplified with a second set of primers (C and D) which also allow the same product to be amplified. Primers C and B can additionally be designed, to include a sequence homology at their 5' termini that allows these 2 PCR products (from A/B and from C/D) to anneal to each other and extend to produce a linked, product. After removing primers from this reaction, the two PCR products can be mixed and re-amplified by PCR using primers A and D. The result is a linking of the two products, and in 50% of molecules they will carry both alleles. Sequencing would identify high frequency linked non-functional sequences. Specific high frequency non-functional sequences that are consistently linked to a second non-functional sequence are indicative of the potential cancer cell In addition to serving as a marker of cells that have become cancerous IgH is often one of the two pathological translocation partners in lymphoid neoplasms. One example is the t(11:14) that puts the J segment of IgH in close proximity to the cycline D1 (CCND1) gene resulting in its overexpression. This rearrangement which is referred to as BCL1-IgH occurs in as many as 60-70% of mantle cell lymphoma as well as other lymphoid neoplasms (e.g., 20% of multiple myeloma). Another example is t(14:18) that puts the J segment of IgH in close proximity to BCL2 resulting in its over expression. This rearrangement occurs in up to 90% of follicular lymphoma and 20% of large B cell lymphoma. These rearrangements are typically identified by cytogenetics, Southern blotting, or FISH. PCR has the potential to identify rearrangement at very high sensitivity and specificity as shown by BCR-ABL for the detection of Philadelphia chromosome. Different PCR techniques have been used to the assessment of translocations relevant to lymphoma, with the recently introduced real time PCR (e.g. for BCL2-IgH) being probably the most advanced. There are a few features of BCL1-IgH and BCL2-IgH that make their detection less sensitive and specific, than that of BCR-ABL. First, in contrast to BCR-ABL, BCL1-IgH and BCL2-IgH do not generate a fission protein, and there is no splicing event that generates predictable molecular structure. Instead the breakpoints may span a large region. There are common breakpoints that allow the detection of up to 88% of BCL2-IgH using a combination, of primers and ~40% of the BCL1-IgH. This results in missing some patients that have the translocation. Second, these rearrangements may be present in normal individuals that would never get cancer. For example, BLC2-IgH translocation has been found at the level, of ~$10^{-5}$ in a large fraction of the normal individuals with over ~4% carrying BCL2-IgH at a frequency of >1/25 K. The frequency of BCL2-IgH gets higher with increasing age. It is also hypothesized that different people may have distinct levels of "background" translocation. Presumably the presence of this translocation in normal sample is due to the fact that tumorgenesis is a multi-step process and the BCL2-IgH is not sufficient for tumors to emerge. The presence of this low level background puts a limit on the sensitivity of detection.

Amplification of with a pool of the J primers complementary to all the J segments and primers complementary to the regions upstream of the BCL1 or BCL2 translocation breakpoints can be sequenced. This can generate a method for sensitive detection of these translocations and the cancer cells they appear in. First, deep sequencing of individual isolated molecules (e.g. 100 K or 1 million, reads) can allow the detection of the appropriate sequences from a small number of cells in a background of amplifications of other loci. In addition, the problem of the background translocations in normal individuals may ameliorate the problem that real time PGR suffer from. There is evidence that, at least in some cases, the background translocations are not clonal, but rather appear repeatedly in the same patient. Using sequencing one can distinguish the different translocation events to obtain frequency of the independent translocation events. Since the breakpoint of different translocations is likely to be distinct translocation events can be distinguished from each other. Alternatively or additionally, a linking PCR using the translocation with a B or T cell receptor gene can be done to provide a unique barcode for the translocation. The linking can also be done statistically using a set of dilution samples as described above.

Similarly additional data relating to the status of the cell containing the cancer-related clonotype can be used to predict likelihood of recurrence. For example, the presence of certain markers (surface or non-surface) can be an indication of the functional status of the cell and hence the likelihood of recurrence. Sequencing before and after the capture of cells with the relevant markers can determine the fraction of cells with the cancer clonotype that carry the relevant markers. Similarly some markers relevant to the likelihood of recurrence (e.g., expression of some gene relating to cell growth) can be assessed at the RNA level. This can be done by several methods including linking PCR as described above. Finally, it is possible that the level of immune receptor specific RNA in the tumor cell can have functional consequence and association with the likelihood of recurrence. This level can be assessed by doing linking PCR between a control gene 1 that can link to either the immune receptor rearrangement or control gene 2. The relative fraction of the two products can be indicative of the relative amount of the RNA in the cell. Another method involves comparing the RNA level to the DNA level of the immune receptor rearrangement. The frequency of the cancer-specific clonotype in the DNA identifies the relative level of the cancer-specific clonotype. The frequency of the same clonotype can then be assessed from RNA, and the relative frequency in RNA and in DNA can be followed. A change in this relative frequency can be indicative of a change in the likelihood of recurrence.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

DEFINITIONS

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, 6$^{th}$ edition (Saunders, 2007).

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-21.55 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Clonotype" means a recombined nucleotide sequence of a T cell or B cell encoding a T cell receptor (TCR) or B cell receptor (BCR), or a portion thereof. In one aspect, a collection of all the distinct clonotypes of a population of lymphocytes of an individual is a repertoire of such population, e.g. Arstila et al. Science, 286: 958-961 (1999); Yassai et al, Immuoogenetics, 61: 493-502 (2009); Kedzierska et al, Mol. Immunol., 45(3); 607-618 (2008); and the like. A "clonotype profile," or "repertoire profile," is a tabulation or representation of clonotypes of a population of T cells and/or B cells (such as a peripheral blood sample containing such, cells) that includes substantially all of the repertoire's clonotypes and their relative abundances. As used herein, "clonotype profile," "repertoire profile," and "repertoire" are used interchangeably. (That is, the term "repertoire" as discussed more fully below, means a repertoire measured from a sample of lymphocytes). In one aspect of the invention, clonotypes comprise portions of an immunoglobulin heavy chain (IgH) or a TCR β chain. In other aspects of the invention, may be based on other recombined molecules, such as immunoglobulin light chains or TCRα chains, or portions thereof.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

"Kit" refers to any delivery system for delivering materials or reagents for carrying out a method of the invention. In the contest of reaction assays, such delivery systems include systems that allow for the storage, transport, or delivery of reaction reagents (e.g., primers, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains primers.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 μm to about 0.1 μm. Microfluidics devices typically have volume capacities in the range of from 1 μL to a few nL, e.g. 10-100 nL. The fabrication and operation of microfluidics devices are well-known in the art as exemplified by the following references that, are incorporated by reference: Ramsey, U.S. Pat. Nos. 6,001,229; 5,858, 195; 6,010,607; and 6,033,546; Soane et al, U.S. Pat. Nos. 5,126,022 and 6,054,034; Nelson et al, U.S. Pat. No. 6,613, 525; Maher et al, U.S. Pat. No. 6,399,952; Ricco et al, International patent publication. WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. PCR reaction volumes typically range from a few hundred nanoliters, e.g. 200 nL, to a few hundred μL, e.g. 200 μL. "Reverse transcription PCR," or "RT-PCR," means a PCR that is preceded by a reverse transcription reaction mat converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al. Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction, mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. Anal. Biochem., 273: 221-228 (1999) (two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polymerase cycling assembly" or "PCA" reaction (also referred to herein as "linked PCR") means a PCR that comprises at least one pair of outer primers and at least one pair of inner primers. An inner primer has a 3' portion that is complementary to a target nucleic acid (or its complement) and a 5' portion that is complementary to the 5' portion of another inner primer corresponding to a different target nucleic acid.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Repertoire" means a set of distinct recombined nucleotide sequences that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. Member nucleotide sequences of a repertoire are referred to herein, as a "clonotype." In one aspect, a repertoire comprises any segment of nucleic acid, common to a T cell or a B cell population which has undergone somatic recombination during the development of TCRs or BCRs, including normal or aberrant (e.g. associated with cancers) precursors thereof, including, but not limited to, any of the following: an immunoglobulin heavy chain (IgH) or subsets thereof (e.g., an IgH variable region, CDR3 region, or the like), an immunoglobulin light chain or subsets thereof (e.g. a variable region, CDR region, or the like), T cell receptor α chain or subsets thereof, T cell receptor β chain or subsets thereof (e.g. variable region, CDR3, V(D)J region, or the like), a CDR (including CDR1, CDR2 or CDR3, of either TCRs or BCRs, or combinations of such CDRs), V(D)J regions of either TCRs or BCRs, hypermutated regions of IgH variable regions, or the like. In one aspect, a repertoire is selected so that its diversity (i.e. the number of distinct nucleic acid sequences in the set) is large enough so that substantially every T cell or B cell or clone thereof in an individual carries a unique nucleic acid sequence of such repertoire. That is, in accordance with the invention, a practitioner may select for defining clonotypes a particular segment or region of recombined nucleic acids that encode TCRs or BCRs that do not reflect the full diversity of a population of T cells or B cells; however, preferably, clonotypes are defined so that they do reflect the diversity of the population of T cells and/or B cells from which they are derived. That is, preferably each different clone of a sample has different clonotype. In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined, by cell surface markers, or the like. In one embodiment, a repertoire of human TCR β chains comprises a number of distinct nucleotide sequences in the range of from $0.3 \times 10^6$ to $1.8 \times 10^6$, or in the range of from $0.5 \times 10^6$ to $1.5 \times 10^6$, or in the range of from $0.8 \times 10^6$ to $1.2 \times 10^6$. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In a particular embodiment, a repertoire of the invention comprises a set of nucleotide sequences encoding substantially all segments of the V(D)J region of an IgH chain. In one aspect, "substantially all" as used herein means every segment having a relative abundance of 0.001 percent or higher; or in another aspect, a relative abundance of 0.0001 percent or higher. In another particular embodiment, a repertoire of the invention comprises a set of nucleotide sequences that, encodes substantially all segments of the V(D)J region of a TCR β chain. In another embodiment, a repertoire of the invention comprises a set of nucleotide sequences having lengths in the range of from 25-200 nucleotides and including segments of the V, D, and J regions of a TCR β chain. In another embodiment, a repertoire of the invention comprises a set of nucleotide sequences having lengths in the range of from 25-200 nucleotides and including segments of the V, D, and J regions of an IgH chain. In another embodiment, a repertoire of the invention comprises a number of distinct nucleotide sequences that is substantially equivalent to the number of lymphocytes expressing a distinct IgH chain. In another embodiment, a repertoire of the invention comprises a number of distinct nucleotide sequences that is substantially equivalent to the number of lymphocytes expressing a distinct TCR β chain. In still another embodiment, "substantially equivalent" means that with ninety-nine percent probability a repertoire of nucleotide sequences will include a nucleotide sequence encoding an IgH or TCR β or portion thereof carried or expressed by every lymphocyte of a population of an individual at a frequency of 0.001 percent or greater. In still another embodiment, "substantially equivalent" means that with ninety-nine percent probability a repertoire of nucleotide sequences will include a nucleotide sequence encoding an IgH or TCR β or portion thereof carried or expressed by every lymphocyte present at a frequency of 0.0001 percent or greater. The foregoing sets of clonotypes are sometimes referred to herein as representing the "full repertoire" of IgH and/or TCRβ sequences.

What is claimed is:

1. A method of determining by single cell analysis the nucleotide sequences of fusion products comprising a plurality of linked nucleic acid molecules encoding at least two chains of a T-cell or B-cell immune receptor of a patient, the method comprising the steps of:

(a) separating single T-cells or B-cells from a sample comprising T-cells or B-cells of the patient among a plurality of reactors each containing a polymerase cycling assembly (PCA) reaction mixture comprising a pair of outer primers and one or more pairs of linking primers, at least one pair of such outer and linking primers being specific for a first nucleic acid molecule encoding one chain of an immune receptor and one or more pairs of such outer and linking primers being specific for a second nucleic acid molecule encoding another chain of the immune receptor, wherein both of said nucleic acid molecules have recombined nucleic acid sequences of a B-cell encoding a B-cell receptor or portion thereof or both of said nucleic acid molecules have recombined nucleic acid sequences of a T-cell encoding a T-cell receptor or portion thereof, respectively;

(b) performing a PCA reaction in the reactors to form a plurality of different kinds of fusion products comprising a plurality of different nucleic acid molecules encoding the immune receptor chains of the single T-cell or B-cell;

(c) spatially isolating individual molecules of said fusion products; and (d) sequencing the spatially isolated fusion product molecules to obtain nucleotide sequences of fusion products comprising a plurality of linked nucleic acid molecules encoding at least two chains of a T-cell or B-cell immune receptor of a patient.

2. The method of claim 1 wherein said plurality of reactors are aqueous micelles of a water-in-oil emulsion.

3. The method of claim 2 wherein said water-in-oil emulsion is generated by a microfluidics device.

4. The method of claim 1 further comprising a step of lysing said single T-cell or B-cell in said reactors prior to said step of performing said PCA reaction.

5. The method of claim 1 wherein said plurality of reactors each contain a T-cell and wherein the first nucleic acid molecule encoding one chain of an immune receptor is from an TCRα gene and the second nucleic acid molecule encoding another chain of an immune receptor is from an TCRβ gene.

6. The method of claim 1 wherein said plurality of reactors each contain a B-cell and wherein the first nucleic acid molecule encoding one chain of an immune receptor is from an IgH gene and the second nucleic acid molecule encoding another chain of an immune receptor is from an IgK gene.

7. The method of claim 1 wherein said plurality of reactors each contain a B-cell and wherein the first nucleic acid molecule encoding one chain of an immune receptor is from an IgH gene and the second nucleic acid molecule encoding another chain of an immune receptor is from an IgL gene.

8. A method of determining by single cell analysis the nucleotide sequences of fusion products comprising a plurality of linked nucleic acid molecules encoding at least two chains of a T-cell or B-cell immune receptor of a patient, the method comprising the steps of:

(a) separating single T-cells or B-cells from a sample comprising T-cells or B-cells of the patient among a plurality of reactors each containing a polymerase cycling assembly (PCA) reaction mixture comprising a pair of outer primers and one or more pairs of linking primers, at least one pair of such outer and linking primers being specific for a first nucleic acid molecule encoding one chain of an immune receptor and one or more pairs of such outer and linking primers being specific for a second nucleic acid molecule encoding another chain of the immune receptor, wherein both of said nucleic acid molecules have recombined nucleic acid sequences of a B-cell encoding a B-cell receptor or portion thereof or both of said nucleic acid molecules have recombined nucleic acid sequences of a T-cell encoding a T-cell receptor or portion thereof, respectively;

(b) lysing the single T-cells or B-cells in the reactors;

(c) performing a PCA reaction in the reactors to form a plurality of different kinds of fusion products comprising a plurality of different nucleic acid molecules encoding the immune receptor chains of the single T-cells or B-cells;

(d) spatially isolating individual molecules of said fusion products; and (e) sequencing the spatially isolated fusion product molecules to obtain nucleotide sequences of fusion products comprising a plurality of linked nucleic acid molecules encoding at least two chains of a T-cell or B-cell immune receptor of a patient.

9. The method of claim 8 wherein said plurality of reactors are aqueous micelles of a water-in-oil emulsion.

10. The method of claim 9 wherein said plurality of reactors each contain a T-cell and wherein the first nucleic acid molecule encoding one chain of an immune receptor is from an TCRα gene and the second nucleic acid molecule encoding another chain of an immune receptor is from an TCRβ gene.

11. The method of claim 8 wherein said nucleic acid molecules are RNA.

12. The method of claim 10 wherein said sample is from a patient with an autoimmune disease, an infectious disease or a cancer.

13. The method of claim 9 wherein said plurality of reactors each contain a B-cell and wherein the first nucleic acid molecule encoding one chain of an immune receptor is from an IgH gene and the second nucleic acid molecule encoding another chain of an immune receptor is from an IgK gene.

14. The method of claim 13 wherein said sample is from a patient with an autoimmune disease, an infectious disease or a cancer.

15. The method of claim 9 wherein said plurality of reactors each contain a B-cell and wherein the first nucleic acid molecule encoding one chain of an immune receptor is from an IgH gene and the second nucleic acid molecule encoding another chain of an immune receptor is from an IgL gene.

16. The method of claim 8 wherein said plurality of reactors are an array of nanoliter-volume wells.

17. The method of claim 16 wherein said plurality of reactors each contain a T-cell and wherein the first nucleic acid molecule encoding one chain of an immune receptor is from an TCRα gene and the second nucleic acid molecule encoding another chain of an immune receptor is from an TCRβ gene.

18. The method of claim 16 wherein said plurality of reactors each contain a B-cell and wherein the first nucleic acid molecule encoding one chain of an immune receptor is from an IgH gene and the second nucleic acid molecule encoding another chain of an immune receptor is from an IgK gene.

19. The method of claim 16 wherein said plurality of reactors each contain a B-cell and wherein the first nucleic acid molecule encoding one chain of an immune receptor is from an IgH gene and the second nucleic acid molecule encoding another chain of an immune receptor is from an IgL gene.

20. The method of claim 15 wherein said sample is from a patient with an autoimmune disease, an infectious disease or a cancer.

* * * * *